United States Patent
Roein Peikar et al.

(10) Patent No.: US 10,383,707 B2
(45) Date of Patent: Aug. 20, 2019

(54) TEETH REPOSITIONING SYSTEMS AND METHODS

(71) Applicants: Seyed Mehdi Roein Peikar, Los Angeles, CA (US); James Sylvester Wratten, Jr., Waterville, NY (US)

(72) Inventors: Seyed Mehdi Roein Peikar, Los Angeles, CA (US); James Sylvester Wratten, Jr., Waterville, NY (US)

(73) Assignee: MECHANODONTICS, INC., Los Angeles, CA (US)

(*) Notice: Subject to any disclaimer, the term of this patent is extended or adjusted under 35 U.S.C. 154(b) by 168 days.

(21) Appl. No.: 15/370,704

(22) Filed: Dec. 6, 2016

(65) Prior Publication Data

US 2017/0156823 A1    Jun. 8, 2017

Related U.S. Application Data

(60) Provisional application No. 62/263,659, filed on Dec. 6, 2015, provisional application No. 62/352,025, filed
(Continued)

(51) Int. Cl.
*A61C 7/22* (2006.01)
*A61C 7/14* (2006.01)
(Continued)

(52) U.S. Cl.
CPC ........... *A61C 7/22* (2013.01); *A61C 7/002* (2013.01); *A61C 7/10* (2013.01); *A61C 7/12* (2013.01);
(Continued)

(58) Field of Classification Search
CPC .... A61C 7/20; A61C 7/28; A61C 7/06; A61C 7/10
See application file for complete search history.

(56) References Cited

U.S. PATENT DOCUMENTS

| | | | | |
|---|---|---|---|---|
| 2,266,860 A | * | 12/1941 | Griesinger | A61C 7/00 433/7 |
| 3,593,421 A | * | 7/1971 | Brader | A61C 7/20 433/21 |

(Continued)

FOREIGN PATENT DOCUMENTS

| | | |
|---|---|---|
| CN | 104146786 | 11/2014 |
| DE | 10 2015 009 345 | 1/2016 |

(Continued)

OTHER PUBLICATIONS

International Report on Patentability dated Jun. 21, 2018, from application No. PCT/US2016/065174.
(Continued)

*Primary Examiner* — Ralph A Lewis
(74) *Attorney, Agent, or Firm* — Foley & Lardner LLP

(57) ABSTRACT

Systems and methods of repositioning teeth, using one or more appliances for installing on a patient's teeth are described. The appliance includes an arch shaped member; a plurality of spring members coupled to or provided on the arch shaped member; and a plurality of securing members for securing to a corresponding plurality of the patient's teeth on a one-to-one basis, the securing members being supported by the arch shaped member. The arch shaped member and the plurality of springs, together, comprise a two dimensional structure having a length dimension and a width dimension with varying widths along the length dimension, that is bent into a three dimensional structure.

28 Claims, 44 Drawing Sheets

Related U.S. Application Data on Jun. 20, 2016, provisional application No. 62/393,526, filed on Sep. 12, 2016.

(51) Int. Cl.
  *A61C 7/00* (2006.01)
  *A61C 7/10* (2006.01)
  *A61C 7/12* (2006.01)
  *A61C 7/28* (2006.01)

(52) U.S. Cl.
  CPC ............... *A61C 7/145* (2013.01); *A61C 7/28* (2013.01); *A61C 7/287* (2013.01)

(56) References Cited

U.S. PATENT DOCUMENTS

| | | | |
|---|---|---|---|
| 3,792,529 A * | 2/1974 | Goshgarian | A61C 7/20 433/7 |
| 5,022,855 A | 6/1991 | Jeckel | |
| 5,255,352 A | 10/1993 | Falk | |
| 5,310,340 A * | 5/1994 | Zedda | A61C 7/00 433/18 |
| 5,312,247 A | 5/1994 | Sachdeva et al. | |
| 6,220,856 B1 | 4/2001 | Carano et al. | |
| 6,739,870 B2 | 5/2004 | Lai et al. | |
| 6,908,306 B2 | 6/2005 | Bowman et al. | |
| 7,234,934 B2 * | 6/2007 | Rosenberg | A61C 7/12 433/6 |
| 7,335,021 B2 * | 2/2008 | Nikodem | A61C 7/00 433/18 |
| 7,433,810 B2 | 10/2008 | Pavloskaia et al. | |
| 8,356,993 B1 | 1/2013 | Marston | |
| 8,517,726 B2 | 8/2013 | Kakavand et al. | |
| 8,685,184 B2 | 4/2014 | Johnson et al. | |
| 8,827,697 B2 * | 9/2014 | Cinader, Jr. | A61C 7/006 433/6 |
| 8,944,812 B2 | 2/2015 | Kuo | |
| 8,992,215 B2 | 3/2015 | Chapoulaud et al. | |
| 9,017,070 B2 | 4/2015 | Parker | |
| 9,427,291 B2 | 8/2016 | Khoshnevis et al. | |
| 9,532,854 B2 * | 1/2017 | Cinader, Jr. | A61C 7/006 |
| 2003/0096210 A1 | 5/2003 | Rubbert et al. | |
| 2004/0009449 A1 | 1/2004 | Mah et al. | |
| 2004/0048222 A1 | 3/2004 | Forster et al. | |
| 2006/0073436 A1 | 4/2006 | Raby et al. | |
| 2006/0234179 A1 | 10/2006 | Wen et al. | |
| 2008/0254403 A1 | 10/2008 | Hilliard | |
| 2009/0098500 A1 | 4/2009 | Diaz Rendon | |
| 2010/0075268 A1 | 3/2010 | Duran Von Arx | |
| 2010/0279245 A1 | 11/2010 | Navarro | |
| 2011/0269095 A1 * | 11/2011 | Singh | A61C 7/10 433/24 |
| 2012/0048432 A1 | 3/2012 | Johnson et al. | |
| 2012/0225398 A1 | 9/2012 | Fallah | |
| 2014/0120491 A1 | 5/2014 | Khoshnevis et al. | |
| 2014/0356799 A1 * | 12/2014 | Cinader, Jr. | A61C 7/006 433/11 |
| 2015/0157421 A1 | 6/2015 | Martz et al. | |
| 2015/0257856 A1 | 9/2015 | Martz et al. | |
| 2016/0058527 A1 | 3/2016 | Schumacher | |
| 2016/0135926 A1 | 5/2016 | Djamchidi | |
| 2017/0100215 A1 * | 4/2017 | Khouri | B23K 31/02 |
| 2018/0014916 A1 | 1/2018 | Cinader et al. | |
| 2018/0049847 A1 | 2/2018 | Oda et al. | |
| 2018/0338564 A1 | 11/2018 | Oda et al. | |

FOREIGN PATENT DOCUMENTS

| | | |
|---|---|---|
| EP | 0 400 932 | 5/1990 |
| EP | 0 551 800 A1 | 7/1993 |
| GB | 2 521 046 | 6/2015 |
| SU | 1502023 | 3/1987 |
| WO | WO-2007/021468 | 2/2007 |
| WO | WO-2010/146192 | 12/2010 |
| WO | WO-2014/088422 | 6/2014 |
| WO | WO-2016/149007 A1 | 9/2016 |
| WO | WO-2016/149008 A1 | 9/2016 |

OTHER PUBLICATIONS

International Search Report and Written Opinion dated Mar. 13, 2017, from related international application No. PCT/US2016/065174.

* cited by examiner

TEETH REPOSITIONING SYSTEMS AND METHODS

CROSS-REFERENCE TO RELATED PATENT APPLICATIONS

This application claims priority from each of U.S. Provisional Application No. 62/263,659, filed Dec. 6, 2015, U.S. Provisional Application No. 62/352,025, filed Jun. 20, 2016, and U.S. Provisional Application No. 62/393,526, filed Sep. 12, 2016, each of which is incorporated herein by reference in its entirety.

BACKGROUND OF THE INVENTION

1. Field of Invention

Present embodiments relate generally to systems and methods for repositioning teeth, including orthodontic systems and methods that include or employ one or more appliances that are installed (in a removable or non-removable manner) on a patient's teeth.

2. Background

In orthodontics, repositioning the teeth for aesthetic or other purposes has been performed by orthodontic devices traditionally referred to as braces. Braces are typically composed of brackets, archwires, O-rings and ligature wires. In addition to braces that typically have an appliance in front of the teeth, other methods include lingual orthodontics (which employs an appliance behind the teeth) and clear aligners such as Invisalign™ aligners (which employ transparent polymeric shells over the teeth).

SUMMARY OF THE DISCLOSURE

Embodiments described herein relate to systems and methods for repositioning teeth and include or employ one or more appliances that are installed (in a removable or non-removable manner) on a patient's teeth.

An appliance for installing on a patient's teeth according to examples of various embodiments comprises an arch shaped member; a plurality of spring members coupled to or provided on the arch shaped member; and a plurality of securing members for securing to a plurality of the patient's teeth, the securing members being supported by the arch shaped member. In such examples, the arch shaped member and the plurality of springs, together, comprise a two dimensional structure having a length dimension and a width dimension with varying widths along the length dimension, that is bent into a three dimensional structure.

In an appliance according to a further example, each securing member comprises: (a) a separate respective male connector element configured to engage with one or more separate respective female connector elements bonded to one or more of the patient's teeth; or (b) a separate respective cap configured to fit over and onto one or more of the patient's teeth.

In an appliance according to a further example, the arch shaped member is configured correspond to and extend along an arch of a jaw of the patient, when the appliance is installed on the patient's teeth; and each spring member is arranged along the arch shaped member at a location between two teeth in the jaw of the patient, when the arch shaped member extends along the jaw of the patient.

An appliance according to a further example includes a plurality of arms extending from the arch shaped member. Each arm is associated with one or more teeth of the patient, wherein each respective securing member of the plurality of securing members is attached to at least one different respective one of the arms relative to each other securing member. In such examples, each securing member comprises: (a) a separate respective male connector element configured to engage with one or more separate respective female connector element bonded to one or more of the patient's teeth; or (b) a separate respective cap configured to fit over and onto one or more of the patient's teeth.

In an appliance according to a further example, each respective spring member of the plurality of spring members is provided along a different respective one of the arms relative to each other spring member.

In an appliance according to a further example, each spring member is provided on a respective one of the arms, at a location between the arch shaped member and the securing member attached to the arm.

In an appliance according to a further example, each securing member is separated from and does not cover any portion of the spring member of the arm to which the securing member is attached.

In an appliance according to a further example, each securing member comprises a separate respective cap configured to fit over and onto one or more of the patient's teeth when the appliance is installed, such that the plurality of securing members comprises a plurality of caps that are arranged along the arch shaped member, and wherein each separate respective cap is disconnected from one or more other caps of the plurality of caps.

In an appliance according to a further example, each securing member comprises a T shaped member that is configured to engage with a slot in a female connector element bonded to one of the patient's teeth.

An appliance for installing on a patient's teeth according to further examples of embodiments comprises an arch shaped member; a plurality of arms extending from the arch shaped member, each arm being associated with one or more different respective ones of the patient's teeth relative to each other arm of the plurality of arms; and a plurality of securing members for securing to a plurality of the patient's teeth, wherein each respective securing member of the plurality of securing members is attached to one or more of the arms.

In an appliance according to further examples of the above embodiments, each respective securing member of the plurality of securing members is attached to a different respective one of the arms relative to each other securing member of the plurality of securing members.

In an appliance according to further examples of the above embodiments, each securing member comprises: (a) a separate respective male connector element configured to engage with one or more respective female connector elements bonded to one or more of the patient's teeth; or (b) a separate respective cap configured to fit over and onto one or more of the patient's teeth.

An appliance according to further examples of the above embodiments includes a plurality of spring members coupled to or provided on one or more of the plurality of arms such that one or more of the arms includes at least one spring member.

In an appliance according to further examples of the above embodiments each spring member is provided on a respective one of the arms, at a location between the arch shaped member and the securing member attached to the arm.

In an appliance according to further examples of the above embodiments each securing member is separated from and does not cover any portion of the spring member of the arm to which the securing member is attached.

In an appliance according to further examples of the above embodiments each securing member comprises a separate respective cap configured to fit over and onto one or more of the patient's teeth when the appliance is installed, such that the plurality of securing members comprises a plurality of caps that are arranged along an arch formed by the arch shaped member, and wherein each separate respective cap is disconnected from one or more other caps of the plurality of caps.

A method of making an appliance for installing on a patient's teeth according to examples of embodiments comprises cutting a flat sheet of material into a two dimensional shape structure having a length dimension and a width dimension, and a thickness corresponding to the thickness of the sheet material; bending the two dimensional shape structure into a three dimensional structure having an arch shaped member, and a plurality of spring members coupled to or provided on the arch shaped member; and supporting a plurality of securing members on the arch shaped member, the plurality of securing members for securing to a plurality of the patient's teeth.

In a method according to further examples, each securing member comprises: (a) a separate respective male connector element configured to engage with one or more respective female connector elements bonded to one or more of the patient's teeth; or (b) a separate respective cap configured to fit over and onto one or more of the patient's teeth.

In a method according to further examples, the arch shaped member is configured correspond to and extend along an arch of a jaw of the patient, when the appliance is installed on the patient's teeth; and each spring member is arranged along the arch shaped member at a location between two teeth in the jaw of the patient, when the arch shaped member extends along the jaw of the patient.

In a method according to further examples, cutting further comprises cutting the flat sheet of material to form a plurality of arms extending from the arch shaped member, each arm being associated with one or more of the patient's teeth, wherein supporting the plurality of securing members comprises providing each respective securing member of the plurality of securing members on a different one or combination of the arms relative to each other securing member.

In a method according to further examples, each securing member comprises: (a) a separate respective male connector element configured to engage with one or more respective female connector elements bonded to one or more of the patient's teeth; or (b) a separate respective cap configured to fit over and onto one or more of the patient's teeth.

In a method according to further examples, each respective spring member of the plurality of spring members is provided along a different respective one of the arms relative to each other spring member.

In a method according to further examples, each spring member is provided on a respective one of the arms, at a location between the arch shaped member and the securing member attached to the arm.

In a method according to further examples, supporting a plurality of securing members comprises supporting each securing member in a position separated from and not covering any portion of the spring member of the arm to which the securing member is attached.

In a method according to further examples, supporting a plurality of securing members comprises providing a separate respective cap configured to fit over and onto one or more of the patient's teeth when the appliance is installed, and supporting each cap such that the caps are arranged along the arch shaped member, and such that each separate respective cap is disconnected from one or more other caps of the plurality of caps.

In a method according to further examples, wherein supporting a plurality of securing members comprises supporting a plurality of T shaped members, each T shaped member being configured to engage with a slot in a female connector element bonded to one of the patient's teeth.

A method according to further examples, further comprising: obtaining a three dimensional image or template of a desired tooth arrangement of the patient's teeth; and converting the three dimensional image or template into a two dimensional image or template; wherein the cutting of the flat sheet of material into the two dimensional structure comprises cutting the flat sheet of material to a shape corresponding to the two dimensional image or template.

In a method according to further examples, the flat sheet of material comprises a sheet of Nitinol.

In a method according to further examples, the flat sheet of material comprises a sheet of memory shape metal.

In a method according to further examples, at least one of length dimension or the width dimension of the two dimensional shape structure varies over the width or length of the two dimensional shape structure.

BRIEF DESCRIPTION OF THE DRAWINGS

FIG. 13b is a perspective representation of a female connector element of the type in FIG. 13a.

FIG. 16b is a perspective view of an example of a female connector element that may be employed with the male connector element of FIG. 16a.

DETAILED DESCRIPTION

Figure 1:
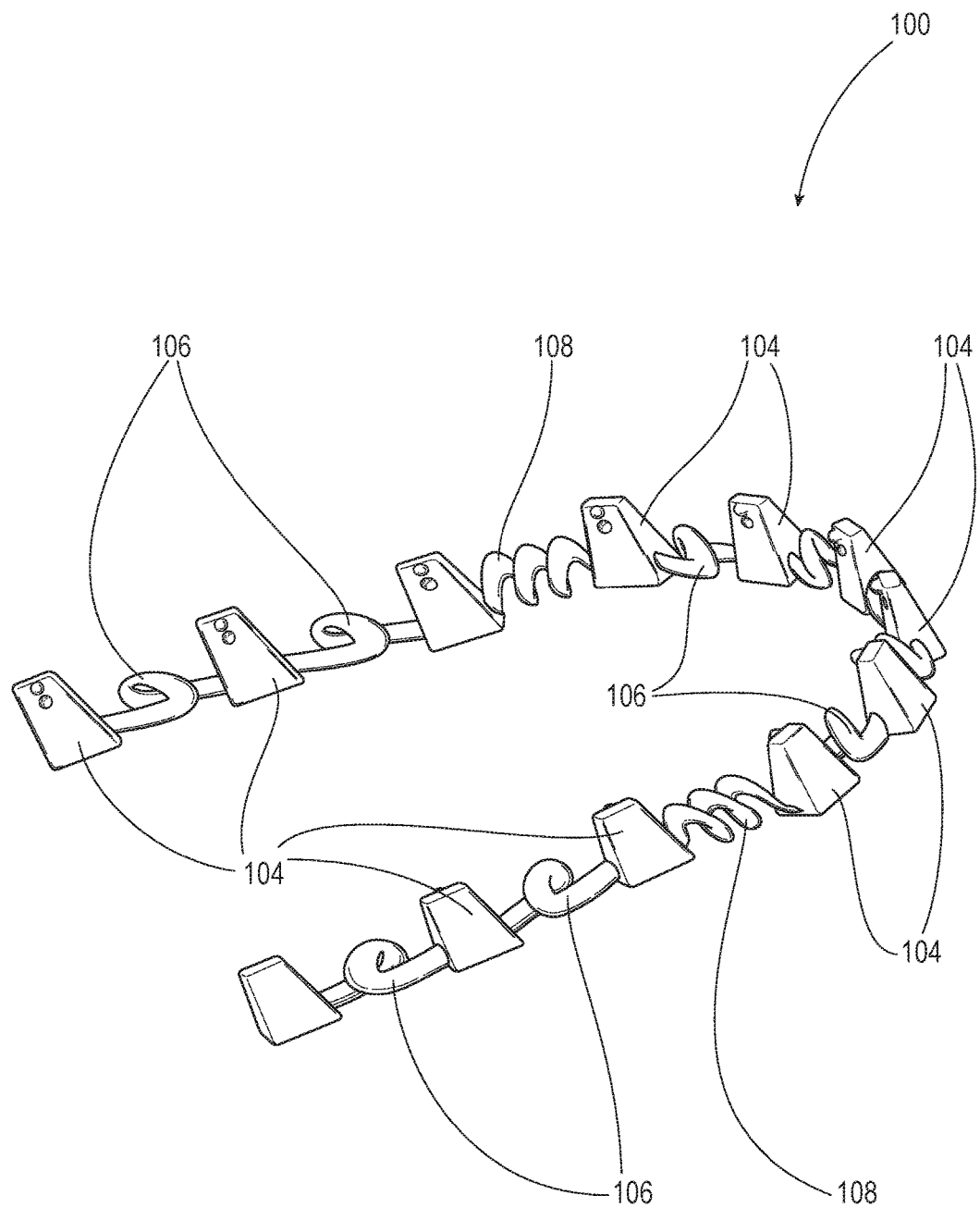
FIG. 1 is a perspective representation of an appliance according to an example of a first embodiment.

In the following description of various embodiments, reference is made to the accompanying drawings which form a part hereof and in which are shown by way of illustration specific embodiments in which the invention may be practiced. It is to be understood that other embodiments may be utilized, and structural changes may be made without departing from the scope of the various embodiments disclosed in the present disclosure.

Embodiments described herein relate to systems and methods for repositioning teeth. Particular embodiments relate to systems and methods for repositioning teeth from an original tooth arrangement (OTA) to a desired final tooth arrangement (FTA). In particular embodiments, tooth repositioning can be accomplished in one single step, by using one appliance. In other embodiments, tooth repositioning involves multiple steps performed progressively, by using multiple appliances. Embodiments involving multiple steps (or multiple appliances, or both) may include one or more intermediate tooth arrangements (ITAs) between an original tooth arrangement (OTA) and a desired final tooth arrangement (FTA).

Certain embodiments use non-sliding mechanics in which one or more appliances can be installed behind the teeth for aesthetically concerned patients. Other embodiments may employ other suitable mechanics to install one or more appliances behind or in front of the patient's teeth, or both behind and in front of the patient's teeth. The decision of whether or not to place the appliance in front of or behind the teeth is typically made by a clinician, doctor or other trained personnel, with the patient.

Certain embodiments described herein include or employ a fixed appliance that cannot be removed by the patient, once the appliance is installed on the patient's teeth. Other embodiments described herein include or employ a removable appliance that can be selectively removed and installed on the patient's teeth, by the patient. Embodiments that include or employ a fixed appliance may require or involve less patient cooperation and training, as compared to embodiments that include or employ removable orthodontic techniques.

Particular embodiments described herein can reduce the number of patient visits to the clinician as well as the chair time for the clinician and the patient. In addition, particular embodiments can shorten the total treatment time as compared to traditional orthodontics procedures.

In particular embodiments described herein, the planning of tooth movement can be computerized, which can simplify the treatment process for the clinician and can increase treatment precision as compared to traditional techniques.

One or more appliances and methods described herein may include or be combined with one or more bone anchorage devices including, but not limited to, temporary anchorage devices, mini-plates, implants and the like.

Systems or methods according to a first embodiment include or employ a pin and tube style appliance. Certain pin and tube type appliances have been employed in traditional systems, such as a Begg appliance system. An appliance according to the first embodiment includes male connector elements and one or more springs between adjacent male connector elements. In certain examples of the first embodiment, one or more springs are provided between each male connector element and each adjacent male connector element. In other examples of the first embodiment, one or more springs are provided between some, but not all of the pairs of adjacent male connector elements. For example, a rigid portion of the appliance may be provided between one or some pairs of adjacent male connector elements. In further examples, one or more springs may be provided between male connector elements that are not directly adjacent with each other. Each spring is a force-generating component of the appliance. In particular embodiments, each spring is made of a flexible material, such as, but not limited to a shape memory alloy, such as, but not limited to nitinol. In particular embodiments, one or more springs or other portions of the appliance (or the entire appliance) is made from a flat sheet of flexible material, such as a shape memory alloy, such as, but not limited to nitinol, that is cut into a desired two-dimensional shape and then bent into a desired three dimensional shape of an appliance. In such embodiments, the two-dimensional shape may be configured in desired widths as well as lengths, which can provide additional design options as compared to traditional bent wire appliance systems in which a single-diameter wire is bent and set into a desired shape. In particular embodiments, computerized design and manufacturing may be employed to design or to configure the two-dimensional shape and/or to bend the two-dimensional shape into the three dimensional shape of the appliance. In particular examples, each spring is designed, using computerized design techniques, where the design takes into account which tooth is to be moved as well as the desired movement amount and direction of the tooth.

In the first embodiment, the male connector elements are configured to engage with female connector elements or brackets, which are attached on surfaces of the teeth. The female connector elements or brackets may be customized in size and/or shape for each tooth or for each patient (or both). Alternatively, the female connector elements or brackets may be configured for application to any patient or tooth (or a group of multiple patients or teeth) and may not be customized for each tooth or patient. Any suitable female connector element configured to engage and secure with a male connector element on the appliance may be employed in various embodiments described herein, including, but not limited to examples of female connector elements described herein, traditional twin brackets, self ligating brackets, or the like.

Systems or methods according to examples of a second embodiment include or employ an appliance that has a plurality of separate arms configured to connect to a corresponding plurality of the patient's teeth, where each arm of the appliance is configured to connect to a different respective tooth relative to each other arm of the appliance. In further examples of the second embodiment, the appliance may include one arm configured to connect to a plurality of teeth, or multiple separate arms configured to connect to a corresponding one of the patient's teeth, or various combinations of arm-to-tooth connections as described herein. In such examples of the second embodiment, the appliance includes a single rigid bar, to which each of the separate arms is attached. In other examples, the appliance includes more than one rigid bar, with one or more arms attached to each rigid bar. One or more (or each) arm may include one or more springs. In particular examples, each arm (or each spring, or both) may be designed, using computerized design techniques, where the design takes into account which tooth is to be moved as well as the desired movement amount and direction of the tooth.

In an appliance according to the second embodiment, a separate respective male connector element may be formed on or otherwise attached to each respective arm, for example, at an end of each arm opposite to the arm end that attaches to the rigid bar. Each male connector element may be configured to engage with a respective female connector element or bracket.

Similar to the first embodiment described above, the female connector elements or brackets of the second embodiment may be customized in size and/or shape for each tooth or for each patient (or both). Alternatively, the female connector elements or brackets may be configured for application to any patient or tooth (or a group of multiple patients or teeth) and may not be customized for each tooth or patient. Unlike certain traditional orthodontics techniques in which all of the teeth are connected to a single arch wire, such that moving one tooth can result in an unintentional movement of nearby teeth, particular embodiments described herein allows the clinician to control the movement of each tooth independently of the other teeth.

In particular examples of the first and second embodiments, the female connector element is configured as a twin bracket (e.g., having a vertical slot and a transverse, horizontal slot) to which the male connector element locks, where the male connector element is configured as a T shaped structure or wire that can be engaged in the slots in the twin bracket. After engagement, the T shaped structure of the male connector element may be secured to the twin bracket by one or more ligature wires, O-rings or other suitable securing mechanisms, for example, by a clinician during installation of the appliance on a patient's teeth. In other examples, the female connector element is configured as a self-ligating bracket, then the self-ligating bracket may "close" and hold the T arm securely, with or without an additional securing mechanism. In other examples, the female connector element and the male connector element has other suitable configurations that allow for selectively connecting and disconnecting those elements, with or without an additional securing mechanism as described above.

Systems or methods according to a third embodiment include or employ an appliance that has a configuration similar to the first embodiment, but are further configured to be selectively removable, to allow a patient (or clinician) to selectively install and remove the appliance from a patient's teeth. An appliance according to the third embodiment includes a plurality of aligner caps instead of the male connector elements described above. Each aligner cap is configured to secure to a respective tooth by fitting over and onto the tooth. In other examples, one or more of the aligner caps may be configured to secure to a group of teeth per cap. For example, the aligner caps may comprise acrylic caps or caps made of other suitable materials, such as materials that help to retain each cap to a patient's tooth. In particular embodiments, additional or alternative connector elements such as, but not limited to clasps or other attachment mechanisms) may be provided to assist in attaching one or more (or each) of the caps to a respective tooth.

In an appliance according to the third embodiment, one or more springs may be provided between adjacent aligner caps. In certain examples of the third embodiment, one or more springs are provided between each aligner and each adjacent aligner cap. In other examples of the third embodiment, one or more springs are provided between some, but not all of the pairs of adjacent aligner caps. For example, a rigid portion of the appliance may be provided between one or some pairs of adjacent aligner caps. In further examples, one or more springs may be provided between aligner caps that are not directly adjacent with each other. Each spring is a force-generating component of the appliance. In particular embodiments, each spring is made of a flexible material, such as, but not limited to a shape memory alloy, such as, but not limited to nitinol.

In the third embodiment, each cap may be customized in size and/or shape to correspond to the size and shape of the tooth (or teeth) to which the cap fits. Alternatively, the aligner caps are configured for application to any patient or tooth (or a group of multiple patients or teeth) and are not customized for each tooth or patient. In certain examples of the third embodiment, each aligner cap may be separately connected to a support bar and not directly connected to any other caps for adjacent teeth. In other examples, one or more of the aligner caps may be connected to one or two adjacent aligner caps, such that two or more aligner caps may be connected together along the arch shaped structure of the support bar. This gives an appliance according to the third embodiment significantly greater flexibility, which can allow the clinician to use fewer appliances to complete a treatment. In particular examples, each cap is associated with (configured to secure to) a single, respective tooth and is separately attached to the support bar relative to each other cap of the appliance, such that the plurality of separate caps secure to a plurality of separate teeth on a one to one basis. In other examples, one or more caps of the appliance is configured to cover and fit over (secure to) multiple adjacent teeth. Such one or more caps configured to secure to multiple adjacent teeth may be separately attached to the support bar, separate from one or more other, adjacent caps of the appliance.

Systems or methods according to a fourth embodiment include or employ an appliance that has a configuration similar to the second embodiment, but is further configured to be selectively removable, to allow a patient (or clinician) to selectively install and remove the appliance from a patient's teeth. Similar to the second embodiment, an appliance according to examples of the fourth embodiment has a plurality of separate arms configured to individually connect to a corresponding plurality of teeth, where each arm of the appliance is configured to connect to a different respective tooth relative to each other arm of the appliance. In further examples of the fourth embodiment, the appliance may include one arm configured to connect to a plurality of teeth, or multiple separate arms configured to connect to a corresponding one of the patient's teeth, or various combinations of arm-to-tooth connections as described herein. The appliance includes a single rigid bar, to which each of the separate arms is attached. In other embodiments, the appliance includes more than one rigid bar, with one or more arms attached to each rigid bar.

Instead of the male connector elements of the second embodiment, an appliance according to the fourth embodiment includes a separate respective aligner cap formed on or otherwise attached to each respective arm, for example, at an end of each arm opposite to the arm end that attaches to the rigid bar. The aligner caps of the fourth embodiment may be configured similar to the aligner caps described herein for the third embodiment, to secure to a patient's teeth by fitting over and onto the teeth. However, the separate aligner caps of the fourth embodiment are attached to ends of the separate respective arms.

Systems or methods according to the second and fourth embodiments (in which an appliance includes a plurality of separate arms configured to individually connect to designated teeth or to a corresponding plurality of teeth) can provide distinct advantages of providing and controlling individual tooth movement. Such advantages can allow a clinician to reduce round tripping of the teeth thereby reducing treatment time, root resorption, and the number of trips the patient is required to take to the orthodontist. Thus, in comparison to traditional orthodontic techniques in which a plurality of the teeth are connected to a single arch wire such that moving one tooth results in the unintentional movement of nearby teeth, particular embodiments described herein allow a clinician to control the movement of each tooth independently each of the other teeth. Additional control may be provided in examples in which the appliance includes temporary anchorage device (TAD) holders as described herein.

Systems or methods according to the third and fourth embodiments (in which an appliance includes a plurality of aligner caps configured to secure to a patient's teeth by fitting over and onto the teeth) can provide distinct advantages of an appliance that can be easily removed by the patient or clinician, in a manner similar to what is done with traditional clear aligners.

In addition, embodiments described herein allow for computerized design and manufacturing, for example, to design or to custom configure various aspects of one or more appliances, including designing or customizing one or more of the width, thickness, shape and spring tension or strength of each spring in an appliance. Computerized design and manufacturing techniques may be employed to design and/or manufacture each spring in appliances according to any of the embodiments, or each arm in appliances according to the second and fourth embodiments, based on which tooth or teeth is/are to be moved and the desired amount and direction of movement. In particular embodiments, a computerization of the shape and features of the appliance and/or manufacturing techniques described herein, can provide significant advantages over traditional pin-and-tube appliances, including those made from manual or robot bent wires having "U"-shaped segments between pairs of adjacent teeth.

With systems or methods according to embodiments described herein, translational orthodontic tooth movement is feasible in one or more, or all three directions of space (i.e. mesiodistal, buccolingual and occlusogingival). Alternatively or in addition to translational movement of the teeth, one or more, or all three rotational movements including torque, angulation and rotation (i.e. buccolingual root torque, mesiodistal angulation and mesial out-in rotation) are possible.

First Embodiment

As discussed above, systems or methods according to a first embodiment include or employ a pin and tube style appliance. The appliance according to the first embodiment is configured to secure to a plurality of (or all of) the teeth of an upper jaw or a lower jaw of a patient. In particular embodiments, a system and method according to the first embodiment is a non-sliding system and method that employs an appliance having non-sliding mechanics. In certain examples, an appliance according to the first embodiment may be made, after rearranging a three dimensional (3D) digital OTA to a 3D digital FTA, and designing (via computer aided design or other suitable design techniques) an appliance shape that is configured to impart forces on the patient's teeth to move the teeth from the OTA to the FTA (or to an ITA, or from an ITA to an FTA or another ITA).

Figure 2:
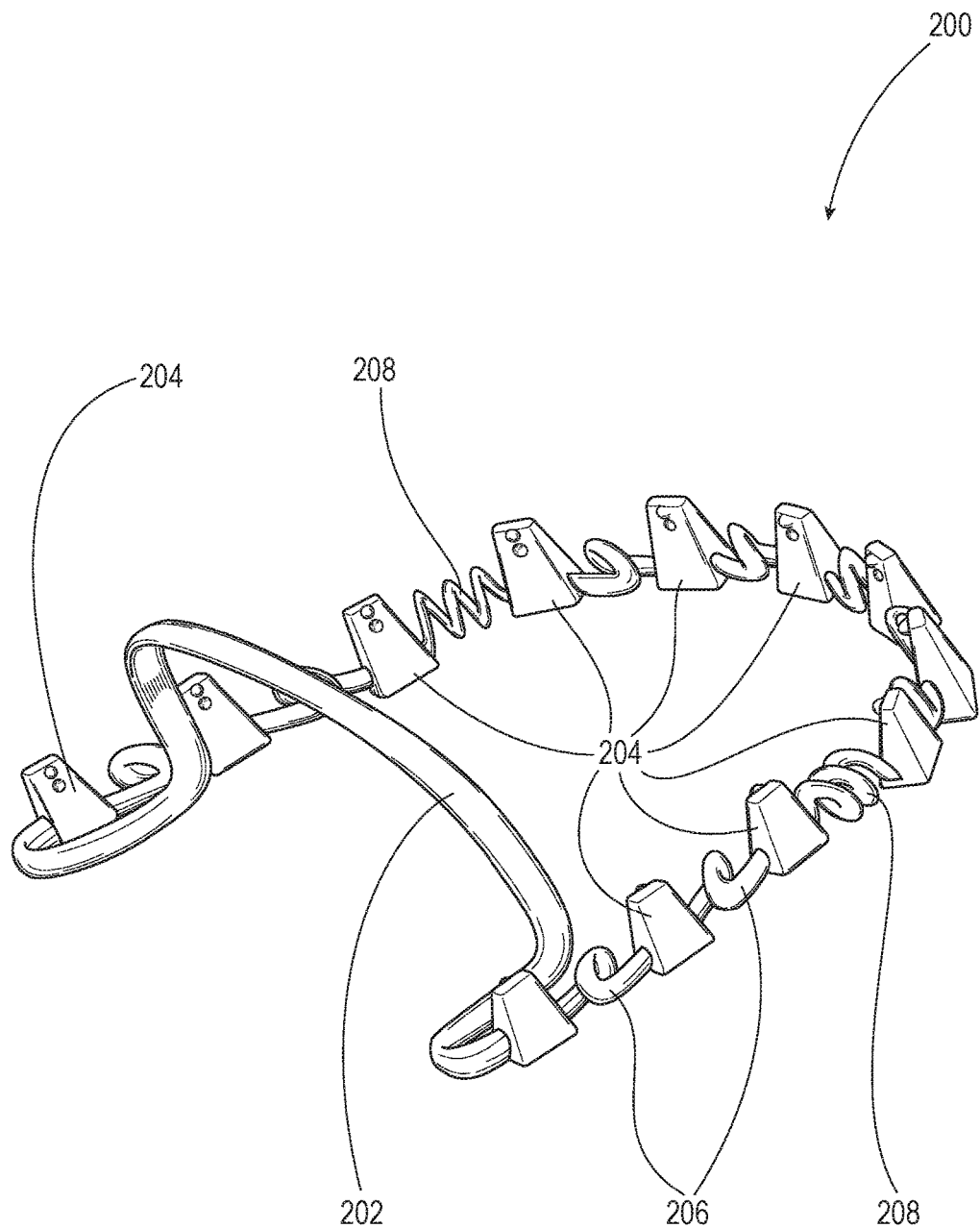
FIG. 2 is a perspective representation of an appliance according to another example of the first embodiment.
Figure 3:
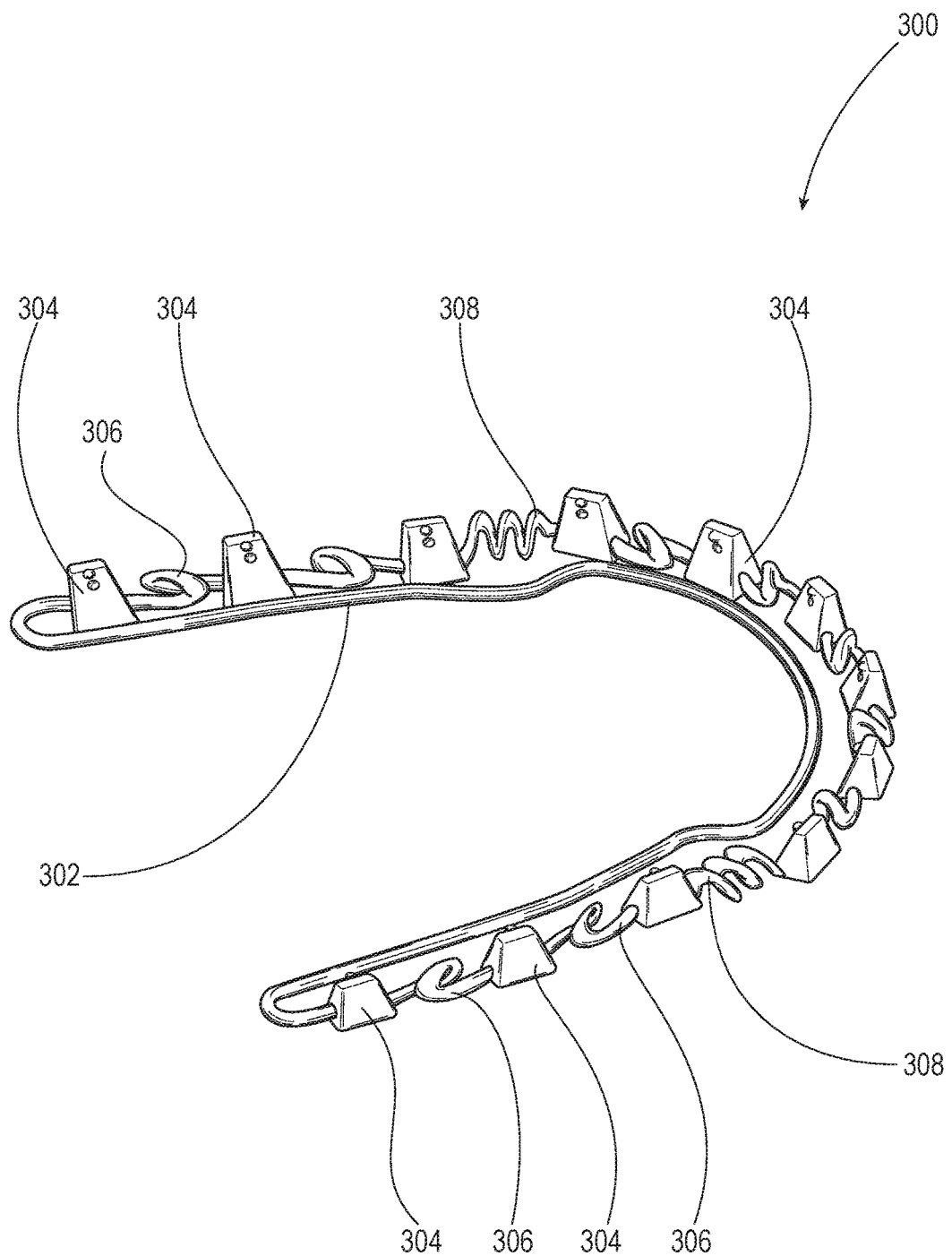
FIG. 3 is a perspective representation of an appliance according to another example of the first embodiment.

Examples of appliances 100, 200 and 300 according to the first embodiment are shown in FIGS. 1-3, respectively. The appliances 100, 200 and 300 (and components of the appliances) may be made of any suitable material including, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in a single structure.

In FIG. 1, the example appliance 100 includes an arch-shaped structure that is configured for an upper jaw (to follow the arch of the upper jaw of a patient). The appliance 100 does not include a palatal arch feature. The example appliance 200 in FIG. 2 is similar to the appliance of FIG. 1, but includes a palatal arch feature 202. The example appliance 300 in FIG. 3 includes an arch-shaped structure that is configured for a lower jaw (to follow the arch of the lower jaw of a patient) and includes a stabilizing lingual arch feature 302. In other examples, an appliance according to the first embodiment may be configured for a lower jaw but without a lingual arch feature. Accordingly, certain examples of appliances according to the first embodiment include a palatal arch feature or a lingual arch feature, while other examples of appliances according to the first embodiment may be configured without a palatal arch feature or a lingual arch feature. Typically, the inclusion of a palatal arch feature or a lingual arch feature will depend upon the dental malocclusion type or on the clinician's preferences (or both).

The examples of appliances 100, 200 and 300 shown in FIGS. 1-3 include a plurality of male connector elements and a plurality of spring members. The appliance 100 of FIG. 1 includes male connector elements 104 and spring members 106 and 108. The appliance 200 in FIG. 2 includes male connector elements 204 and spring members 206 and 208. The appliance 300 in FIG. 3 includes male connector elements 304 and spring members 306 and 308. Each spring member is composed of a portion or segment of the appliance 100, 200 or 300 that has a shape or configuration and resiliency characteristics of a spring to, for example, exert one or more tension or compression forces, a force in one or more of the three directions, a torque in one or more of the three directions, or to absorb movement, or combinations thereof. In the example appliances 100, 200 and 300 in FIGS. 1-3, each spring member is arranged between a pair of adjacent male connector elements. In other examples, one or more spring members may be arranged between male connector elements that are not directly adjacent each other. In further examples, one or more pairs of adjacent male connector elements on the appliance may be connected by a rigid portion of the appliance, instead of a spring.

In the example appliances 100, 200 and 300, a mesiodistal spring is included between the male elements of the canines and the second premolars, for example, to impart a force directed to close a space created from an extracted first premolar by drawing one or both adjacent teeth toward the other adjacent tooth (teeth are not shown in FIGS. 1-3). In the appliance 100, the mesiodistal springs are shown at 108. In the appliance 200, the mesiodistal springs are shown at 208. In the appliance 300, the mesiodistal springs are shown at 308. One or both mesiodistal springs may be omitted from certain other examples of appliances according to the first embodiment.

The examples shown in FIGS. 1-3 include a separate, respective male connector element for each separate, respective tooth in the jaw to which it secures. In addition, the examples in FIGS. 1-3 include a separate, respective spring between each pair of adjacent male connector elements (and, thus, between each pair of adjacent teeth, when the appliance is installed on a patient). In other examples, an appliance according to the first embodiment may include fewer male connector elements than teeth in the jaw to which it secures, or may have springs arranged between one or more, but not all of the pairs of adjacent male connector elements. Typically, the number and tooth location of the male connector elements and springs will depend upon a desired tooth repositioning step or procedure, for example, as determined by the clinician.

When the appliance 100, 200 or 300 is secured to a patient's teeth, the spring members 106 and 108, or 206 and 208, or 306 and 308 are configured to impart the necessary forces on the teeth to move the teeth from their OTA to a desired FTA either directly in one step, or, alternatively, in multiple steps via one or more ITA(s). The spring members may be configured to move the teeth in one or more (or all three) translational directions. Alternatively or in addition, the spring members may be configured to move the teeth in one or more (or all three) rotational directions.

In the example appliances 100, 200 and 300 in FIGS. 1-3, the spring members are shown as having a spiral or loop configuration in which a segment of the spring forms one or more loops. In other examples, one or more (or all) of the springs may have other appropriate shapes, such as, but not limited to U shaped (having one or more U-shaped segments). In particular examples, the springs are formed by bent segments of an unitary arch-shaped structure of the appliance. In other examples, the springs are formed as separate components that are attached together with (or to form) an arch-shaped structure.

Figure 4A:
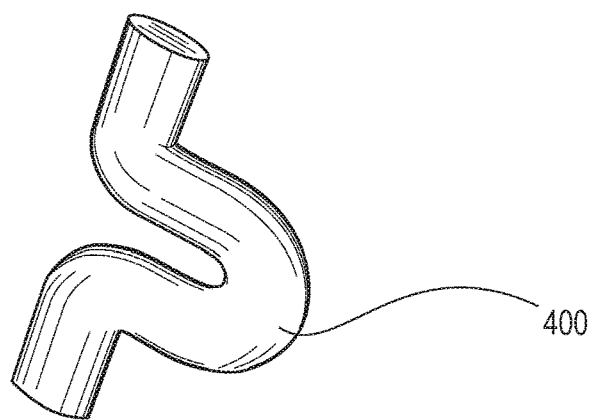
FIGS. 4a-c are perspective representations of a spring for an appliance according to various examples of first, second, third and fourth embodiments.
Figure 4B:
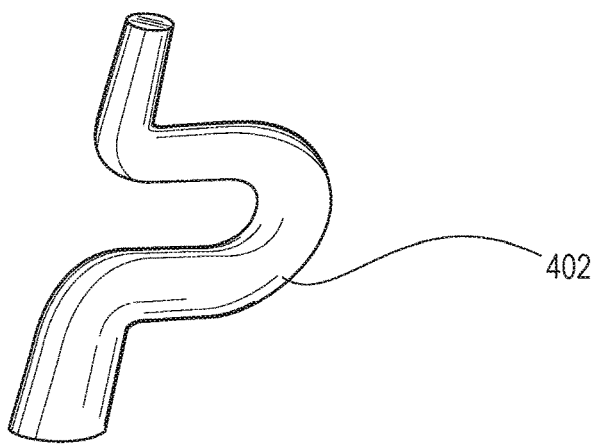
Figure 4C:
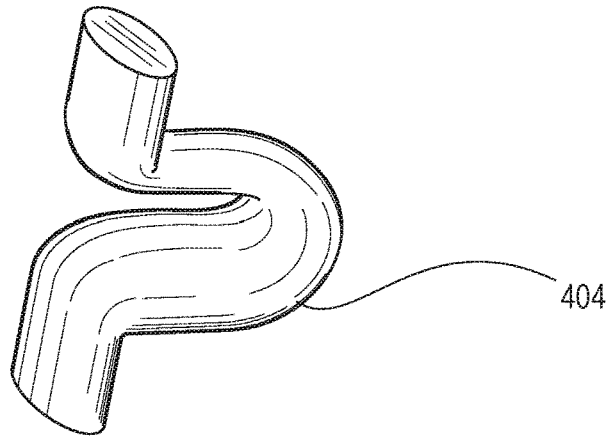

Examples of different U shaped springs 400, 402 and 404 that may be employed in appliances according to the first embodiment are shown in FIGS. 4a-4c. In the example of FIG. 4a, a U shaped spring 400 has an increased thickness in the occlusogingival direction, which restricts the flexibility of the appliance in that direction. In the example of FIG. 4b, a side of the spring 402 that is to be attached to the more mal-aligned tooth is thinner and more flexible than other portions of the spring. The spring may have a varying thickness, so as to be thinner (and more flexible) on the side where the tooth needs to be displaced further. In the example of FIG. 4c, the U shaped spring 404 is configured to be thinner and more flexible in an oblique direction, which enables an adjacent tooth to move simultaneously in the occlusogingival and buccolingual directions, for example, to move in a diagonal vector in-between the occlusogingival and buccolingual directions.

In particular examples, the direction and magnitude of force and torque applied by a spring is dependent, at least in part, on the shape, width, thickness and length of the spring. In such examples, the shape, width, thickness and length of each spring is selected and designed to produce a desired tooth movement and to take into account the position of the spring on the appliance (including the size and type of teeth between which the spring is connected). For example, the thickness and geometry of each spring may be selected or designed to increase the flexibility of the spring when the adjacent teeth need to be displaced further or when the teeth are smaller in size, such as, but not limited to lower incisors. In particular examples, processing and software systems with finite element analysis capabilities may be used to determine an optimal geometry and thickness of the springs, for example, to apply a force selected to accelerate the tooth movement in one or more of the buccolingual, occlusogingival and mesiodistal directions.

Figure 5:
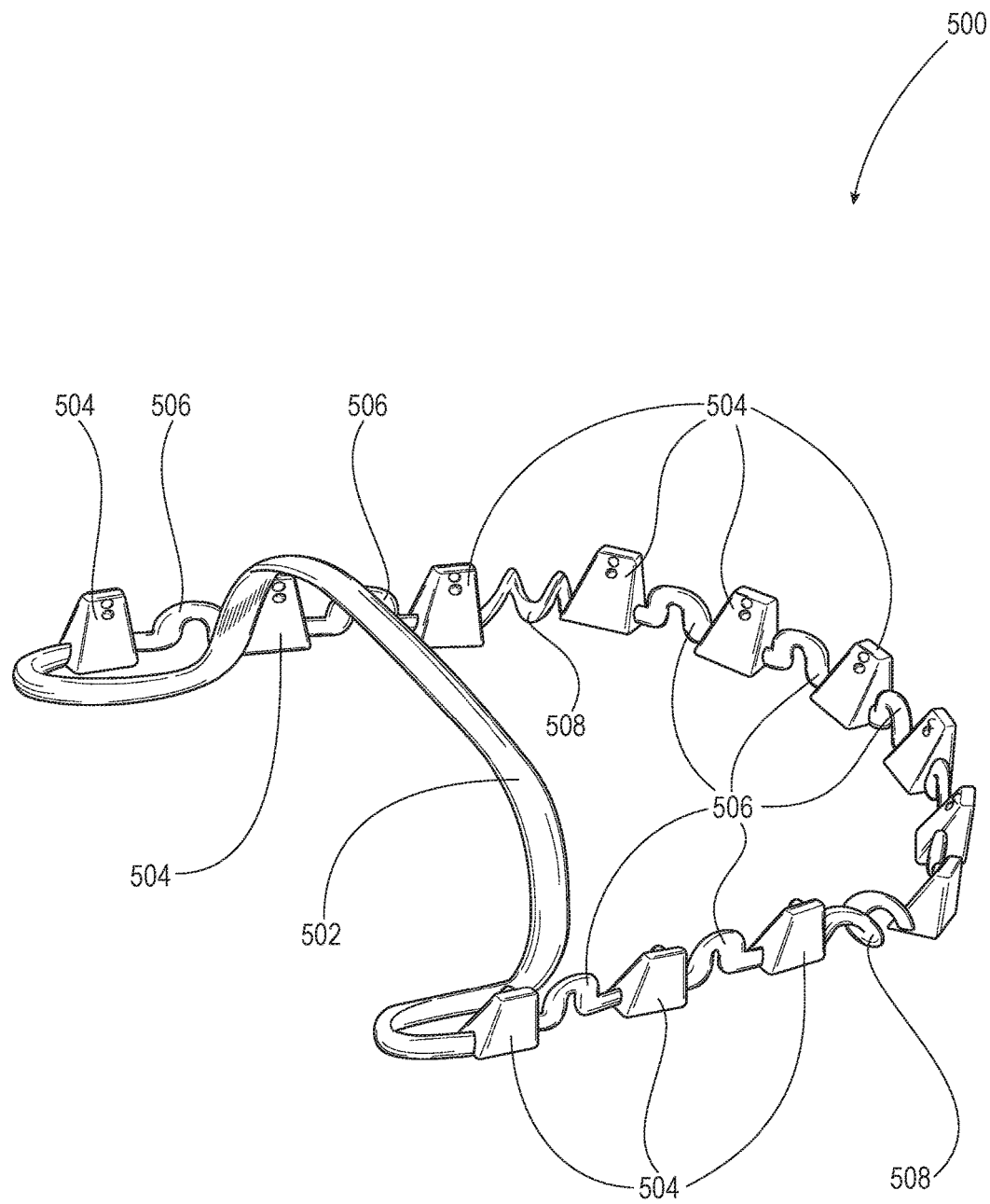
FIG. 5 is a perspective representation of an appliance according to another example of the first embodiment.
Figure 6:
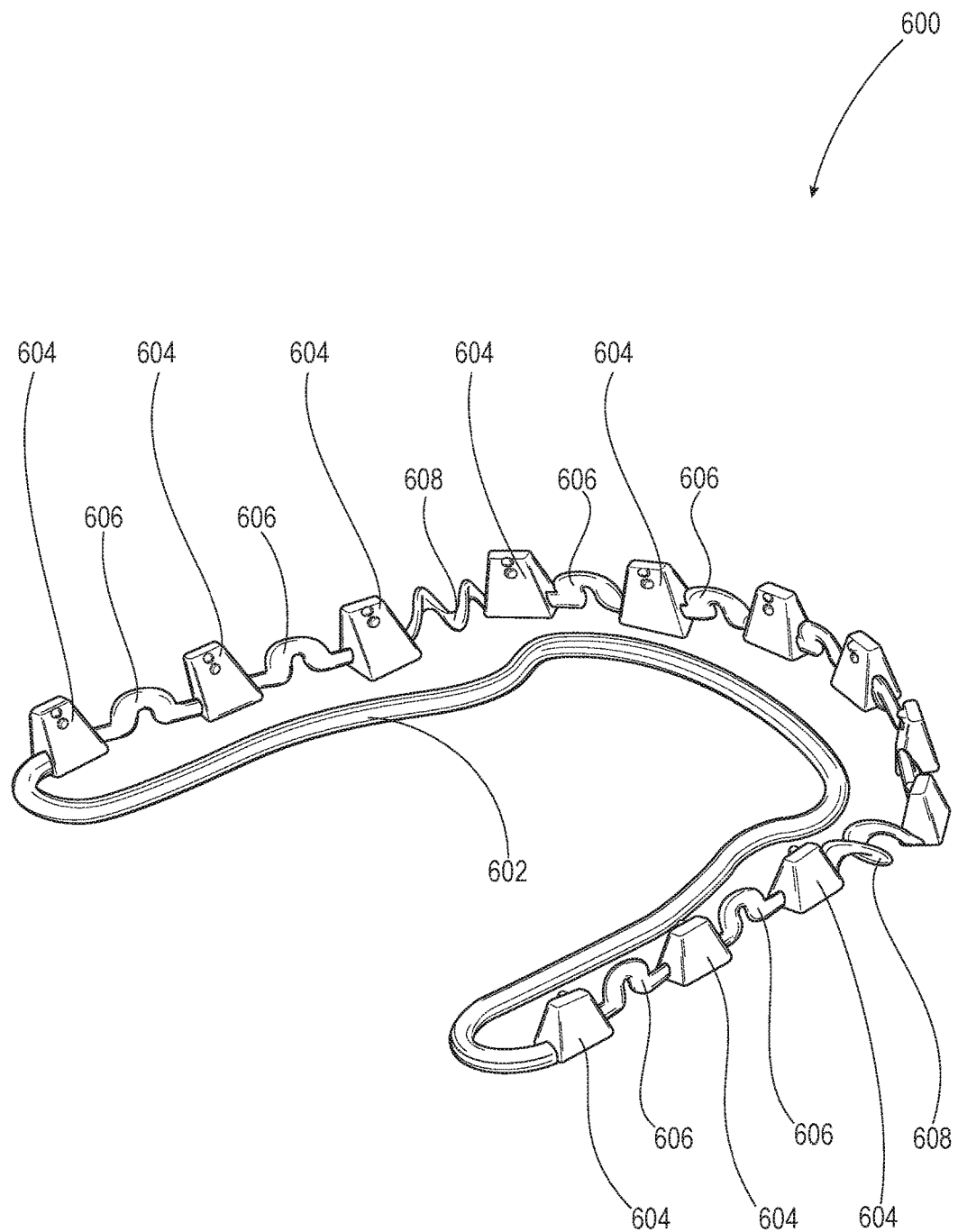
FIG. 6 is a perspective representation of an appliance according to another example of the first embodiment.

Further example appliances 500 and 600 are shown in FIGS. 5 and 6, respectively. Example appliance 500 in FIG. 5 is configured for teeth of an upper jaw and is similar to example appliance 200 in FIG. 2, but includes a plurality of U shaped spring members 506 between some of the adjacent pairs of male connector elements 504. The example appliance 600 in FIG. 6 is configured for teeth of a lower law and is similar to example appliance 300 in FIG. 3, but includes a plurality of U shaped spring members 606 between some of the adjacent pairs of male connector elements 604.

In addition, the appliances 500 and 600 include mesiodistal springs 508 or 608 between the male connector elements to be secured to female connector elements on the canines and second premolars, for example, to close a space created from extracted first premolars (teeth are not shown in FIGS. 5 and 6). The male connector elements 504 and 604 may have a configuration and operation similar to those described herein with respect to male connector elements 104, 204 and 304 in FIGS. 1-3. The example appliance 500 includes a palatal arch feature 502, while the example appliance 600 includes a lingual arch feature 602. The palatal arch feature 502 and the lingual arch feature 602 may be similar to the palatal arch feature 202 and lingual arch feature 302, respectively, as described herein. Other example appliances according to the first embodiment may not include a palatal arch feature or a lingual arch feature.

The appliances 500 and 600 may be designed to be installed after a first or subsequently used appliance (such as, but not limited to an appliance 100, 200 or 300 as shown in FIGS. 1-3) had moved the teeth from an OTA to an ITA (or from one ITA to another ITA) and was subsequently removed. Thus, the appliances 500 and 600 may be designed to move the teeth from an ITA to an FTA (or to another ITA). Alternatively, the appliances 500 and 600 may be designed to move the teeth from an OTA to an ITA, or from an OTA to an FTA without changing appliances at an ITA.

The example appliances 100, 200, 300, 500 and 600 shown in FIGS. 1-3, 5 and 6 do not include anchorage device holders. However, in other examples, one or more anchorage device holders, such as, but not limited to the anchorage device holders 812 and 904 (described in connection with examples in FIGS. 8 and 9) may be included in the appliances 100, 200, 300, 500 and 600, to allow a clinician to secure one or more temporary anchorage devices TADs (or other suitable anchorage device) as described herein with respect to anchorage device holders 812 and 904.

Example appliances 100, 200, 300, 500 and 600 as shown in FIGS. 1-3, 5 and 6 include a separate male connector element for securing to each separate, respective tooth of the jaw to which the appliance secures. In other examples, an appliance according to the first embodiment may be secured to fewer than all of the teeth in a jaw (or may include fewer male connector elements than teeth in the jaw to which it secures). For example, an appliance according to the first embodiment may be configured as a sectional appliance to move some, but not all of the teeth in a patient's jaw.

An example of such a scenario is when only the anterior teeth are misaligned and need to be moved. In that example, an appliance according to the first embodiment may be configured with male connector elements for connection to the anterior teeth in the jaw (and not to other teeth in the jaw). In other examples, a sectional type of appliance according to the first embodiment may be configured to open space for an implant or align teeth that are tipped into an extraction space. In those examples, an appliance according to the first embodiment may be configured with male connector elements for connection to one or more teeth that need to be moved to form the desired space or to correct tipping (and not other teeth in the jaw).

As discussed above, the male connector elements are configured to engage with and connect to female connector elements or brackets that are attached on surfaces of the teeth. Such female connector elements are attached to the teeth, prior to installation of the appliance 100, 200, 300, 500 or 600.

Various examples and configurations of male connector elements, and associated female connector elements may be employed in various examples of the first embodiment (and other embodiments) described herein. Certain examples of appliances according to the first embodiment include male connector elements as described and shown with respect to FIGS. 1-3, 5 and 6 (for securing to female connector elements as described with respect to FIG. 7). Other example appliances according to the first embodiment include male connector elements as described and shown with respect to FIGS. 8-12h (for securing to female connector elements as described with respect to FIGS. 13a and 13b). Yet other appliances according to the first embodiment include male connector elements as described and shown with respect to FIG. 15a (for securing to female connector elements as described with respect to FIG. 15b, as shown in FIG. 15c). Yet other appliances according to the first embodiment include male connector elements as described and shown with respect to FIG. 16a (for securing to female connector elements as described with respect to FIGS. 16b and 16c. Yet other example appliances according to the first embodiment include male connector elements as described and shown with respect to FIG. 17a (for securing to female connector elements as described with respect to FIG. 17b). Other example appliances according to the first embodiment include male connector elements as described and shown with respect to FIGS. 18e and 25 (for securing to female connector elements as described with respect to FIGS. 26a-f). Other example appliances according to the first embodiment include male connector elements as described and shown with respect to FIGS. 27a and 27b (for securing to female connector elements as described with respect to FIG. 28). Yet other appliances according to the first embodiment include male connector elements having other suitable configurations for securing to female connector elements having other suitable configurations.

In the examples shown in FIGS. 1-3, 5 and 6, each of the male connector elements includes a generally wedge-shaped body having a wide end portion and a narrow end portion, the wide end portion extending from or otherwise attached to the arch-shaped structure of the appliance. The narrow end portion of each male connector element has a protrusion and an indentation that engage a corresponding indentation and protrusion, respectively, on a female connector element, when the appliance is installed on a patient's teeth.

Figure 7:
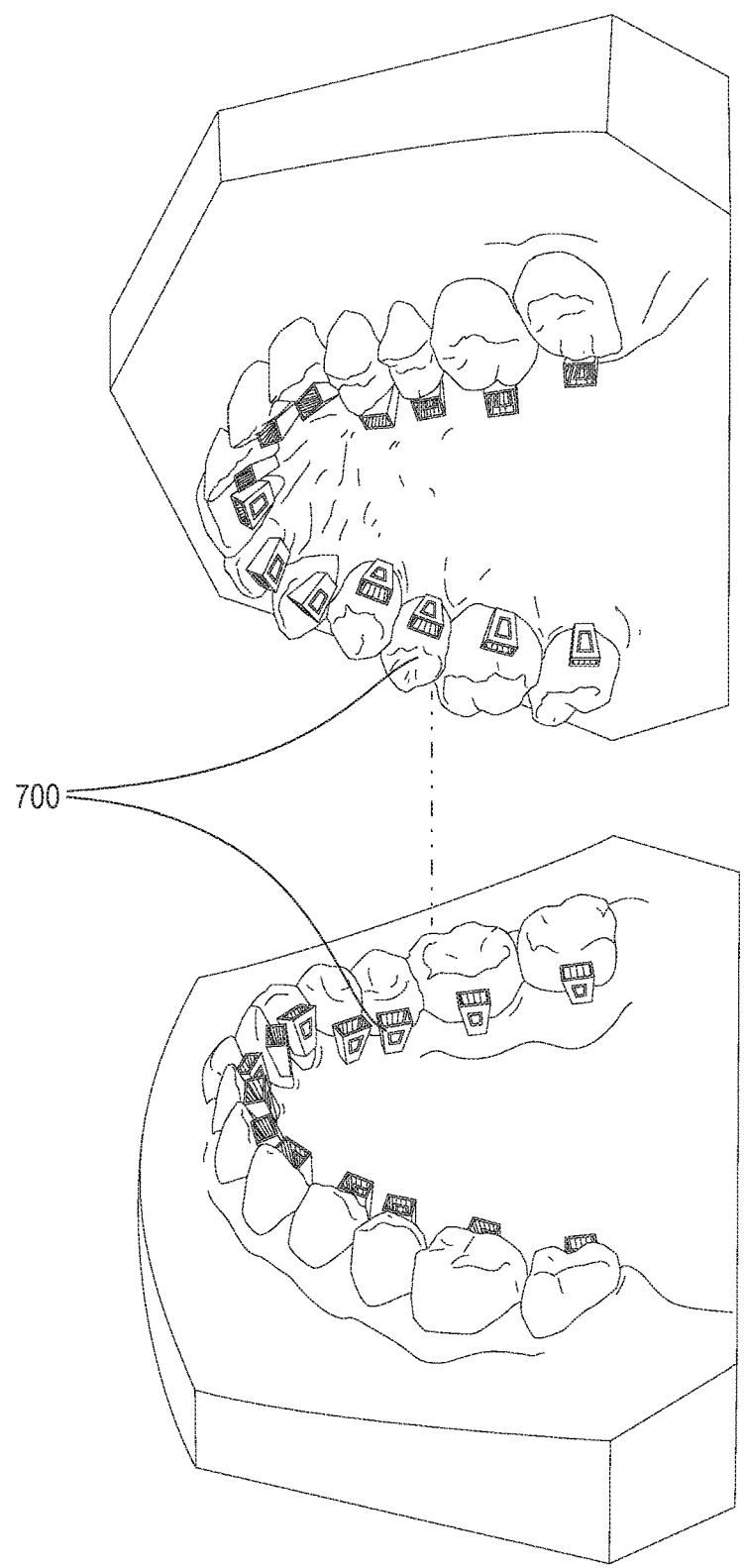
FIG. 7 is a perspective representation of an upper jaw and a lower jaw having an example of female connector elements.

FIG. 7 shows a representation of an OTA image of an upper and a lower jaw of a patient, on which examples of female connector elements 700 are attached to the lingual surface of the teeth, on the upper and lower arches. Female connector elements 700 are attached to the teeth on the upper arch, and similar female connector elements 700 are attached to the teeth on the lower arch. In other examples, the female connector elements 700 may be attached to the buccal surface of the teeth, for example, if preferred by the clinician.

A separate, respective female connector element 700 is secured to each respective tooth. The female connector elements provide a connection interface to connect one or more appliances to the teeth, according to the first and second embodiments described herein. While the drawing in FIG. 7 shows all of the teeth in each jaw as having female connector elements, other embodiments may employ separate, respective female connector elements on some, but not all of the teeth in the upper jaw or the lower jaw, for example, as selected by the clinician.

The female connector elements 700 can be attached to the teeth via direct or indirect bonding, or other suitable means for fixedly securing the elements to a surface of the teeth. Bonding materials may include adhesives such as, but not limited to composite resin. In the case of indirect bonding, a clinician may use a jig to increase the accuracy of the bracket placement. In particular examples, one or more (or all) of the female connector elements 700 are customized in size or shape to each tooth, and are configured to have the lowest profile possible (to minimize the size in the dimension extending away from the tooth, i.e., the buccolingual direction). Further examples may be configured to minimize size in the mesiodistal direction or the occlusoginival direction, or combinations thereof. In examples in which the female connector elements 700 are to be attached to the teeth via direct bonding, intraoral scanning or an impression of the arches may be taken after attaching the female elements on the teeth. The impressions or scans (or both) include and, thus, provide information to help identify the position of the female connector elements on the teeth. That information is used by clinicians, manufacturers or technicians in the design of the appliance, for example, to help identify appropriate positions on the appliance to place or form one or more male connector elements, for proper alignment with one or more female connector elements on the teeth.

The female connector elements 700 in FIG. 7 are configured to engage with male connector elements having configurations as shown in the examples appliances 100, 200, 300, 500 and 600 in FIGS. 1-3, 5 and 6. Each female connector element 700 in FIG. 7 includes a generally wedge-shaped basket structure, configured to receive a respective one of the generally wedge-shaped male elements 104, 204, 304, 504 or 604 when the appliance 100, 200, 300, 500 or 600 is installed on a patient's teeth. An interior surface of each generally wedge-shaped basket structure has an indentation and a protrusion that engage a corresponding protrusion and an indentation, respectively on a male connector element, when the male connector element is received in the generally wedge-shaped basket structure. In this manner, when the male connector element is received in the generally wedge-shaped basket structure, the male connector element (and, thus, the appliance) is secured to the female connector element (and, thus, the tooth to which the female connector element is attached). In other examples, the female connector element of appliances 100, 200, 300, 500 and 600 may have other suitable configurations for engaging and securing to an associated male connector element, including, but not limited to, further examples as described with reference to FIGS. 13b, 15b, 16b, 17b or FIG. 26e.

The appliances according to the first embodiment, and female connector elements associated with the first embodiment, may be manufactured in any suitable manner, including, but not limited to molding, casting, machining, 3D printing, stamping, extruding, or the like. However, in particular examples, appliances according to the first embodiment or female connector elements (or both) are made by cutting a two dimensional (2D) form of the appliance from a 2D sheet of material and bending the 2D form into a desired 3D shape of the appliance. As discussed below, such methods are particularly suitable for making appliances according to examples of the first embodiment described herein.

By cutting 2D member from a flat sheet of material, instead of a traditional single-diameter wire, a greater variety of 3D shapes may be made, as compared to shapes made by bending single-diameter wire. The cut 2D member may have designed or varying widths and lengths that, when bent into a desired shape, can result in portions of the 3D appliance having variances in thickness, width and length dimensions. In this manner, the 2D member can be cut into a shape that provides a desired thickness, width and length of spring members, arms, or other components of the appliance, when bent into the 3D shaped member of the appliance.

Figure 17A:
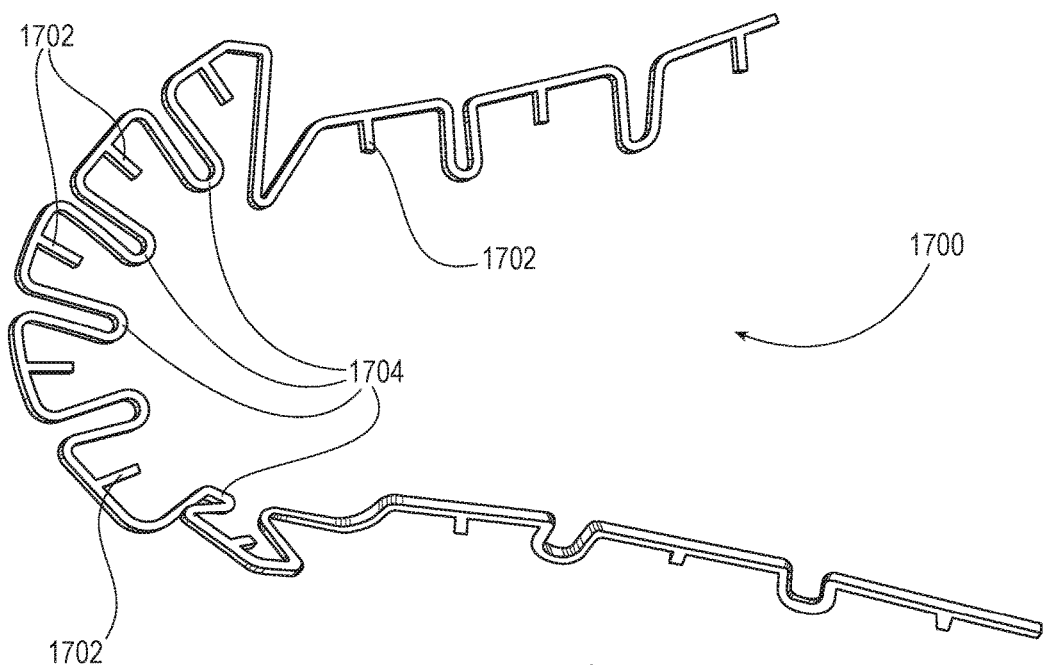
FIG. 17a is a perspective representation of an appliance or component of an appliance according to another example of the first embodiment.

An example of a 3D shaped member of an appliance, formed by bending a 2D member that was cut from a flat sheet of material is shown in FIG. 17a. In particular examples, the sheet material is Nitinol (NiTi). In other examples, the sheet material may be any suitable material such as, but not limited to, stainless steel, beta-titanium, cobalt chrome or other metal alloy, polymers or ceramics. In other examples (if practical for the desired appliance shape), an appliance according to the first embodiment may be configured from a wire material that is bent or otherwise formed into a desired 3D shape.

Figure 17B:
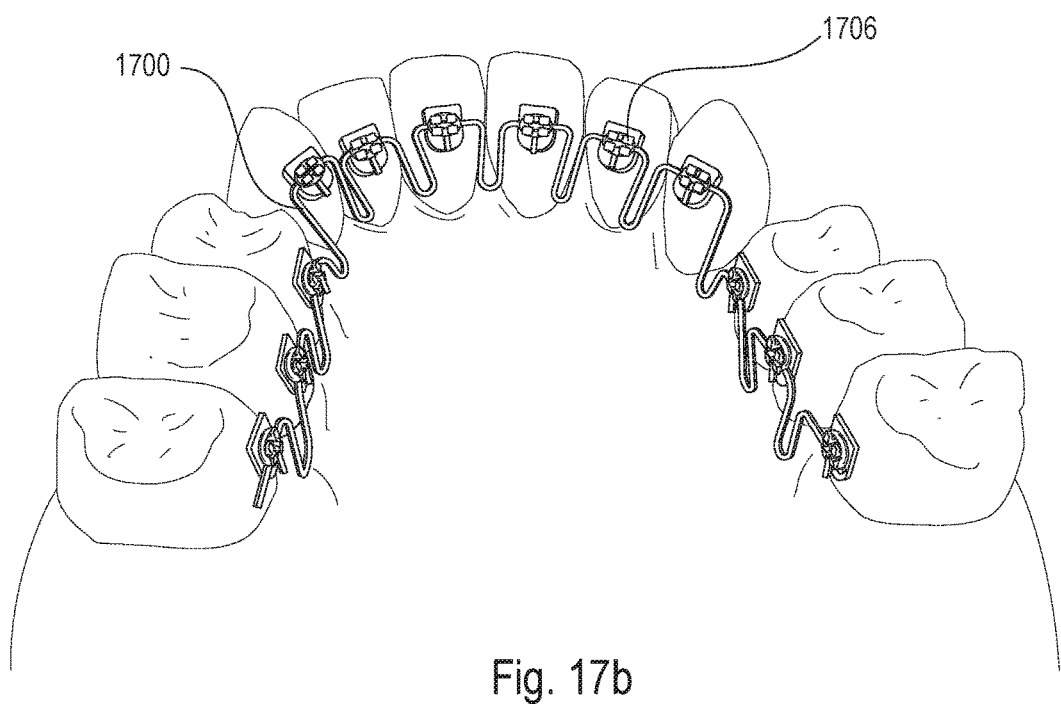
FIG. 17b is a perspective representation of the appliance of FIG. 17a, installed on teeth on which female connector elements are bonded.

The appliance 1700 in FIG. 17a includes male connector elements 1702 formed as relatively simple, linear members that are configured to engage and secure to female connector elements 1706 as shown in FIG. 17b. Each female connector element 1706 includes a linear slot feature, that receives a respective linear member of a male connector element 1702, as shown in FIG. 17b. In particular examples, the female connector element 1706 may be a twin bracket type connector.

Each male connector element 1702 is separated from each adjacent male connector element 1702 by a spring member 1704. In other examples, one or more male connector elements may be separated from one or two (or more) adjacent male connector elements by a rigid portion of the appliance that is devoid of a spring member. In the example shown in FIG. 17a, each spring member 1704 has a generally U shape structure, as described herein. In other examples, one or more (or each) spring member 1704 may have another suitable shape such as, but not limited to the other spring shapes shown and described herein or other shapes that can be cut from a flat sheet of material and bent into a 3D shape. In other examples, an appliance 1700 of FIG. 17a may include other types of male connector elements (such as, but not limited to those described herein in connection with FIGS. 1-3, 5, 6, 8-12h, 15a, 16a, 17a, 18c-18f, 25, 27a and 27b) or other types of spring members including but not limited to those described herein (or both). The shapes and types of spring members may be selected and configured, for example, to provide a desired movement and may be based at least in part on the type and size of the teeth to which the spring is to be connected.

Second Embodiment

As discussed above, systems or methods according to examples of a second embodiment include or employ an appliance that has a plurality of separate arms configured to connect to a corresponding plurality of the patient's teeth, where each arm of the appliance is configured to connect to a different respective tooth relative to each other arm of the appliance. In further examples of the second embodiment, the appliance may include one arm configured to connect to a plurality of teeth, or multiple separate arms configured to connect to a corresponding one of the patient's teeth, or various combinations of arm-to-tooth connections as described herein. In certain examples, an appliance according to the second embodiment may be made, after rearranging a 3D digital OTA to a 3D digital FTA, and designing (via computer aided design or other suitable design techniques) an appliance shape that is configured to impart forces on the patient's teeth to move the teeth from the OTA to the FTA (or to an ITA, or from an ITA to an FTA or another ITA).

Examples of appliances 800, 900, 1000 and 1100 according to the second embodiment are shown in FIGS. 8-11, respectively. The appliances 800, 900, 1000 and 1100 (and components of the appliances) may be made of any suitable material including, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in single structure.

Figure 8:
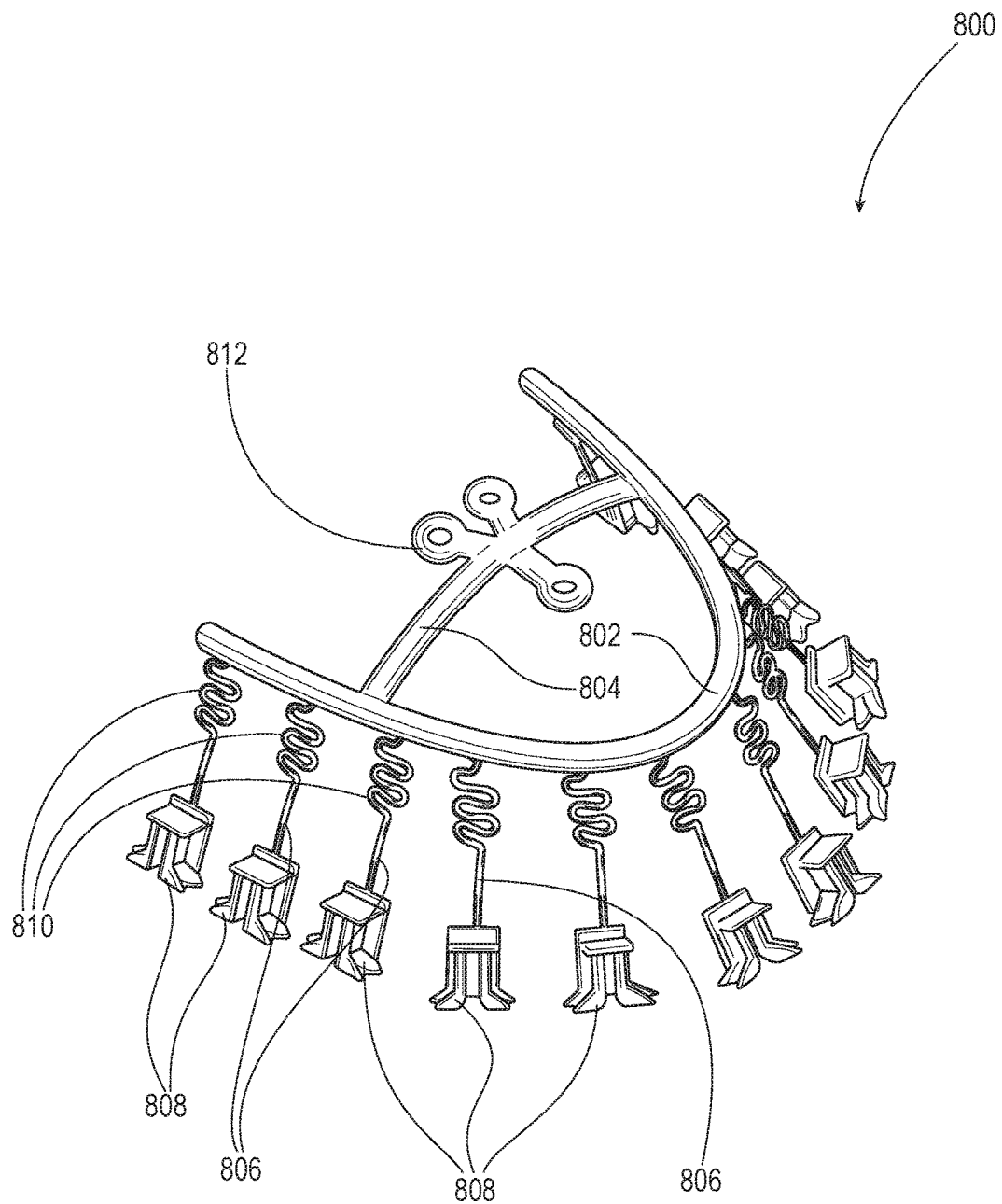
FIG. 8 is a perspective representation of an appliance according to an example of a second embodiment.
Figure 9:
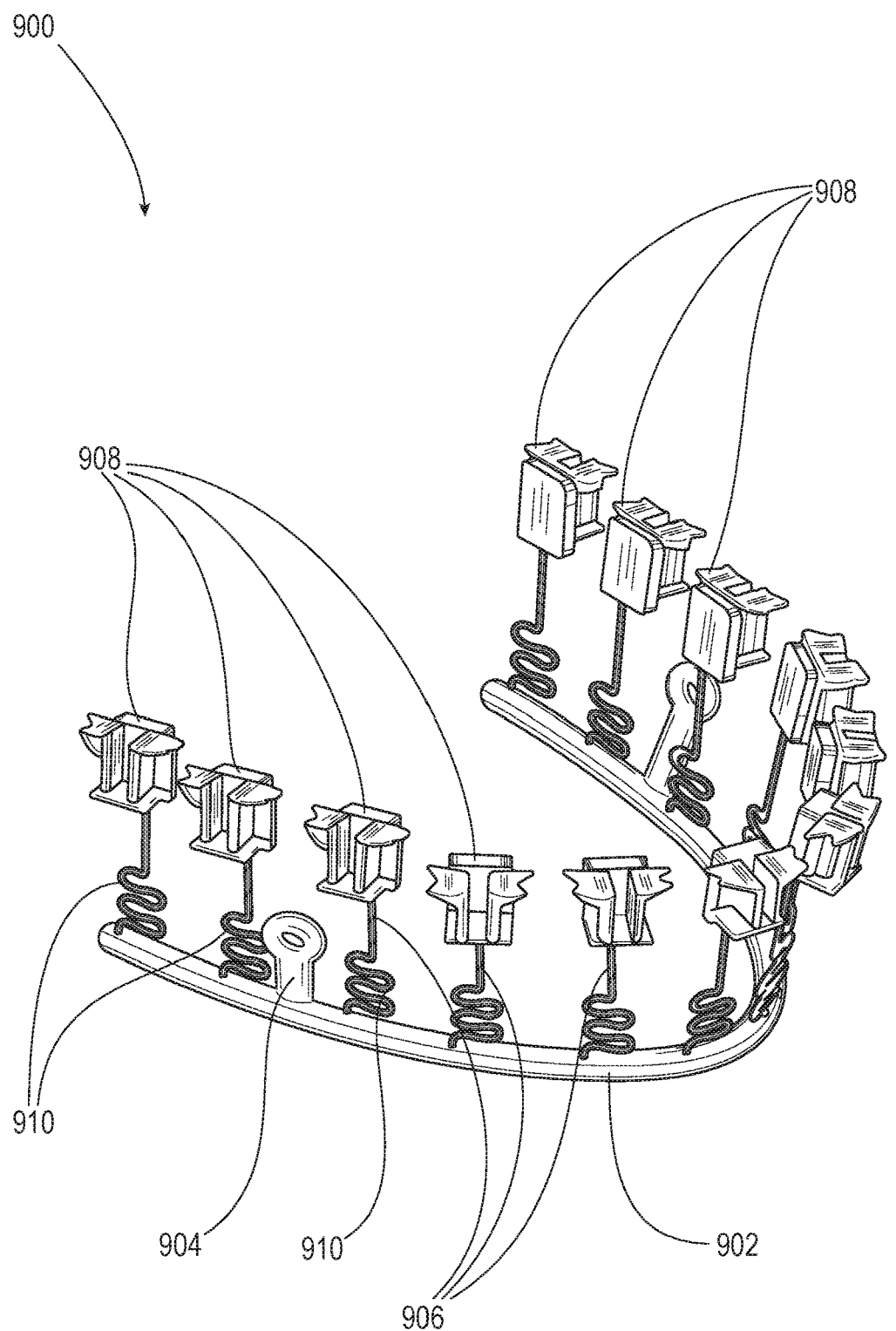
FIG. 9 is a perspective representation of an appliance according to another example of the second embodiment.
Figure 10:
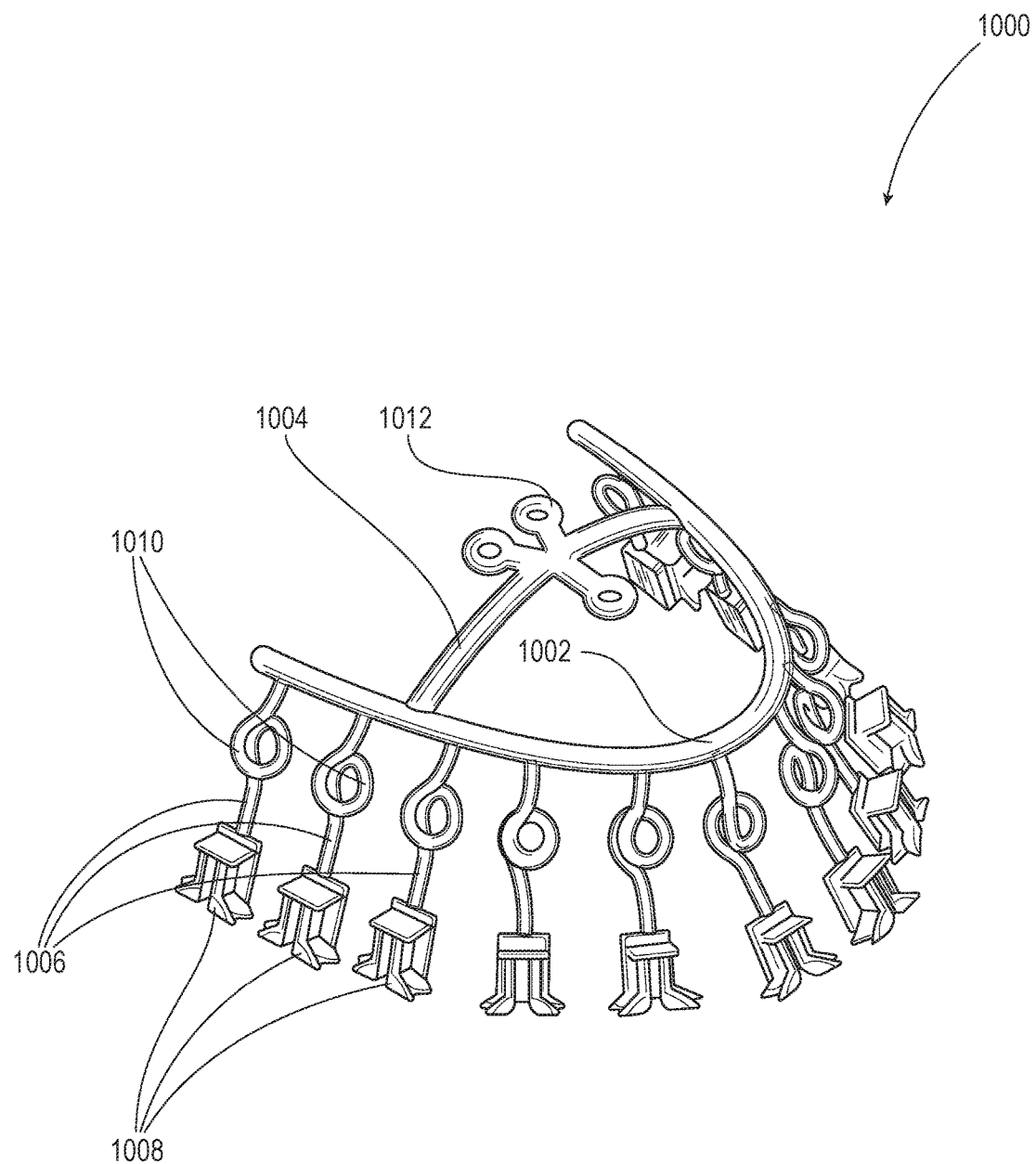
FIG. 10 is a perspective representation of an appliance according to another example of the second embodiment.

Each of the appliances 800 and 1000 in FIGS. 8 and 10 may be configured to be installed on an upper jaw of a patient. In particular examples, the appliance 800 or 1000 may be configured to help close an extraction space after the patient's first premolars are extracted or to adjust other teeth positions (or both). On the other hand, each of the appliances 900 and 1100 in FIGS. 9 and 11 may be configured to be installed on the lower jaw of a patient.

In FIGS. 8 and 10, the example appliances 800 and 1000 each include an arch-shaped bar 802 or 1002 that is configured for an upper jaw (to follow the arch of the upper jaw of a patient). The appliances 800 and 1000 each include a palatal arch feature 804 or 1004. In other examples, the palatal arch feature 804 or 1004 may be omitted.

Each of the appliances 800 and 1000 includes a plurality of separate arms (arms 806 in FIGS. 8 and 1006 in FIG. 10). The examples shown in FIGS. 8 and 10 include twelve arms 806 or 1006, that secure to twelve associated teeth, separately and individually, on a one-to-one basis. In other examples, the appliance may have other suitable numbers of arms, including fewer or greater than twelve arms. The number of arms may equal the number of teeth in the jaw that are to be moved.

Each of the arms 806 on the appliance 800 (and each of the arms 1006 on the appliance 1000) may have the same configuration (length, shape, width, etc.) as each of other arms of the appliance, as shown in FIGS. 8 and 10. Alternatively, some (or each) of the arms 806 of the appliance 800 (or of the arms 1006 of appliance 1000) may have a different configuration (length, shape, width, etc.) than some or each of the other arms of that appliance. In particular examples, the configuration, including the shape and size of each arm can depend upon the desired movement and size of the tooth to which the arm is to secure (and may differ for different arms and teeth).

Each arm 806 (or 1006) has one end extending from or otherwise connected to the bar 802 (or 1002) and a second end on which a male connector element 808 (or 1008) is formed or otherwise connected. Accordingly, a separate respective male connector element is formed on or otherwise connected to each separate respective arm. Each male connector element 808 is configured to engage with a respective female connector element or bracket, when the appliance 800 (or 1000) is installed on a patient's teeth. In particular examples, the male connector elements are configured to secure to the female connector elements bonded to a patient's teeth, and remain fixed on a patient's teeth, until a clinician removes the appliance.

Each arm 806 (or 1006) has a spring member 810 (or 1010) along its length. In the examples of FIGS. 8 and 10, the spring members 810 and 1010 are located at an end portion of the respective arms 806 and 1006 (i.e., the end portion corresponding to the arm end that extend from or is otherwise connected to the bar 802 or 1002, and opposite the arm end on which the male connector element 808 or 1008 is located). However, in other examples, the spring member 810 (or 1010) may be located at another location along the length of the arm 806 (or 1006), such as, but not limited to the middle of the length of the arm 806 (or 1006) or toward the arm end at which the male connector element 808 or 1008 is located.

The spring members 810 and 1010 may have any suitable configuration and may be designed and manufactured to provide a force or torque (or both) in the desired direction or magnitude (or both). In particular examples, computer aided design and manufacturing techniques may be employed to design or configure (or both) the spring members. The spring members 810 and 1010 may have the same configuration on each of the arms of the appliance, as shown in FIGS. 8 and 10. Alternatively, the spring members on some (or each) of the arms 806 of the appliance 800 (or of the arms 1006 of appliance 1000) may include a different configuration than some or each of the other arms of that appliance. The spring members 810 (or 1010) may be formed as a single unitarily formed structure with the rest of the arms 806 (or 1006), as shown in FIGS. 8 and 10. Alternatively, the spring members 810 (or 1010) may be formed separately from the rest of the arms 806 (or 1006) and then coupled to the arms 806 (or 1006) after they are formed.

Each spring member 810 in the example appliance 800 of FIG. 8 is configured with a plurality of U shaped segments along a portion of the length of its associated arm 806. In other examples, each spring member may include a single (no more than one) U shaped segment, or fewer or greater U shaped segments than shown in the example of FIG. 8.

Each spring member 1010 in the example appliance 1000 of FIG. 10 is configured with a spiral or loop shaped segment forming a single loop along a portion of the length of its associated arm 1006. In other examples, each spring member 1010 may include a plurality of loops along one or more segments of the length of its associated arm 1006. In other examples, other suitable spring configurations may be employed on one or more (or each) of the arms 806 or 1006. In other examples, more than one spring member (having the same or different configurations) may be included in each arm 806 or 1006. Geometries (size, shape, length, etc.) of the spring members and arms may be designed and selected, depending and based on various factors including, but not limited to the type or size of the tooth, facial morphology, the type of malocclusion to be addressed and other factors specific to each patient.

As described above, the example appliances 800 and 1000 shown in FIGS. 8 and 10 include a palatal arch feature (804 in FIGS. 8 and 1004 in FIG. 10). In the examples shown in FIGS. 8 and 10, the palatal arch features 804 and 1004, each include a plurality of holders 812 or 1012 for a corresponding plurality of anchorage devices, such as, but not limited to screws or other temporary anchorage devices (TADs). Three anchorage device holders 812 or 1012 are shown in each of FIGS. 8 and 10. In other examples, one, two or more than three anchorage device holders 812 or 1012 may be included on the palatal arch feature 804 or 1004. In other examples, one or more anchorage device holders may be provided at other suitable locations on the appliance. In yet other examples, the anchorage device holders 812 and 1012 may be omitted from the palatal arch features 804 and 1004. In particular examples, the inclusion, number and location of anchorage device holders 812 and 1012 may depend, at least in part, upon the type of malocclusion to be addressed and other factors specific to each patient.

One or more anchorage device holders 812 and 1012 may be employed to receive or otherwise hold a TAD or other anchorage device that is secured to a patient's palate. Thus, if a clinician desires additional anchorage of the appliance, the clinician may decide to use one or more TAD(s). For example, before or after male connector elements 808 (or 1008) of an appliance 800 (or 1000) are secured to female connector elements previously bonded to a patient's teeth, a clinician may secure one or more implantable screws or other TAD structures to one or more anchorage device holders 812 (or 1012) and to the patient's palate. In the examples of FIGS. 8 and 10, the anchorage device holders 810 and 1010 have a ring or annular shape with a central opening through which a length of a screw or other suitable TAD structure may extend, to anchor the appliance to a patient's palate, when the screw or other TAD structure is implanted in the patient's palate. The clinician may anesthetize the area of the patient's palate to which the TADs will be implanted, prior to implantation.

Figure 11:
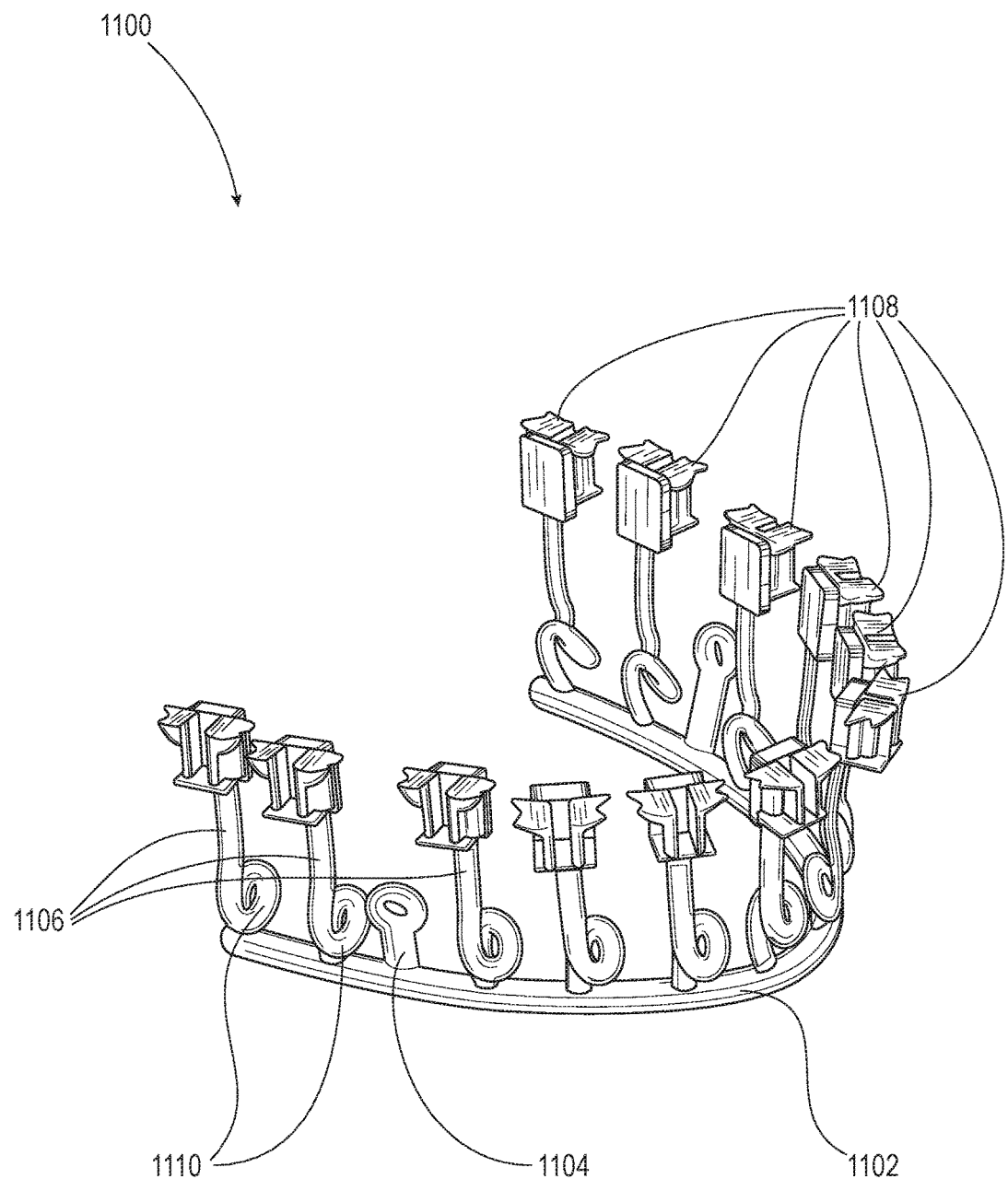
FIG. 11 is a perspective representation of an appliance according to another example of the second embodiment.

In FIGS. 9 and 11, the example appliances 900 and 1100 each include an arch-shaped bar 902 or 1102 that is configured for a lower jaw (to follow the arch of the lower jaw of a patient). The appliances 900 and 1100 in FIGS. 9 and 11 do not include a lingual arch support feature. However other examples may include a lingual arch support feature (for example, but not limited to a feature similar to the feature 302 in FIG. 3).

Each of the appliances 900 and 1100 includes two anchorage device holders 904 or 1104 extending from the arch-shaped bar 902 or 1102, on the right and left sides of the appliance. Each anchorage device holder 904 or 1104 is configured to receive and hold a suitable anchorage device such as, but not limited to an implantable screw or other suitable TAD structure, for securing the appliance to the lingual side of the lower jaw.

While two anchorage device holders 904 or 1104 are shown in each of FIGS. 9 and 11, in other examples, one or more than two anchorage device holders 904 or 1104 may be included on the appliance 900 or 110. In yet other examples, the anchorage device holders 904 and 1104 may be omitted from the appliances 900 or 1100. In particular examples, the inclusion, number, type and location of anchorage device holders 904 and 1104 may depend, at least in part, upon the type of malocclusion to be addressed and other factors specific to each patient. Each anchorage device holder 904 or 1104 is arranged on the lingual side of the appliance, for receiving an anchorage device, such as a TAD, secured to a lingual side of the patient's lower jaw, but otherwise may have a configuration and operate as described herein with respect to anchorage device holders 812 or 1012. In other examples, the anchorage device holders may be arranged on the buccal side of the patient's jaw. In other examples, other suitable mechanisms or combinations of mechanisms may be employed for securing the appliance to the patient's jaw.

Each of the example appliances 900 and 1100 in FIGS. 9 and 11 includes a plurality of arms 906 or 1106 with spring members 910 or 1110. Each of the example appliances 900 and 1100 also includes a respective male connector element 908 or 1108 on one end of each respective arm 906 or 1106. The arms 906 and 1106, spring members 910 and 1110 and male connector elements 908 and 1108 may have a configuration and operate similar to the arms 806 and 1006, spring members 810 and 1010, and male connector elements 808 and 1008 described herein, but for teeth on the lower jaw of a patient.

As discussed above, each male connector element 808, 908, 1008 and 1108 is configured to engaged with a respective female connector element or bracket, when the appliance 800, 900, 1000 or 1100) is installed on a patient's teeth. In the appliance examples shown in FIGS. 8-11, each male connector element 808, 908, 1008 and 1108 may be configured as a single, unitarily formed structure either formed separately from the arm to which it is connected, or formed unitarily with that arm. Such unitarily formed structures may be formed by any suitable manufacturing techniques including, but not limited to molding, casting, machining, 3D printing, stamping, cutting, extruding, or the like. In certain examples, each male connector element is formed as a unitary structure with other portions of the appliance by cutting a 2D shaped member from a sheet of suitable material such as, but not limited to Nitinol (NiTi), stainless steel, beta-titanium, cobalt chrome or other metal alloy, polymers or ceramics, and bending the 2D shaped member into a 3D shaped member of the appliance. In other examples, one or more (or each) male connector element 808, 908, 1008 and 1108 may be formed as multiple separate components that are connected together with an arm, to form an arm and male connection structure of an appliance 800, 900, 1000 or 1100.

An example of a male connector element and arm structure configured from multiple components that connect together and that connect to an arch-shaped bar of an appliance is described with respect to FIGS. 12a-h. The example shown in FIGS. 12a-h provides a male connector element having a configuration as shown in example appliances 800, 900,1000 and 1100, in FIGS. 8-11. However, male connector elements as shown in FIGS. 12a-h may be employed on other appliances as described herein, including, but not limited to the appliances 100, 200, 300, 500 and 600 of FIGS. 1-3, 5 and 6.

Figure 12A:
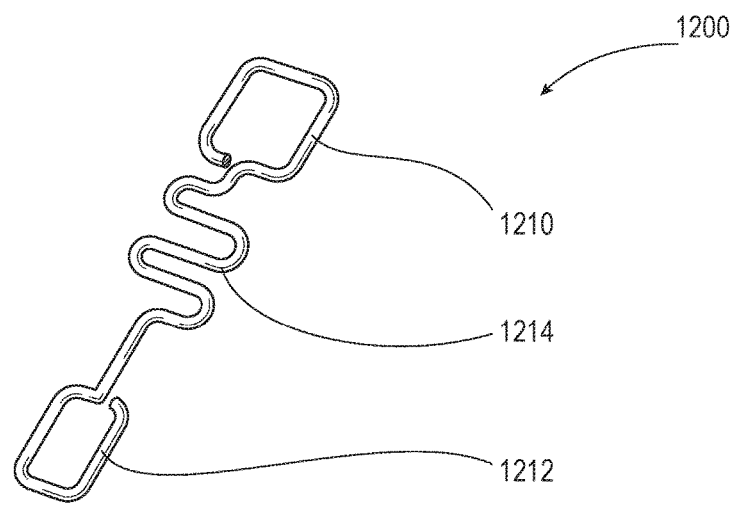
FIGS. 12a-h are perspective representations of components of a male connector element and arm for an appliance according to another example of the second embodiment.
Figure 12B:
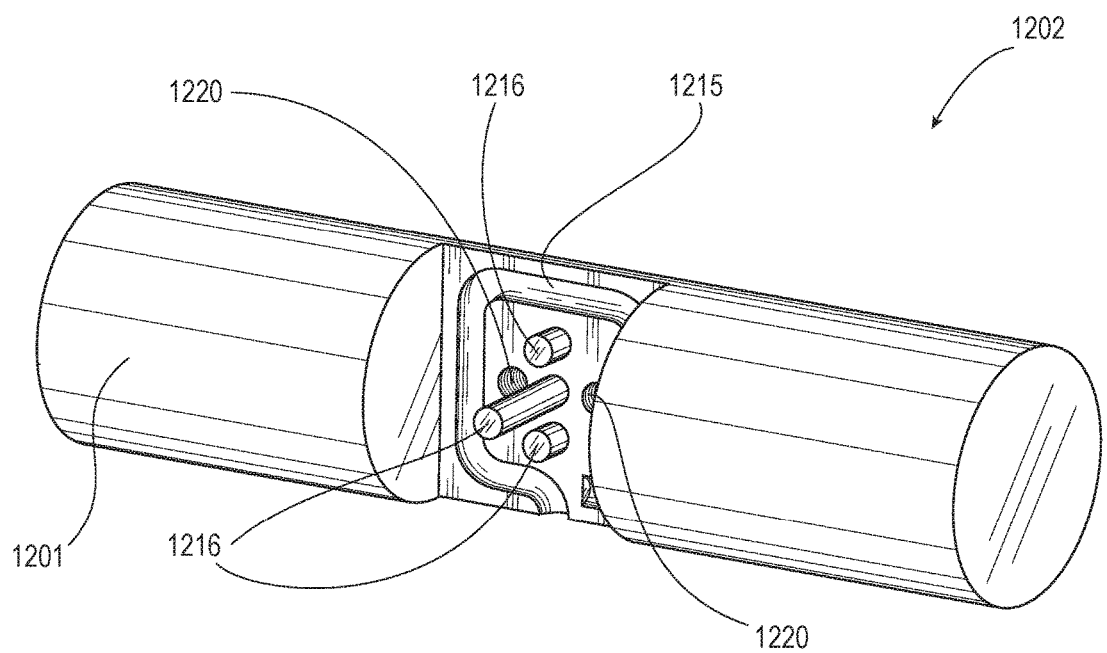
Figure 12C:
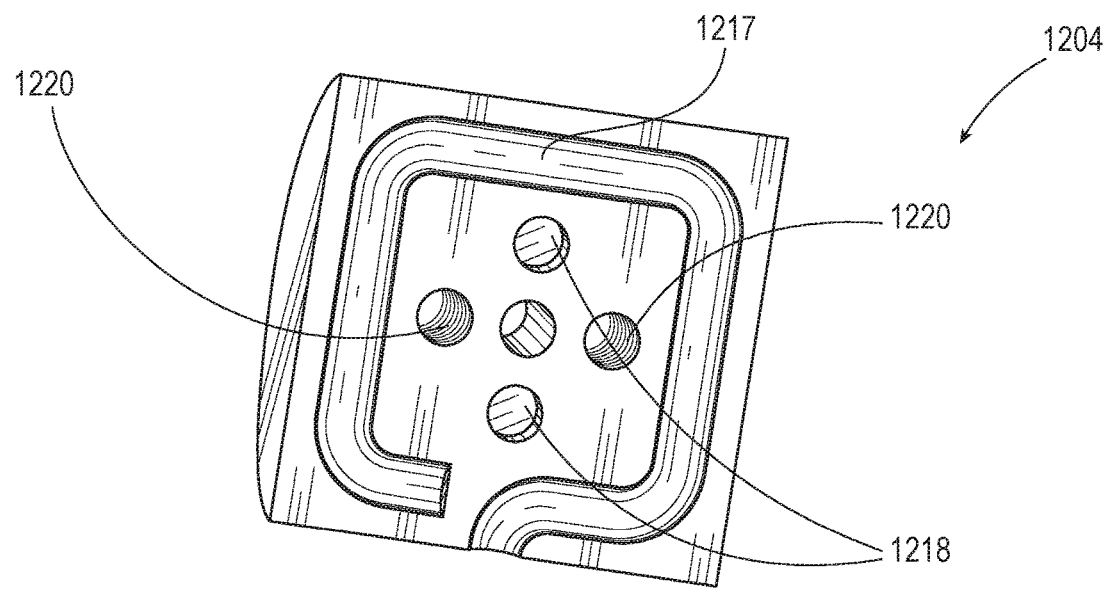
Figure 12D:
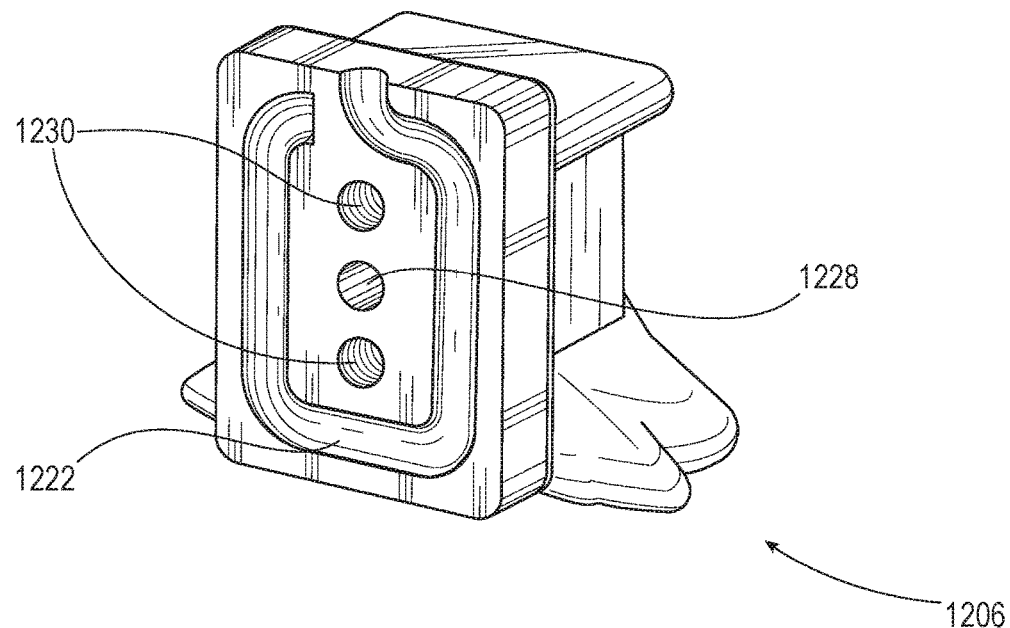
Figure 12E:
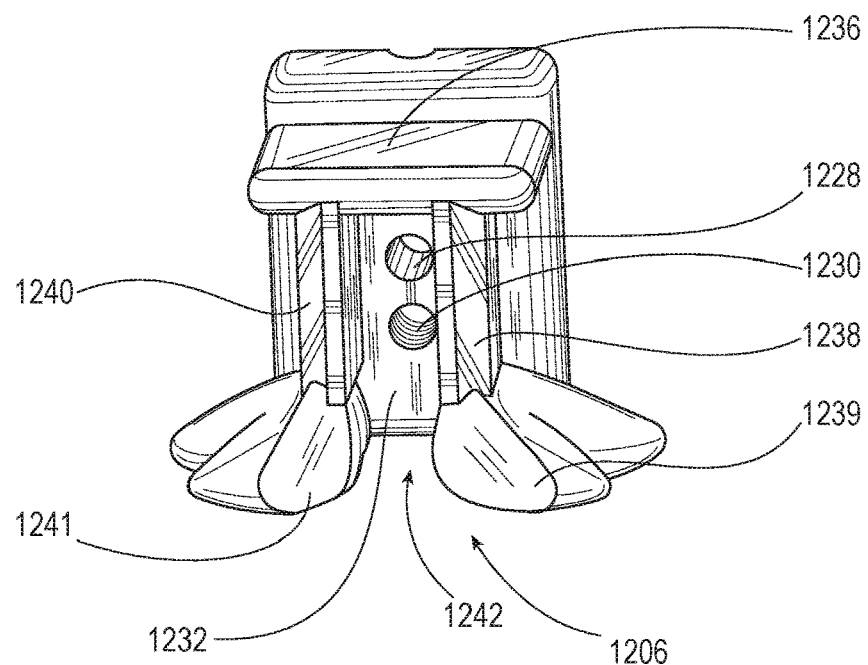
Figure 12F:
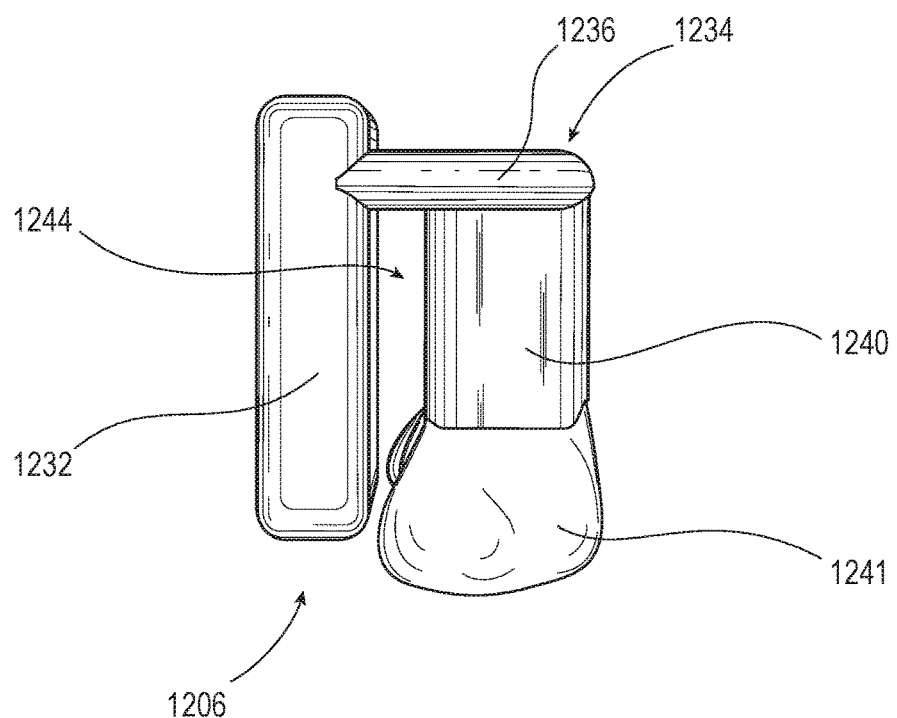
Figure 12G:
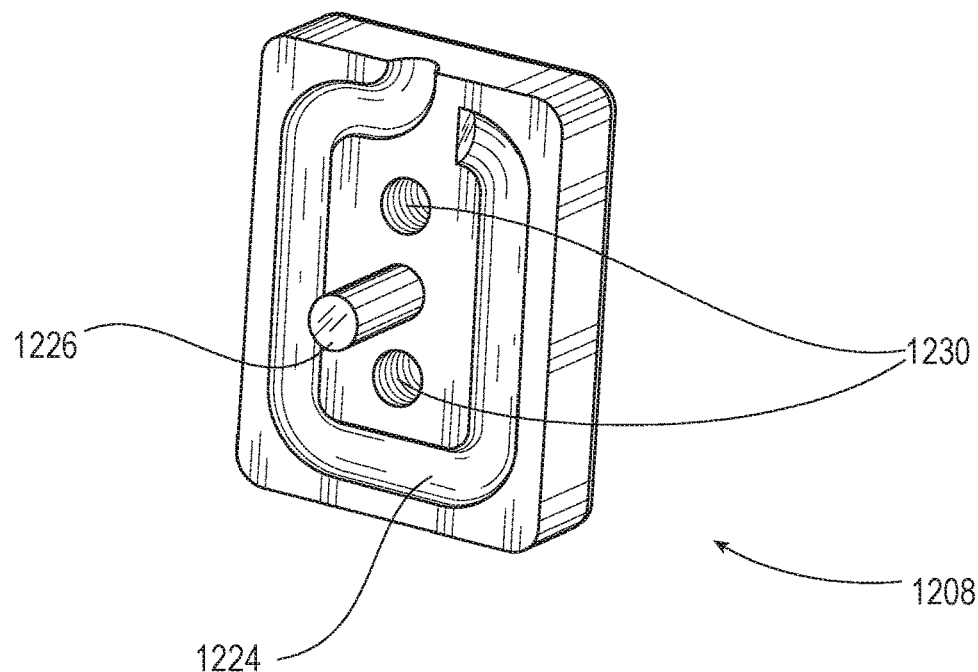
Figure 12H:
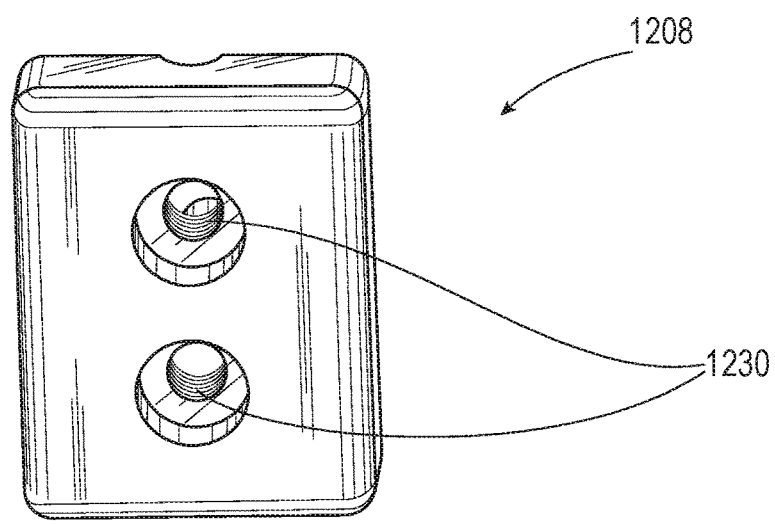

The example shown in FIGS. 12a-h includes an arm structure 1200 (shown in FIG. 12a), an arch-shaped structure or bar 1201 having one or more (multiple in the illustrated example) first arm connector components 1202 (shown in FIG. 12b), second arm connector components 1204 (shown in FIG. 12c), a first male connecter element component 1206 (shown in rear, front and side views in FIGS. 12d, 12e and 12f, respectively), and a second male connector element component 1208 (shown in rear and front views in FIGS. 12g and 12h, respectively). In particular examples, the arm structure 1200 may correspond to any one or more of the arms 806, 906, 1006, 1106 of the appliances 800, 900, 1000 and 1100 described herein. The arm structure 1200 includes a first end section 1210 configured to attach to a bar (such as, but not limited to bar 802, 902, 1002 or 1102 of an appliance 800, 900, 1000 or 1100). In the example shown in FIG. 12a, the first end section 1210 of the arm structure 1200 is formed in a loop shape section that fits within a corresponding loop-shaped groove in one or both of the first and second arm connector components 1202 and 1204 (shown in FIGS. 12b and 12c).

In addition, the arm structure 1200 includes a second end section 1212 configured to attach a male connector element. In the example shown in FIG. 12a, the second end section 1212 of the arm structure 1200 is formed in a loop shape section that fits within a corresponding loop-shaped groove in one or both of the first and second male connector element components 1206 and 1208 (shown in FIGS. 12d-12h). The arm structure 1200 also includes a central section 1214 between the first and send end sections. One or more spring members (such as, but not limited to spring members as described herein) may be formed or otherwise provided on the central section 1214.

The first and second arm connector components 1202 and 1204 shown in FIGS. 12b and 12c are configured to connect together. Each first arm connector component 1202 may be formed as part of (integral with) the arch-shaped structure or bar 1201 of the appliance, as shown in FIG. 12b. In other examples, each first arm connector component 1202 may be formed separate from the arch-shaped structure or bar and then attached to the arch-shaped structure or bar by adhesive, weld or any other suitable attachment mechanism, to form the structure shown in FIG. 12*b*. The arch-shaped structure or bar 1201 may correspond to the arch-shaped structures 802, 902, 1002, 1102 described herein with reference to examples in FIGS. 8-11, or other suitable example as described herein.

One or both of the first and second arm connector components 1202 and 1204 includes a groove 1215 and 1217 for receiving the first end 1210 of the arm structure 1200 between the first and second arm connector components 1202 and 1204. More specifically, the first end section 1210 of the arm structure 1200 is placed between the first and second arm connector components 1202 or 1204 and the arm connector components 1202 and 1204 are then brought together to enclose the first end 1210 of the arm structure 1200 within the grooves 1215 and 1217. The grooves 1215 and 1217 extend to an edge of the respective first and second arm connector components 1202 and 1204, such that the central section 1214 of the arm structure 1200 may extend out from the connector components 1202 and 1204, when the connector components 1202 and 1204 are coupled together.

One of the first and second arm connector components 1202 and 1204 (e.g., connector component 1202) includes one or more (three in FIG. 12*b*) protrusions 1216 that engage a corresponding one or more recesses or apertures 1218 in the other of the first and second arm connector components 1202 and 1204 (e.g., connector component 1204). The protrusions 1216, recesses and apertures 1218 help to align the first and second arm connector components 1202 and 1204 together in proper alignment with each other and the arm structure 1200, during assembly. In addition, the protrusions 1216, recesses and apertures 1218 may be configured to provide a snap fit or friction fit connection between the first and second arm connector components 1202 and 1204. In further examples, alternative or additional connection mechanisms, including, but not limited to screws, adhesives, welding or the like, may be employed to connect the connector components 1202 and 1204 together. For example, one or both of the first and second arm connector components 1202 and 1204 may include one or more apertures 1220 for receiving one or more screw, bolt or other threaded connector (not shown). In such examples, one or more of the apertures may be threaded, for threading engagement with the screw, bolt or other threaded connector (not shown).

The first and second male connector element components 1206 and 1208 shown in FIGS. 12*d*-12*h* are configured to connect together. One or both of the first and second male connector element components 1206 and 1208 includes a groove 1222 and 1224 for receiving the second end 1212 of the arm structure 1200 between the first and second male connector element components 1206 and 1208. More specifically, the second end section 1212 of the arm structure 1200 is placed between the first and second male connector element components 1206 or 1208 and the male connector element components 1206 and 1208 are then brought together to enclose the second end 1212 of the arm structure 1200 within the grooves 1222 and 1224. The grooves 1222 and 1224 extend to an edge of the respective first and second male connector element components 1206 and 1208, such that the central section 1214 of the arm structure 1200 may extend out from the male connector element components 1206 and 1208, when the connector components 1206 and 1208 are coupled together.

One of the first and second male connector element components 1206 and 1208 (e.g., connector component 1208) includes one or more (one in FIG. 12*g*) protrusions 1226 that engage a corresponding one or more recesses or apertures 1228 in the other of the first and second male connector element components 1206 and 1208 (e.g., connector component 1206). The protrusions 1226, recesses or apertures 1228 help to align the first and second male connector element components 1206 and 1208 together in proper alignment with each other and the arm structure 1200, during assembly. In addition, the protrusions 1226, recesses or apertures 1228 may be configured to provide a snap fit or friction fit connection between the first and second male connector element components 1206 and 1208. In further examples, alternative or additional connection mechanisms, including, but not limited to screws, adhesives, welding or the like, may be employed to connect the male connector element components 1206 and 1208 together. For example, one or both of the first and second male connector element components 1206 and 1208 may include one or more apertures 1230 for receiving one or more screw, bolt or other threaded connector (not shown). In such examples, one or more of the apertures may be threaded, for threading engagement with the screw, bolt or other threaded connector (not shown).

Accordingly, the first and second male connector element components 1206 and 1208 may be assembled and connected to one end of the arm structure 1200. The other end of the arm structure 1200 may be assembled and connected to an arch-shaped bar of an appliance. In that example, an appliance 800, 900, 1000 or 1100 may be composed of multiple, separately formed components that are assembled and connected together to form a single, unitary appliance structure.

In such examples, each component of an appliance may be formed separately by any suitable manufacturing technique including, but not limited to molding, casting, machining, 3D printing, stamping, extruding, cutting and bending (e.g., cutting a 2D shaped member from a sheet and bending the 2D shaped member into a 3D shaped member as described herein) or the like, and then assembled with one or more of the other components of the appliance. In such examples, arm structures 1200 may be formed by any suitable technique including, but not limited to those discussed above, or by bending techniques. For example, an automated or robot-controlled bending technique may be employed to form or bend desired and precise spring and arm configurations from suitable materials such as, but not limited to Nitinol (NiTi), stainless steel, beta-titanium, cobalt chrome or other metal alloy, polymers or ceramics. In other examples, one or more (or all) of the components of the appliance structure may be formed together, as a single, unitarily formed structure.

As discussed above, the example shown in FIGS. 12*a-h* provides a male connector element having a configuration as shown in example appliances 800, 900,1000 and 1100, in FIGS. 8-11. Such male connector elements are configured to engage and secure to female connector elements having a configuration, for example, as shown in FIGS. 13*a* and 13*b*.

For example, as best shown in FIGS. 12*e* and 12*f*, the male connector component 1206 includes a backing portion 1232 (the portion that includes the apertures 1228 and 1230 and an extension structure 1234. The extension structure 1234 is configured to engage a female connection element, for example, of the type shown in FIGS. 13a and 13b. The extension structure 1234 includes a shelf-shaped extension 1236 that extends outward from the backing portion 1232. The extension structure 1234 also includes a pair of leg members 1238 and 1240 that extend from the shelf-shaped extension 1236 and are spaced apart from each other by a gap 1242. As shown in FIG. 12f, the leg members 1238 and 1240 are also spaced apart from the backing portion 1232 by a gap 1244, by a portion of the extended length of the shelf-shaped extension 1236. The free end of each leg member 1238 and 1240 has a flared or widened portion 1239 and 1241, respectively. The male connector component 1206 may be made of any suitable material such as, but not limited to nitinol, stainless steel, beta-titanium, cobalt chrome or other metal alloy, polymers or ceramics, or other material that allows the leg members 1238 and 1240 to be resiliently flexible and flex inward, when a force is applied (directed toward pressing the leg members 1238 and 1240 toward each other) to reduce the width of the extension structure 1234. In that state, the extension structure may be inserted into a female connector element, for example, of the type shown in FIGS. 13a and 13b. Once inserted into the female connector element, the force may be released, to allow the leg members 1238 and 1240 to resiliently move outward toward their original position, to secure the male connector element (formed by components 1206 and 1208) to the female connector element. In particular examples, the male connector component 1206 (including the shelf-shaped extension structure 1234 and leg members 1240 and 1238 are formed as an integral unitarily formed structure. In other examples, the male connector component 1206 may be formed of multiple separate components connected together.

Figure 13A:
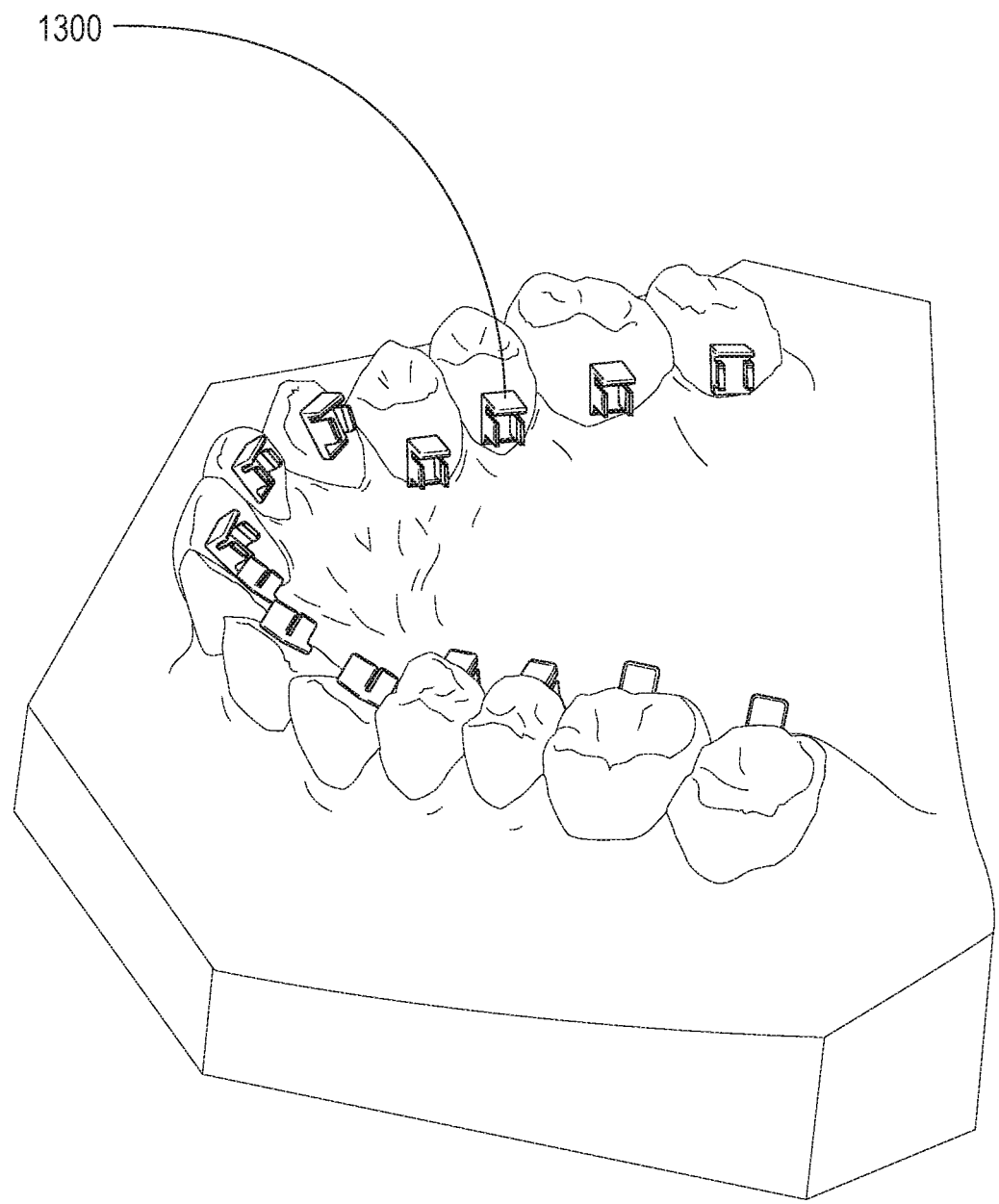
FIG. 13a is a perspective representation of an upper jaw having another example of female connector elements.
Figure 13B:
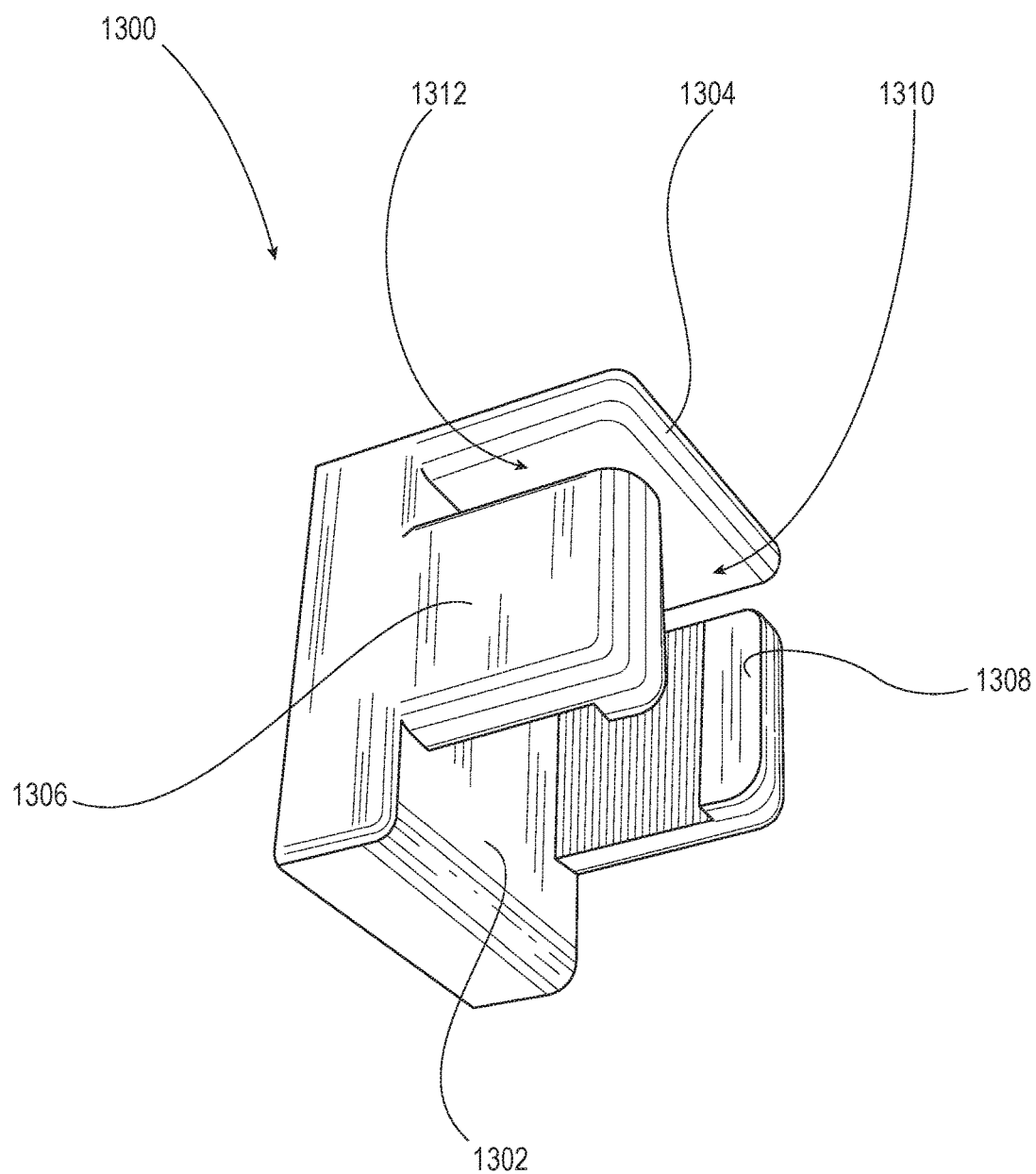

FIG. 13a shows a representation of an OTA image of an upper jaw of a patient, on which examples of female connector elements 1300 are attached to the lingual surface of the teeth, on the upper arch. In other examples, the female connector elements 1300 may be attached to the buccal surface of the teeth, for example, if preferred by the clinician. A separate, respective female connector element 1300 is secured to each respective tooth. The female connector elements provide a connection interface to connect one or more appliances to the teeth, according to the first and second embodiments described herein. While the drawing in FIG. 13a shows all of the teeth in each jaw as having female connector elements, other examples may employ separate, respective female connector elements on some, but not all of the teeth in the upper jaw or the lower jaw, for example, as selected by the clinician.

The female connector elements 1300 can be attached to the teeth via direct or indirect bonding, or other suitable means for fixedly securing the elements to a surface of the teeth. Bonding materials may include adhesives such as, but not limited to composite resin. In the case of indirect bonding, a clinician may use a jig to increase the accuracy of the bracket placement. In particular examples, one or more (or all) of the female connector elements 1300 are customized in size or shape to each tooth, and are configured to have the lowest profile possible (to minimize the size in the dimension extending away from the tooth, i.e., the buccolingual direction, or the mesiodistal or occlusoginival directions, or any combination thereof).

FIG. 13b shows an example of a female connector element 1300 in FIG. 13a. In the example of FIG. 13b, the female connector element 1300 includes a backing portion 1302 configured to be bonded to a surface of a patient's tooth. The female connector element 1300 in FIG. 13b also includes a shelf-shaped extension structure 1304 that extends outward from the backing portion 1302. The female connector element 1300 in FIG. 13b also includes first and second L shaped extension structures 1306 and 1308 that extends outward from the backing portion 1302. The extension structures 1304, 1306 and 1308 extend outward from the backing portion 1302 in the same direction. However, the shelf-shaped extension structure 1304 has a surface with a planar surface dimension extending in a direction (horizontal in FIG. 13b) that is perpendicular to a planar surface dimension of a surface of each of the L shaped extension structures. The extension structures 1304, 1306 and 1308 are arranged such that a gap 1310 is provided between the L shaped extension structures 1306 and 1308 and a further gap 1312 is provided between the shelf-shaped extension structure 1304 and each of the L shaped extension structures 1306 and 1308.

The female connector element 1300 may be made of any suitable material such as, but not limited to nitinol, stainless steel, beta-titanium, cobalt chrome or other metal alloy, polymers, ceramics, or other material that allows the L shaped extension structures 1306 and 1308 to be resiliently flexible and flex outward, when a force is applied (directed toward pressing the L shaped extension structures away from each other) to increase the width of gap 1310. In that state, the extension portion 1234 of the male connector element may be inserted into the gap 1310. Once inserted, the force may be released, to allow the L shaped extension structures 1306 and 1308 to resiliently move toward each other, toward their original position, to secure the male connector element to the female connector element. In particular examples, the shelf-shaped extension 1236 of the male connector component 1206 fits into the gap 1312 of the female connector element 1300, when the extension portion 1234 of the male connector element is received in the gap 1310. In other examples, the L shaped extension structures of the female connector element may be relatively rigid (and not configured to flex outward much or at all), such that the resilient flexibility of the leg members 1236 and 1238 of the male connector element is sufficient to allow the male connector element to be inserted into the gap 1310 without requiring the L shaped extension structures 1306 and 1308 of the female connector element to flex outward. In particular examples, the female connector element 1300 (including the shelf-shaped extension structure 1304 and L shaped extension structures 1306 and 1308) are formed as an integral unitarily formed structure. In other examples, the female connector element 1300 may be formed of multiple separate components connected together.

Each of the L shaped extension structures 1306 and 1308 of the female connector element 1300 includes a free end having a lip or L extension, extending toward the other of the L shaped extension structures. When the extension portion 1234 of the male connector element 1200 is received in the gaps 1310 and 1312 of the female connector element 1300, as described above, the lip or L extension of the L shaped extension structures 1306 and 1308 snap back over the leg members 1238 and 1240 of the male connector element 1200, to retain and secure the male connector element. The flared or widened portion 1239 and 1241 of the leg members 1238 and 1240 and the shelf-shaped extension 1236 help to maintain the male connector element 1200 in a properly aligned state in the female connector element 1300, when secured and during installation. In that state, the male connector element 1200 may remain secured to the female connector element 1300, until a clinician removes the male connector element (for example, by forcing the leg members 1236 and 1238 of the male connector element inward sufficient to clear the L shaped extension structures 1306 and 1308, and then pulling the male connector element away from the female connector element.

The male connector elements 808, 908, 1008 and 1108 in certain examples may be configured as described herein with respect to FIGS. 12a-12g, for engagement with female connection elements 1300 as described herein with respect to FIGS. 13a and 13b. However, in other examples, the male connector elements 808, 908, 1008 and 1108 according to a second embodiment may be similar to the male connector elements 104, 204, 304, 504 and 604 described herein with respect to the first embodiment. In such examples, female connector elements may be configured similar to female connector elements 700 in FIG. 7. Similarly, other examples of the first embodiment may include male connector elements as described with respect to FIGS. 12a-12g for engagement with female connection elements 1300 as described herein with respect to FIGS. 13a and 13b.

Figure 15A:
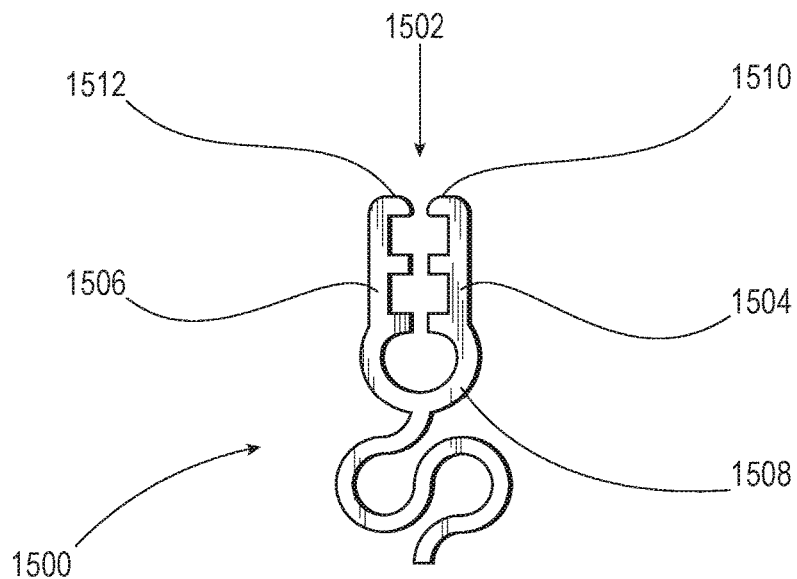
FIG. 15a is a plan view representation of an example of a male connector element.
Figure 15B:
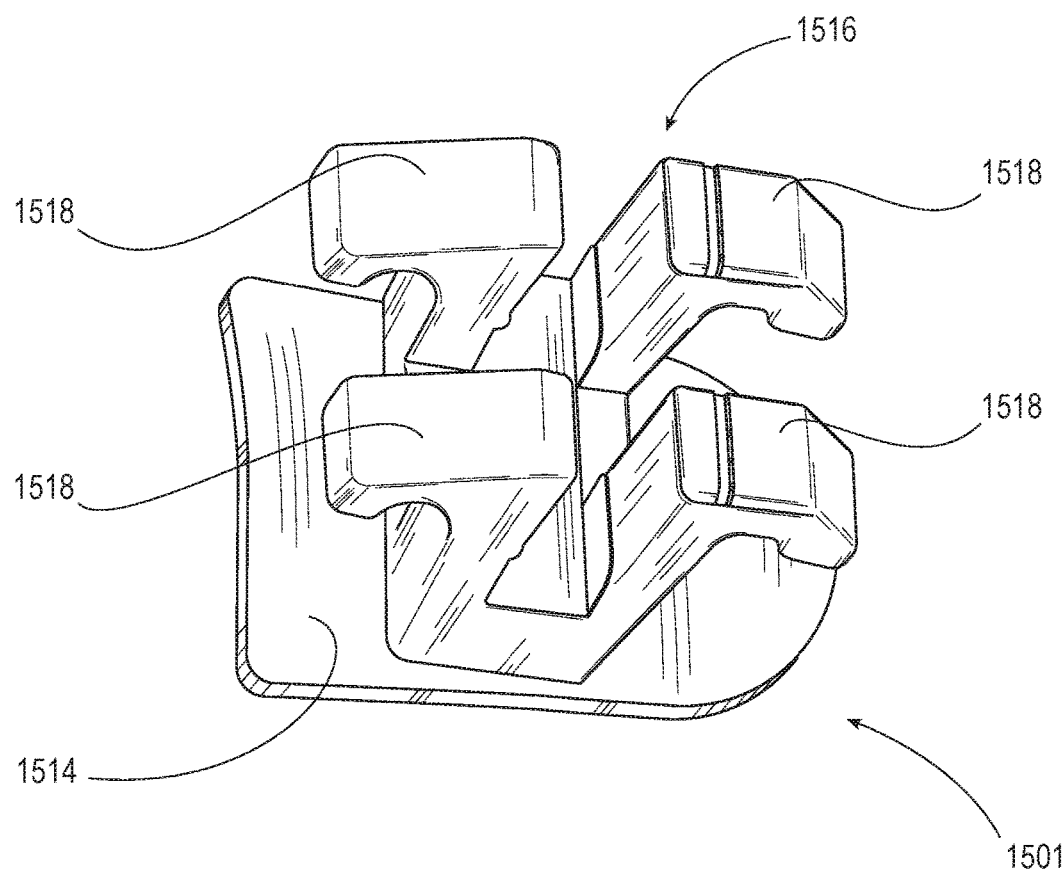
FIG. 15b is a perspective view representation of another example of a female connector element.
Figure 15C:
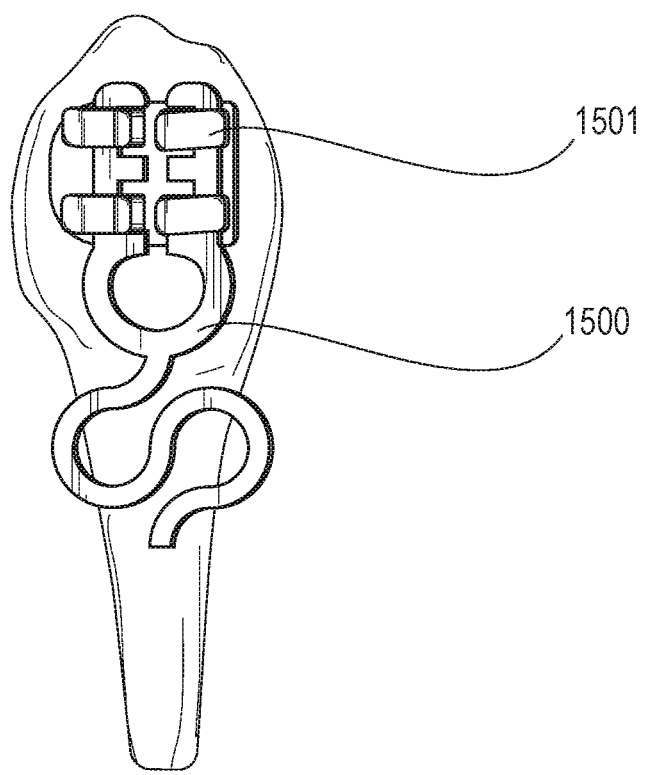
FIG. 15c is a perspective view representation of the male connector element of FIG. 15a coupled to the female connector element of FIG. 15b, bonded on a tooth.

In other examples, male connector elements on appliances according to a second embodiment (including appliances 800, 900, 1000 and 1100) or according to a first embodiment may have other suitable configurations such as, but not limited to the configurations of the male connector element examples shown in FIG. 15a, for engaging and securing to a female connector element 1501 as shown in FIGS. 15b, and 15c. The female connector element 1501 is shown as bonded on a tooth, in FIG. 15c.

The male connector element 1500 in FIG. 15a includes a shaped body portion having first and second arm sections 1504 and 1506. Each arm section 1504 and 1506 is connected to other arm section at a first end 1508, and extends to a free end 1510, 1512, respectively. The arm sections 1504 and 1506 are spaced apart from each other (except at the connected end 1508), to form a gap 1502 between the arm sections and extending along a portion of the length of each arm section. The male connector element is made of a sufficiently resilient material that allows the free ends of the arm sections 1504 and 1506 to be forced to move further apart or away from each other, and then resiliently move back to their original state when the force is removed. When the arm sections 1504 and 1506 are forced further apart from each other, the width dimension of the gap 1502 between the arm sections 1504 and 1506 increases. In that state, the male connector element 1500 is placed over the female connector element. When placed over the female connector element, the force on the arm sections 1504 and 1506 is released to allow the arm sections to resiliently move toward their un-forced or passive state, to lock or secure the male connector element to the female connector element.

The female connector element shown in FIG. 15b includes a backing portion 1514 configured to be bonded to a surface of a patient's tooth. An extension portion 1516 composed of four hook or L shaped extension members 1518 extends outward from the backing portion 1514. When the arm sections 1504 and 1506 of the male connector element 1500 are forced apart as described above, the male connector element 1500 may be placed over the female connector element, such that the hook shaped extension members 1518 are received in the gap 1502 between the arm sections 1504 and 1506, and the arm sections 1504 and 1506 are received in the female connector element, behind the hook or L shaped free end of the hook shaped extension members 1518. In that state, the force on the arm sections 1504 and 1506 is released to allow the arm sections to resiliently move toward their un-forced or passive state, to lock or secure the arm sections 1504 and 1506 between the backing portion 1514 and the hook or L shaped free end of the hook shaped extension members 1518 of the female connector element 1501, as shown in FIG. 15c. In that state, the male connector element 1500 may remain secured to the female connector element 1501, until a clinician removes the male connector element (for example, by forcing the arm sections 1504 and 1506 outward sufficient to clear the hook or L shaped free end of the hook shaped extension members 1518, and then pulling the male connector element away from the female connector element.

Figure 16A:
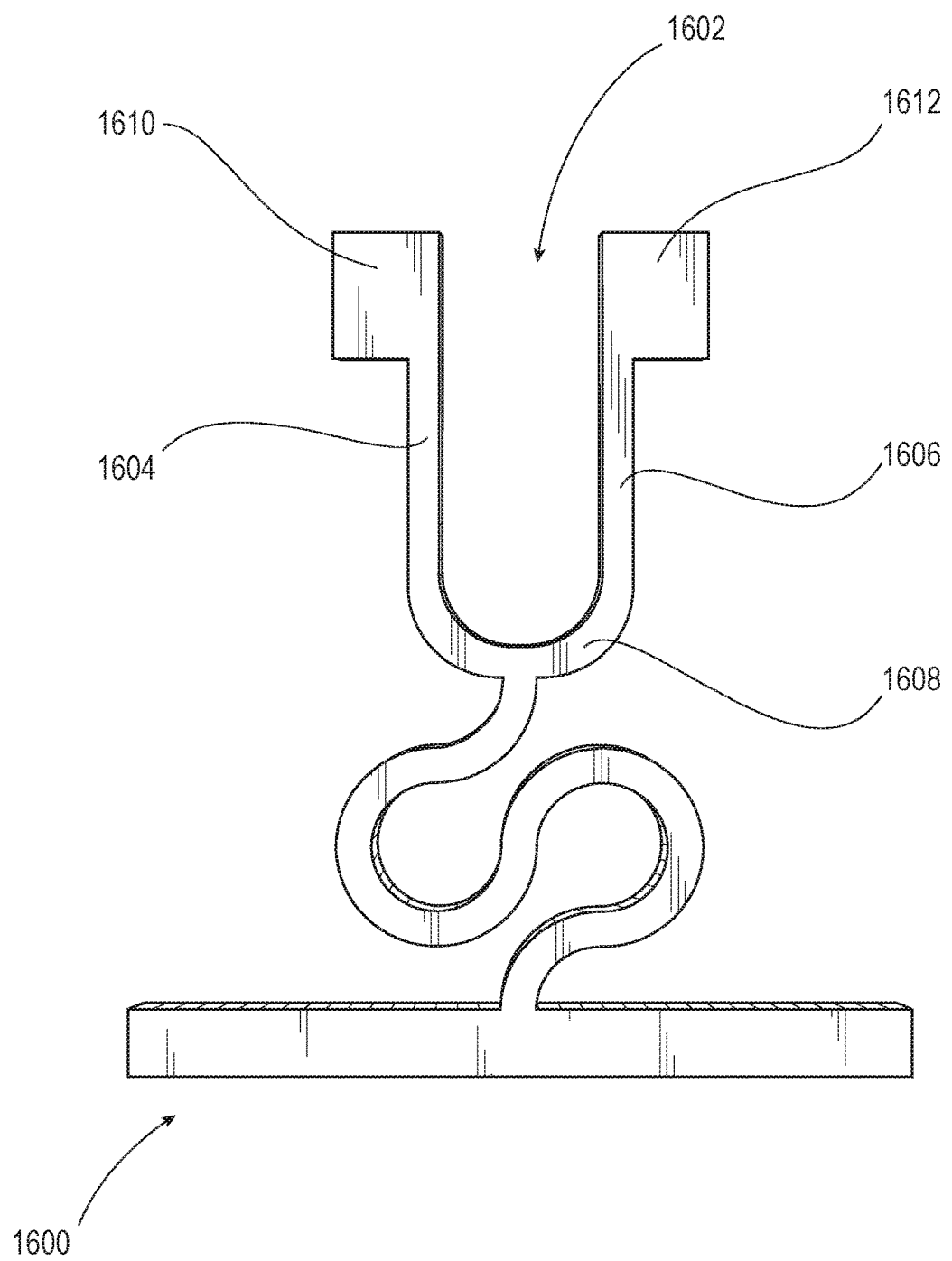
FIG. 16a is a front view of an example of a male connector element for an appliance.
Figure 16B:
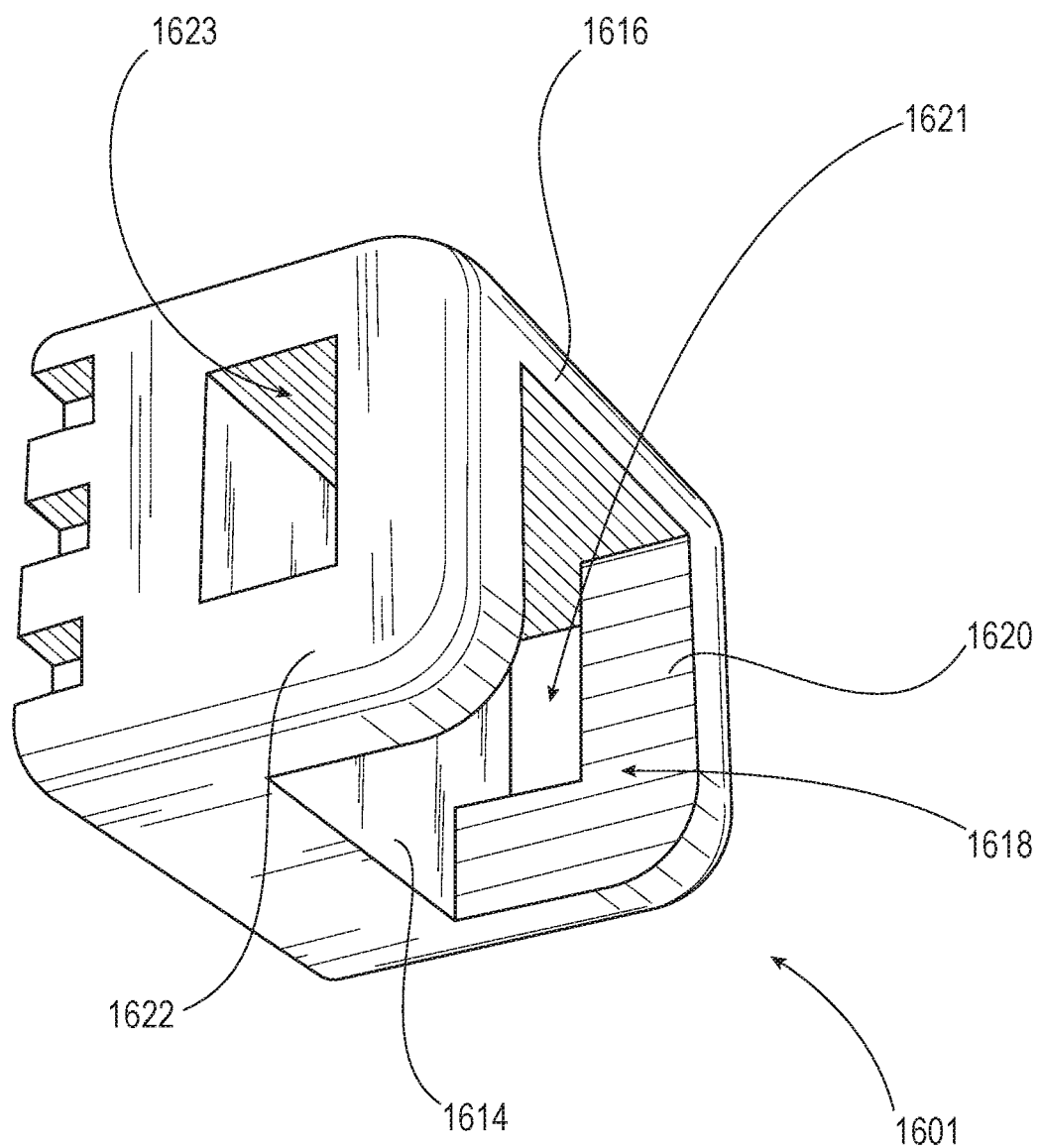
Figure 16C:
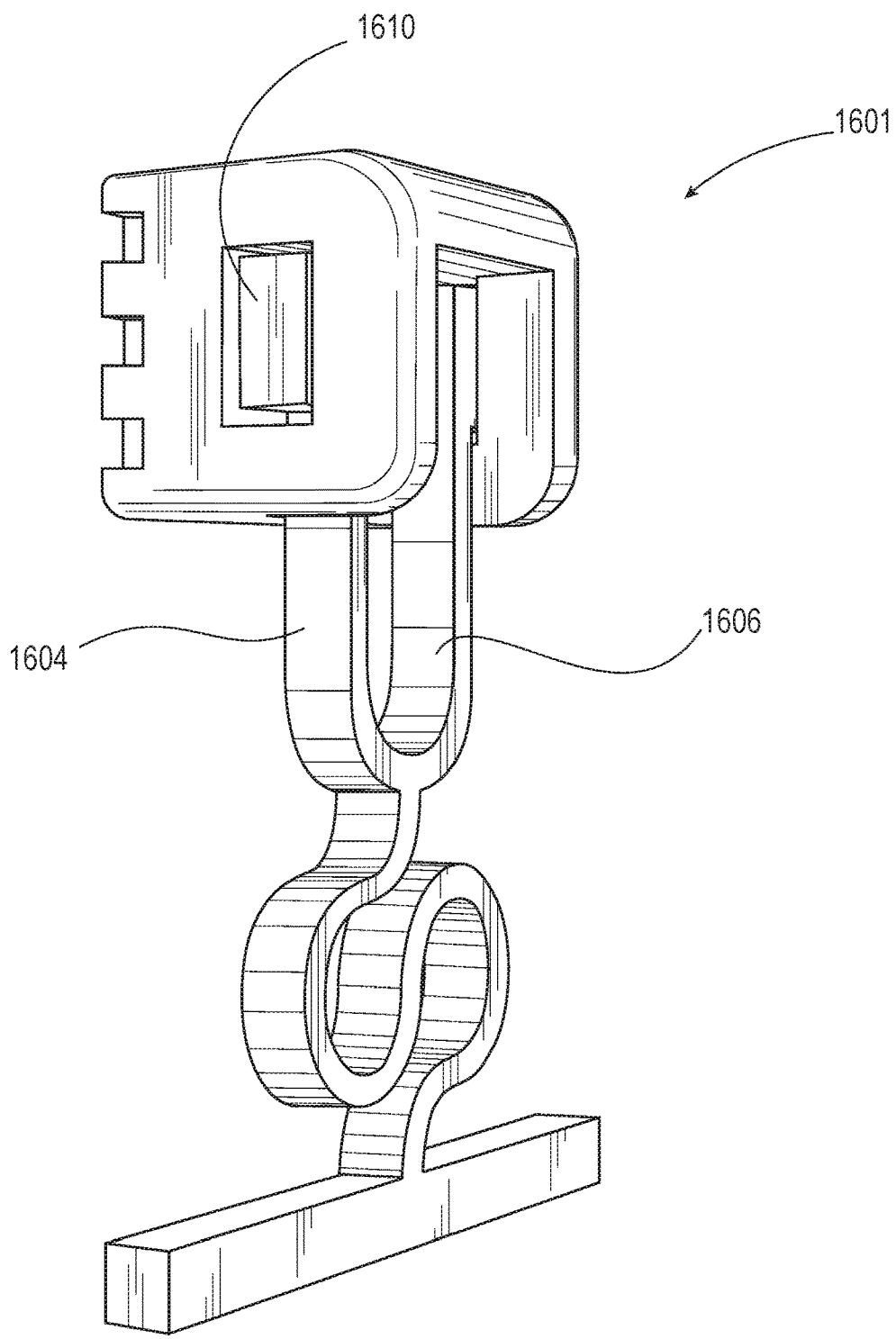
FIG. 16c is a perspective view of a male connector element received within a female connector element according to the examples of FIGS. 16a and 16b.

In other examples, male connector elements on appliances according to a second embodiment (including appliances 800, 900, 1000 and 1100) or according to a first embodiment may have yet other suitable configurations such as, but not limited to the configurations of the male connector element 1600 shown in FIG. 16a, for engaging and securing to a female connector element 1601 as shown in FIGS. 16b, and 16c. The male connector element 1600 in FIG. 16a includes a shaped body portion having first and second arm sections 1604 and 1606. Each arm section 1604 and 1606 is connected to other arm section at a first end 1608, and extends to a free end 1610, 1612, respectively. The free ends 1610 and 1612 include widened portions or L shaped end portions having extensions that extend outward from each arm section (in a direction away from the other of the two arm sections). The arm sections 1604 and 1606 are spaced apart from each other (except at the connected end 1608), to form a gap 1602 between the arm sections and extending along a portion of the length of each arm section. The male connector element is made of a sufficiently resilient material that allows the free ends of the arm sections 1604 and 1606 to be forced to move toward each other, and then resiliently move back to their original state when the force is removed. When the arm sections 1604 and 1606 are forced toward each other, the width dimension of the gap 1602 between the arm sections 1604 and 1606 decreases. In that state, the male connector element 1600 is placed into a receptacle of the female connector element 1601. When placed in the receptacle of the female connector element, the force on the arm sections 1604 and 1606 is released to allow the arm sections to resiliently move outward, toward their un-forced or passive state, to lock or secure the male connector element to the female connector element.

The female connector element shown in FIG. 16b includes a backing portion 1614, the back surface of which (the surface facing inward in the drawing) is configured to be bonded to a surface of a patient's tooth. An extension portion 1616 composed of box-shaped structure having an opening 1618 forming a receptacle, extends outward from the backing portion 1614. The box-shaped structure of the extension portion 1616 includes two side walls 1620 and 1622, each having an opening 1621 and 1623, respectively. The openings 1621 and 1623 are configured (in shape and size) to receive the free ends 1610 and 1612 include widened portions or L shaped end portions on the free ends 1610 and 1612 of the arm sections of the male connector element 1600, when the male connector element 1600 is secured to the female connector element 1601.

When the arm sections 1604 and 1606 of the male connector element 1600 are forced toward each other as described above, the male connector element 1600 may be inserted into the opening 1618 of the female connector element 1601 until the widened portions or L shaped end portions on the free ends 1610 and 1612 of the arm sections of the male connector element 1600 align with the openings 1621 and 1623 in the side walls 1620 and 1622 of the female connector element 1601. In that state, the force on the arm sections 1604 and 1606 may be released to allow the arm sections 1604 and 1606 to resiliently move outward from each other, to engage and insert the widened portions or L shaped end portions on the free ends 1610 and 1612 of the arm sections with and into the openings 1621 and 1623 in the side walls 1620 and 1622, to lock or secure the male connector element 1600 to the female connector element 1601. In that state, the male connector element 1600 may remain secured to the female connector element 1601, until a clinician removes the male connector element (for example, by forcing the arm sections 1604 and 1606 inward, toward each other sufficiently to withdraw the widened portions or L shaped end portions on the free ends 1610 and 1612 of the arm sections from the openings 1621 and 1623 in the side walls 1620 and 1622, and then pulling the male connector element away from the female connector element.

Figure 18A:
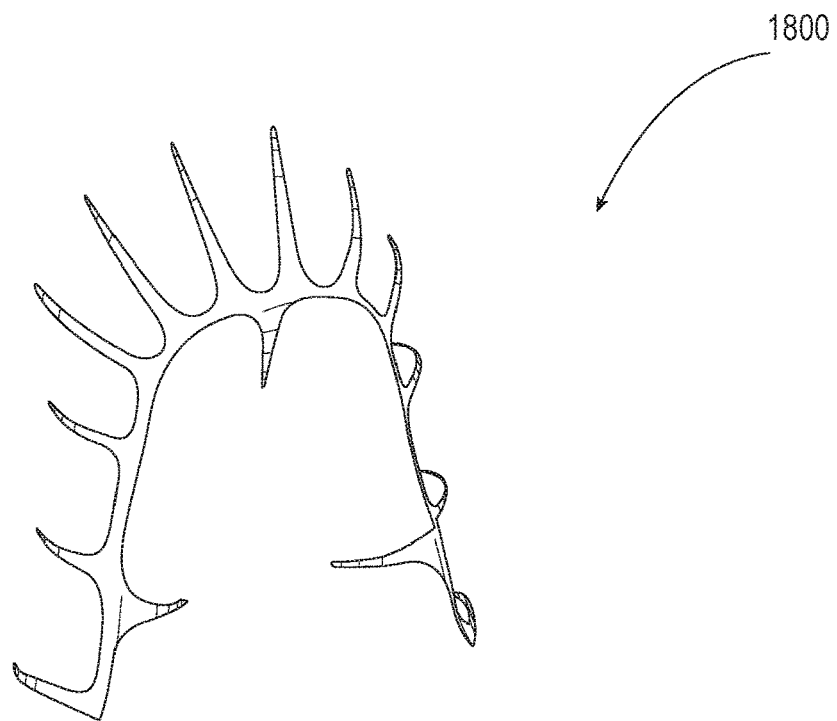
FIGS. 18a-d are perspective and plan views of members and two dimensional (2D) representations of an appliance.
Figure 18B:
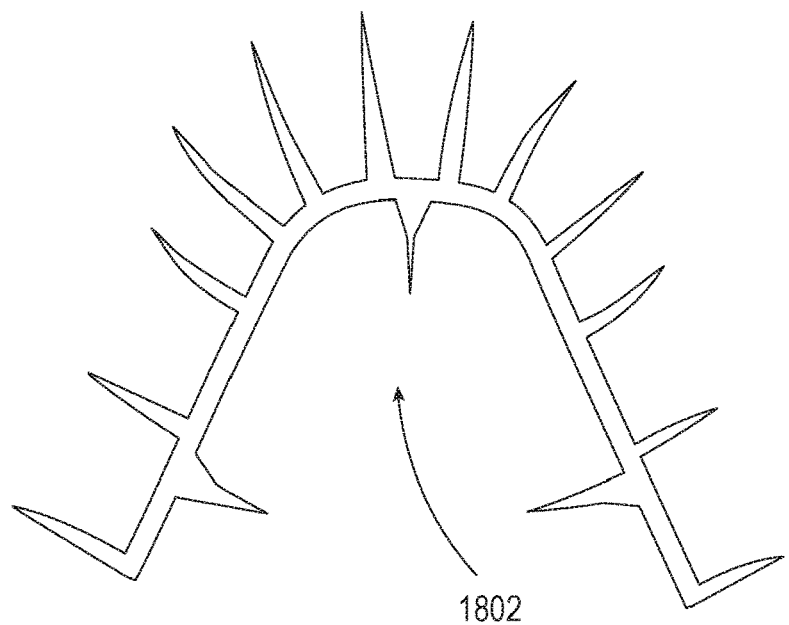
Figure 18C:
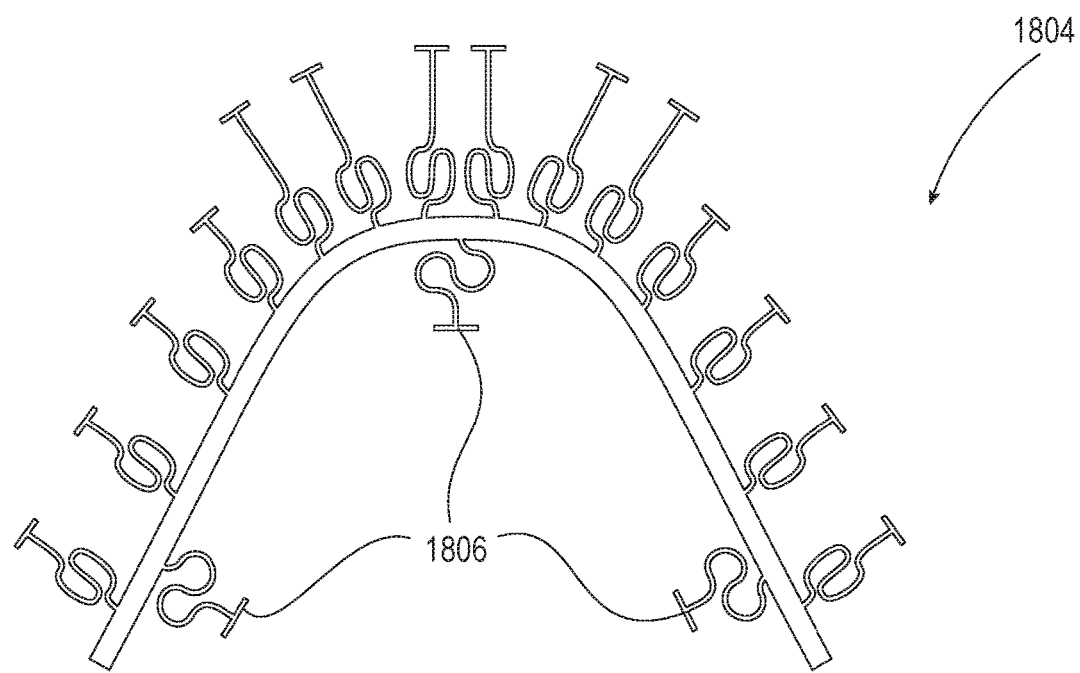
Figure 18D:
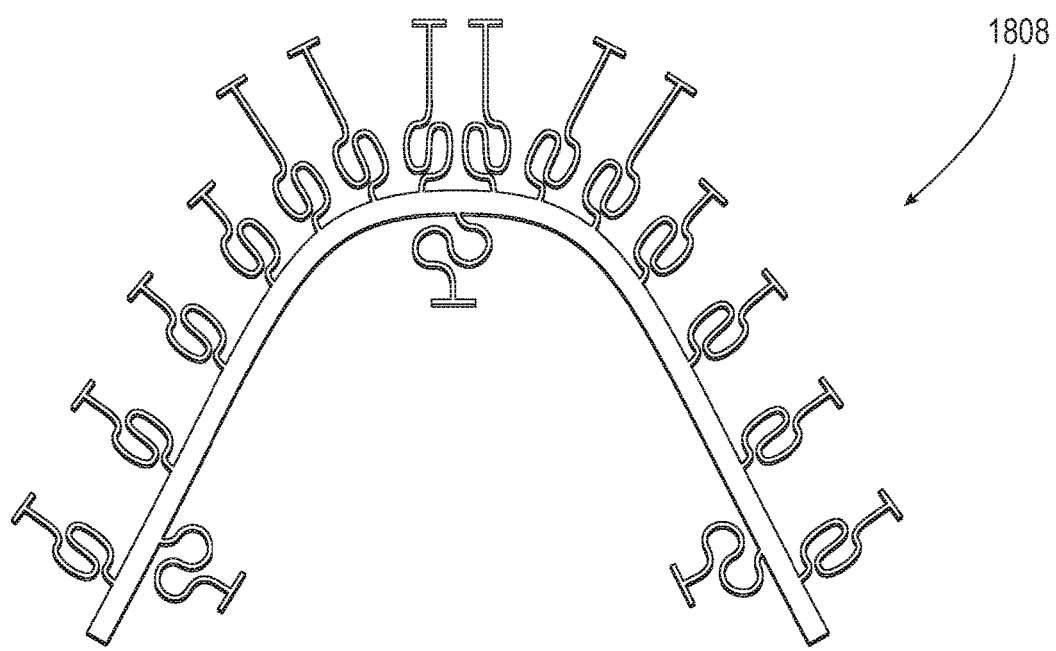
Figure 18E:
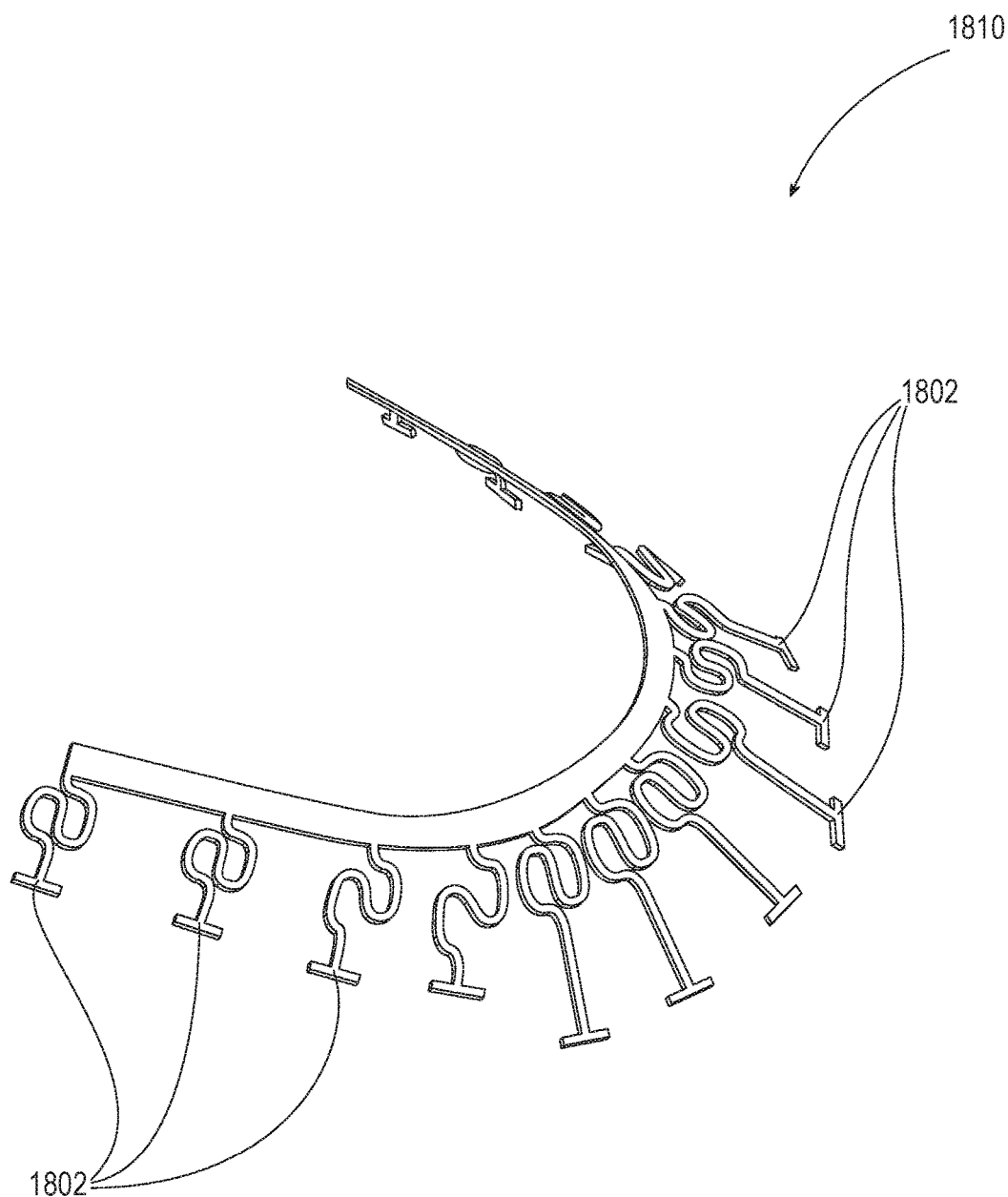
FIGS. 18e and 18f are perspective representations of appliances according to examples of the second embodiment, configured according to the members and representations of FIGS. 18a-d.
Figure 18F:
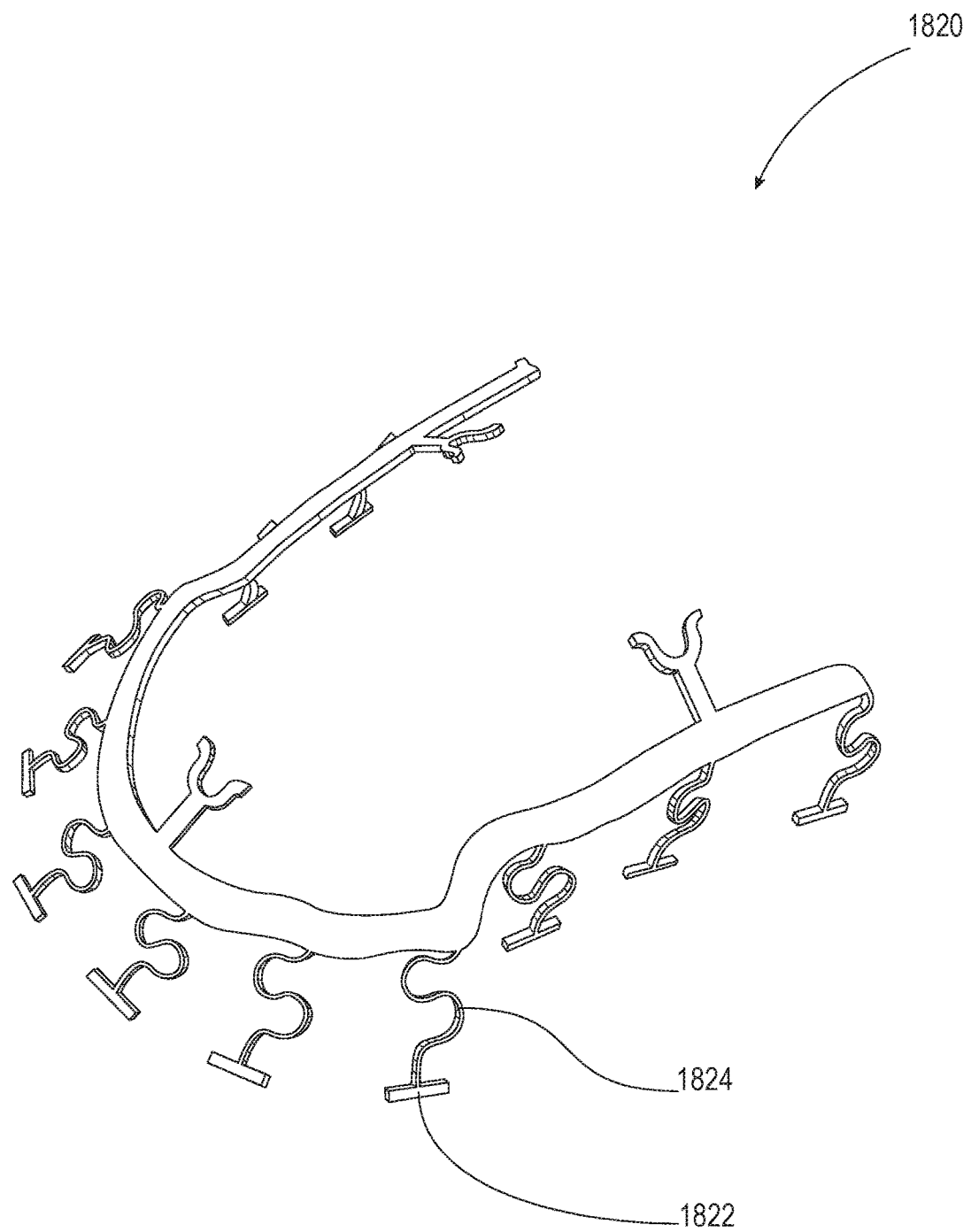

In other examples, male connector elements on appliances according to a second embodiment (including appliances 800, 900, 1000 and 1100) or the first embodiment may have other suitable configurations such as, but not limited to the configurations of the male connector element examples shown in FIGS. 18e and 18f. In the example appliances 1810 and 1820 shown in FIGS. 18e and 18f, each male connector element 1802 or 1822 has a T shaped configuration, for engaging and securing to a female connector element. In such example, the female connector element may have a corresponding T shaped slot for selectively receiving the T shaped male connector element.

Figure 25:
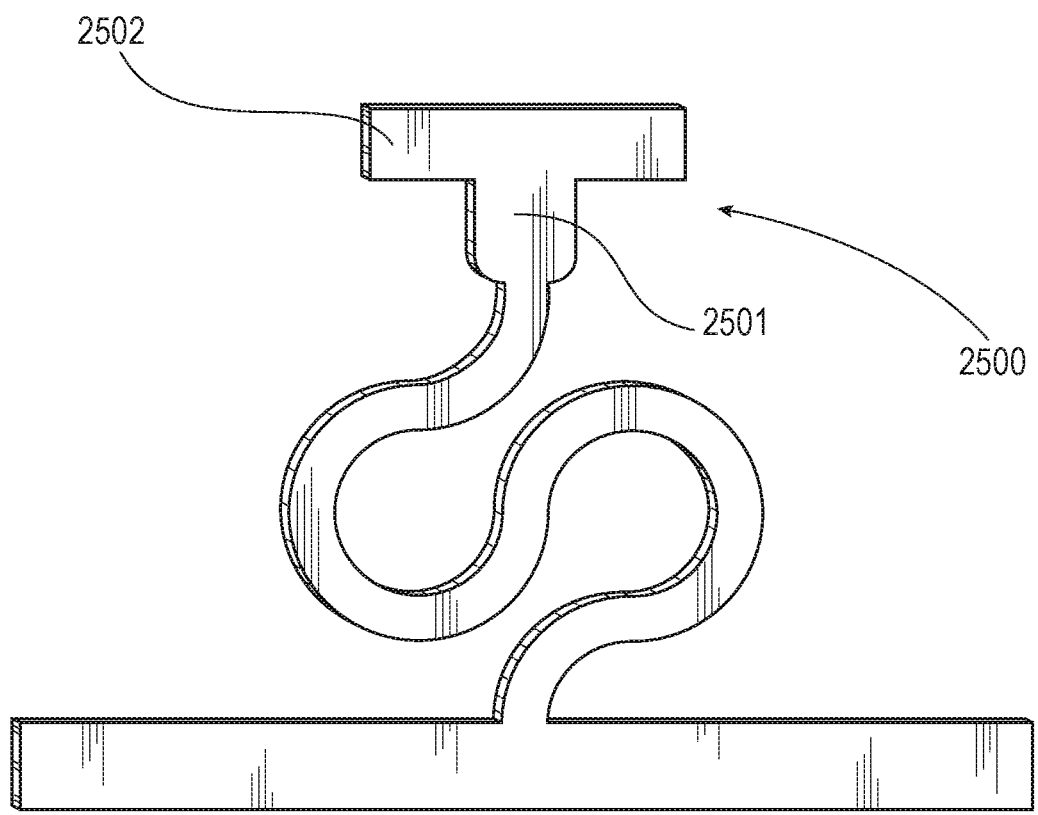
FIG. 25 is a front view representation of an example of a T shaped male connector element.

FIG. 25 shows an example of a male connector element 2500 having a T shaped configuration that may be used with embodiments described herein, including, but not limited to embodiments of FIG. 18e or 18f. The male connector element 2500 in FIG. 25 has a T shaped body structure provided at an end of an arm of an appliance. The T shaped body structure has a first portion 2501 extending in a direction of the arm (in a vertical direction in FIG. 25) and a second portion 2502 extending transverse to (such as, but not limited to, generally perpendicular to) the first portion 2501 (in a horizontal direction in FIG. 25).

An example of a female connector element 2600 is shown in FIGS. 26a-26d, for receiving and securing a male connector element having a T shaped configuration, such as, but not limited to the male connector element 2500 of FIG. 25. The drawings in FIGS. 26a-26d show a male connector element 2500 received by and secured to a female connector element 2600. The female connector element 2600 includes a backing portion 2601 and an extension portion 2602 extending outward from the backing portion 2601. The extension portion 2602 has a plurality of hook shaped extension members 2604 that are separated from each other to form a pair of traversing slots 2606 and 2608. The traversing slots are arranged to traverse each other at an angle corresponding to the traversing angle of the first and second portions 2501 and 2502 of the T shaped body of the male connector element 2500.

Accordingly, the male connector element 2500 may be aligned with and inserted into the traversing slots 2606 and 2608 of the female connector element 2600, to secure the male connector element to the female connector element. In particular examples, one or both of the slots 2606 and 2608 are slightly smaller in width than the width of the first or second portions 2501 and 2502 of the T shaped body of the male connector element. In such embodiments, the hook shaped extension members 2604 may have a sufficient flexibility and resilience to receive the T shaped body and impart a squeezing force on the T shaped body, when received within the traversing slots 2606 and 2608, for example, to help retain or secure the male connector element 2500 to the female connector element 2600.

Figure 26A:
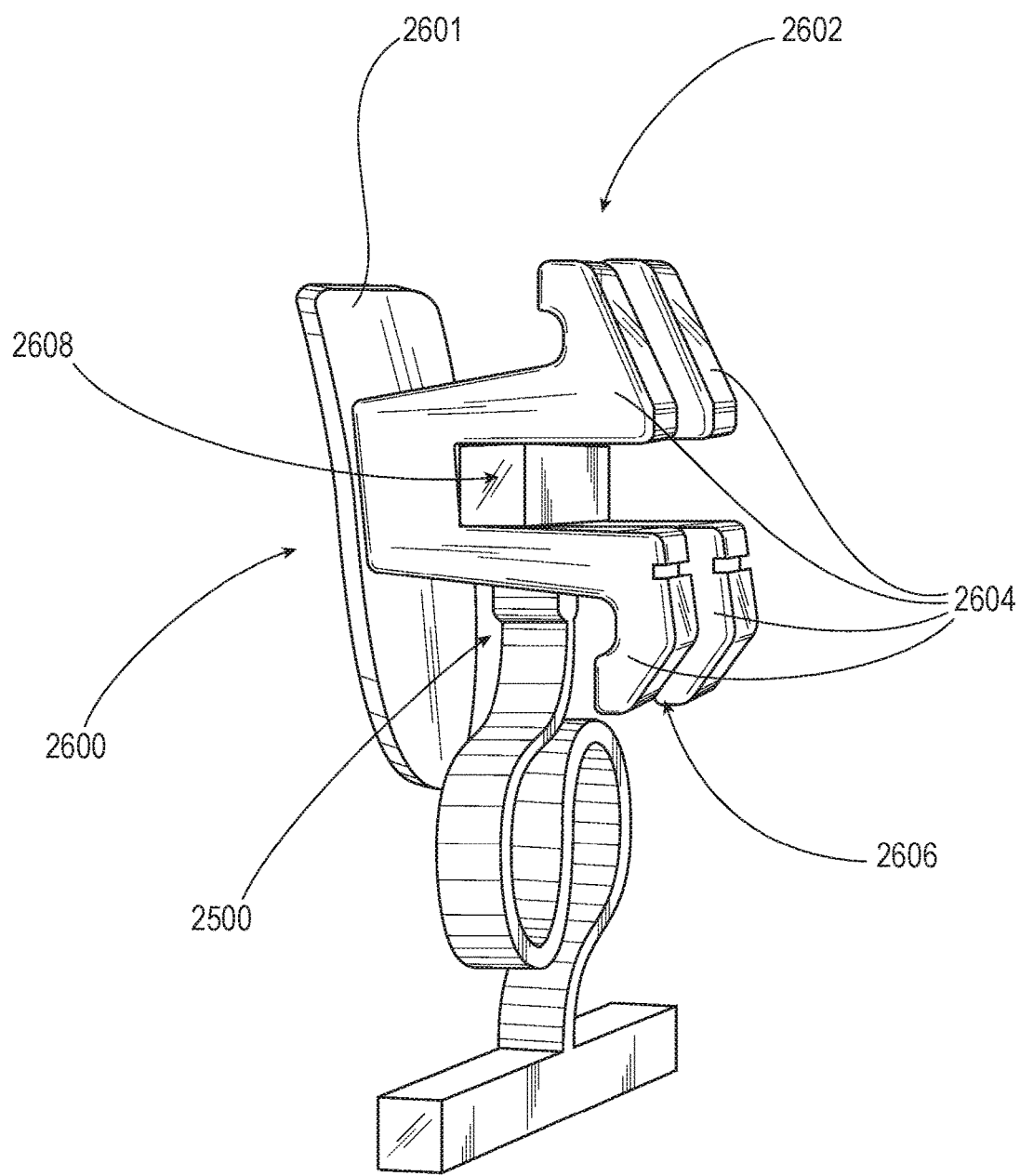
FIGS. 26a-f show perspective representations of examples of female connector elements receiving or for receiving a T shaped male connector element such as, but not limited to the type shown in FIG. 25.
Figure 26B:
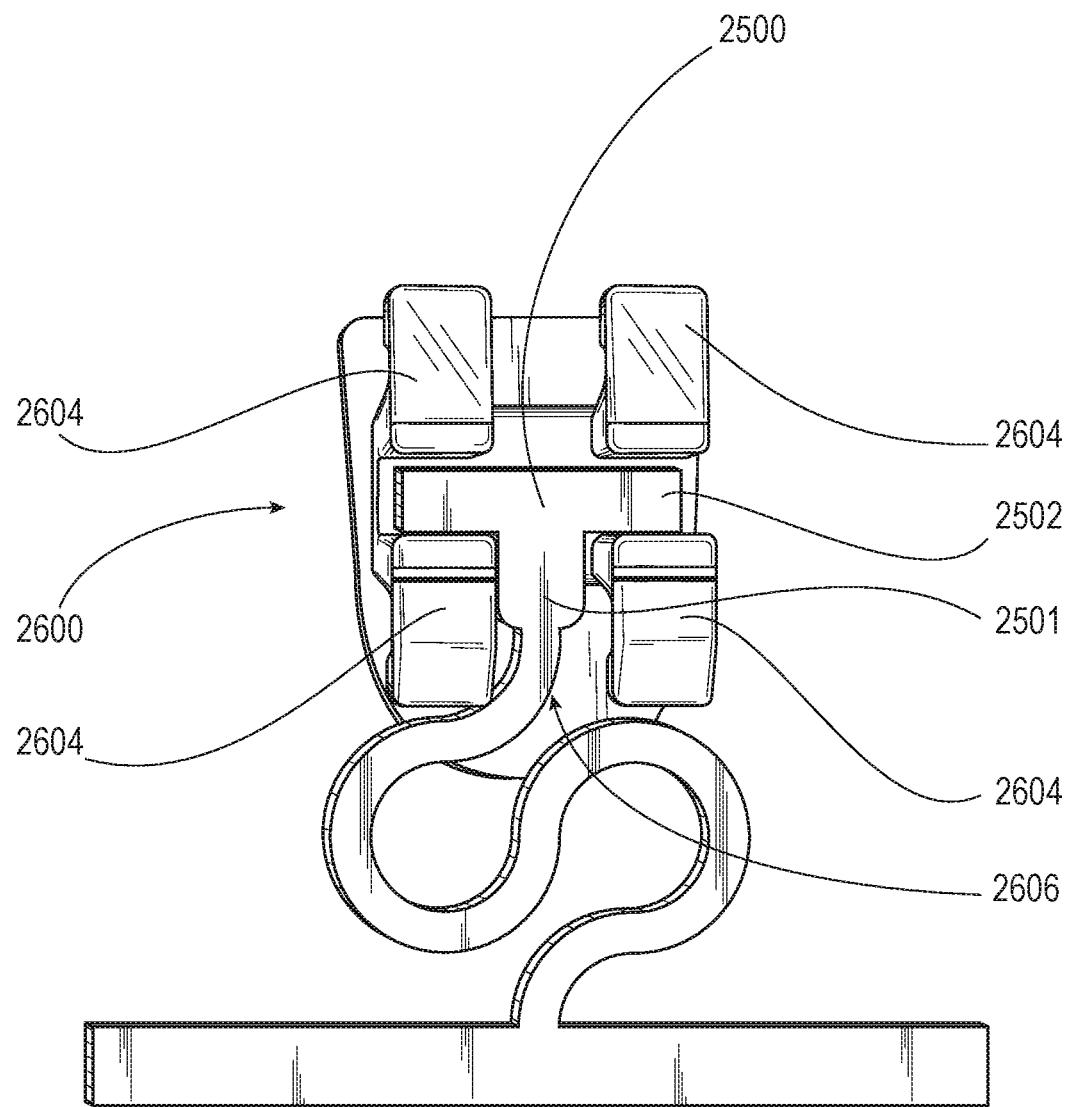
Figure 26C:
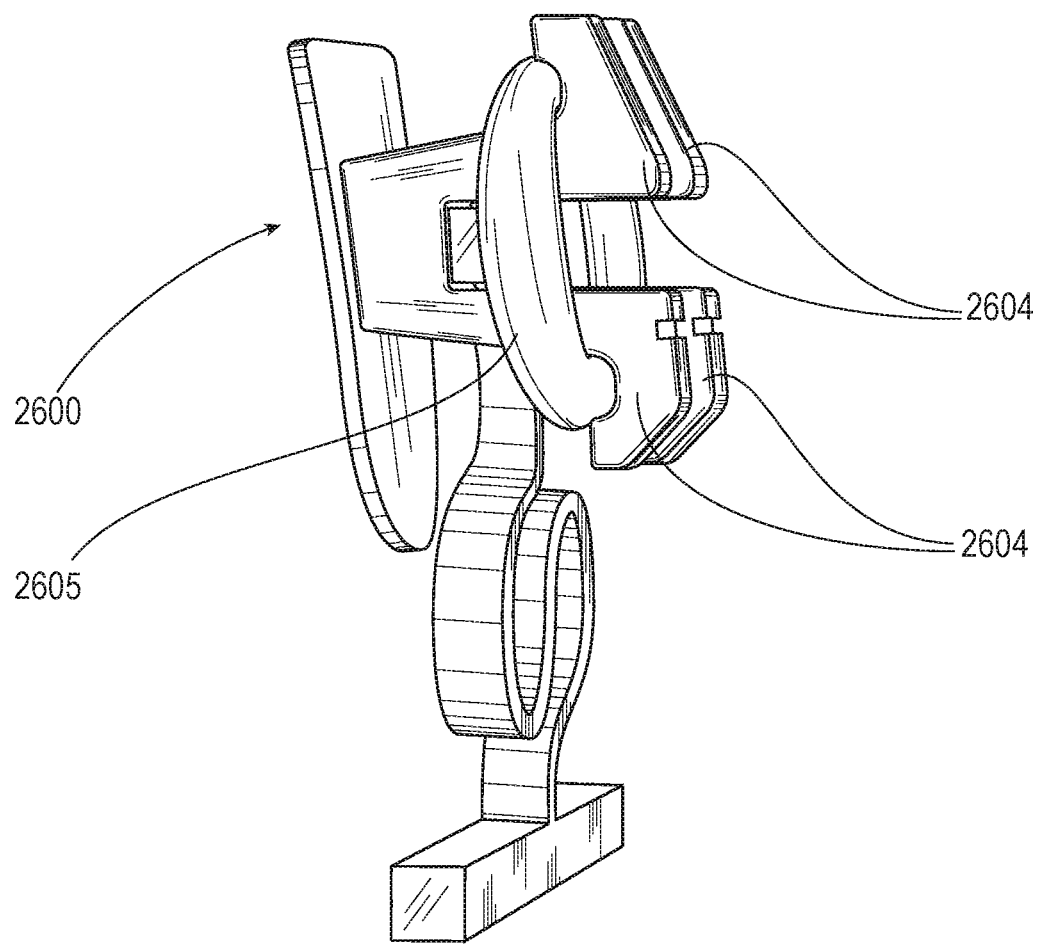
Figure 26D:
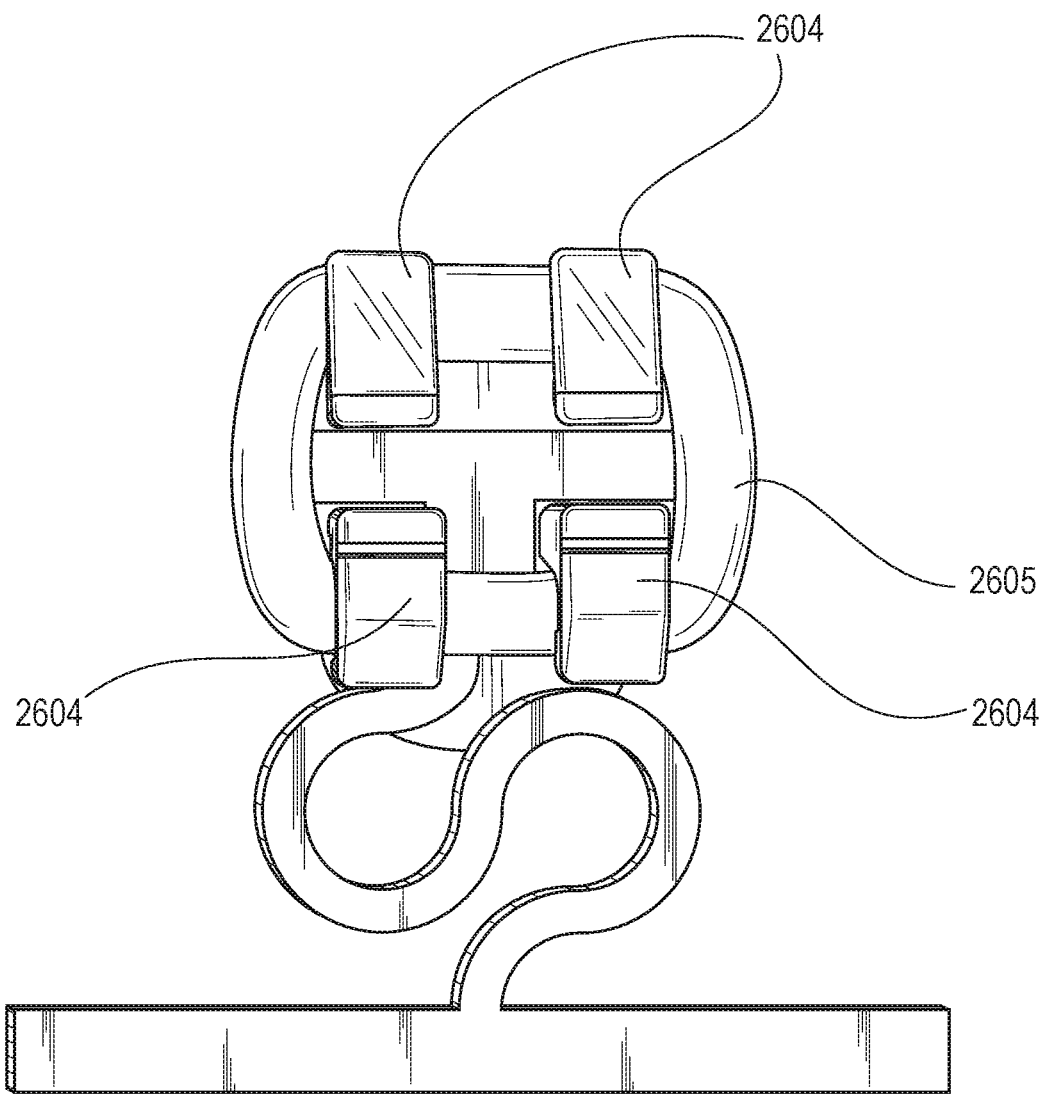

As shown in FIGS. 26c and 26d, a clinician may add a retaining structure 2605, such as, but not limited to an O-ring. ligature wire or other suitable retaining structure over the plurality of hook shaped extension members 2604 of the extension portion 2602 of the female connector element 2600, after the T shaped body of the male connector element 2500 is received in the female connector element. The hook shaped extension members 2604 may include a hook or L shaped end that retains the O-ring, ligature wire or other suitable retaining structure in place.

Figure 26E:
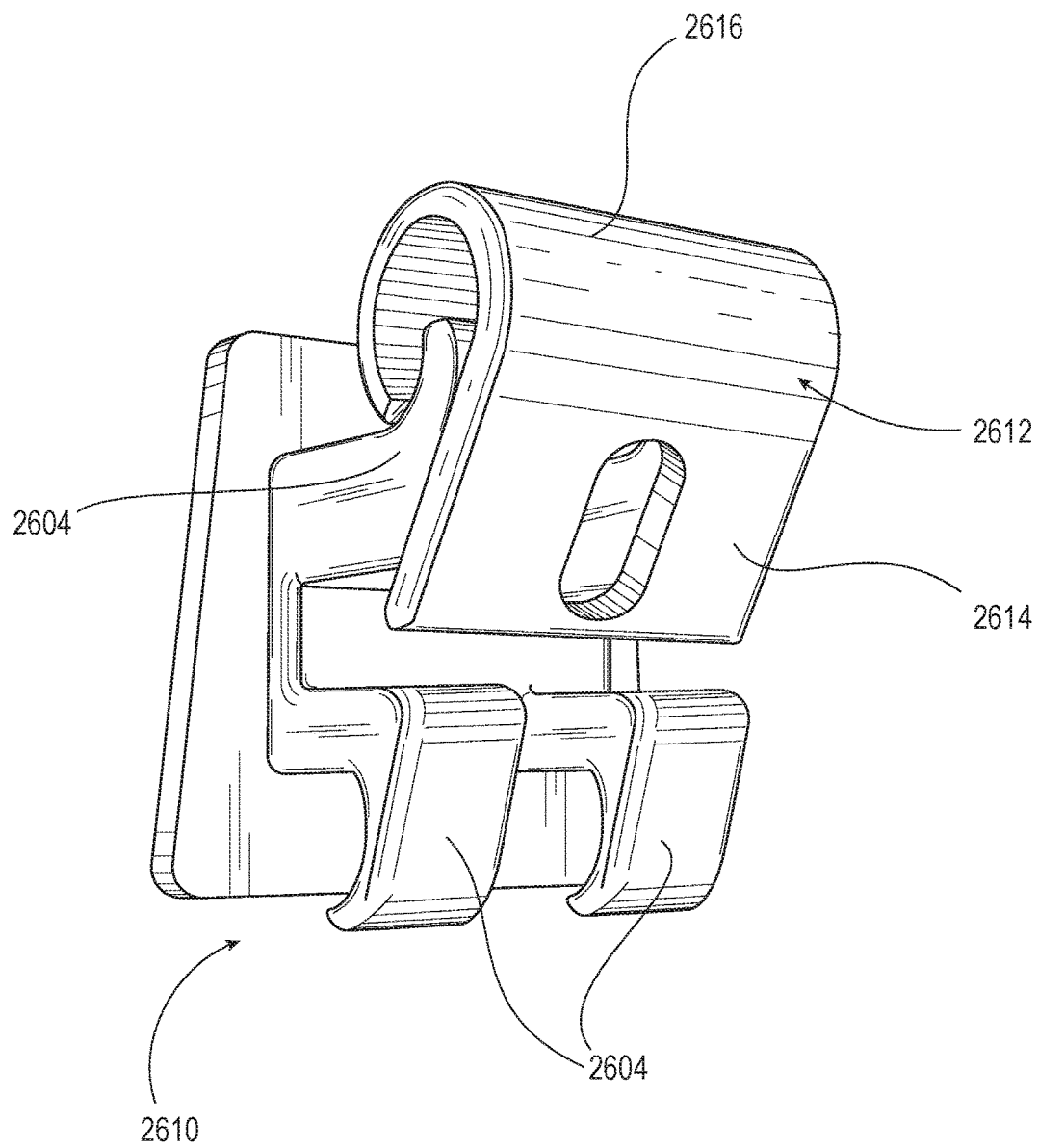
Figure 26F:
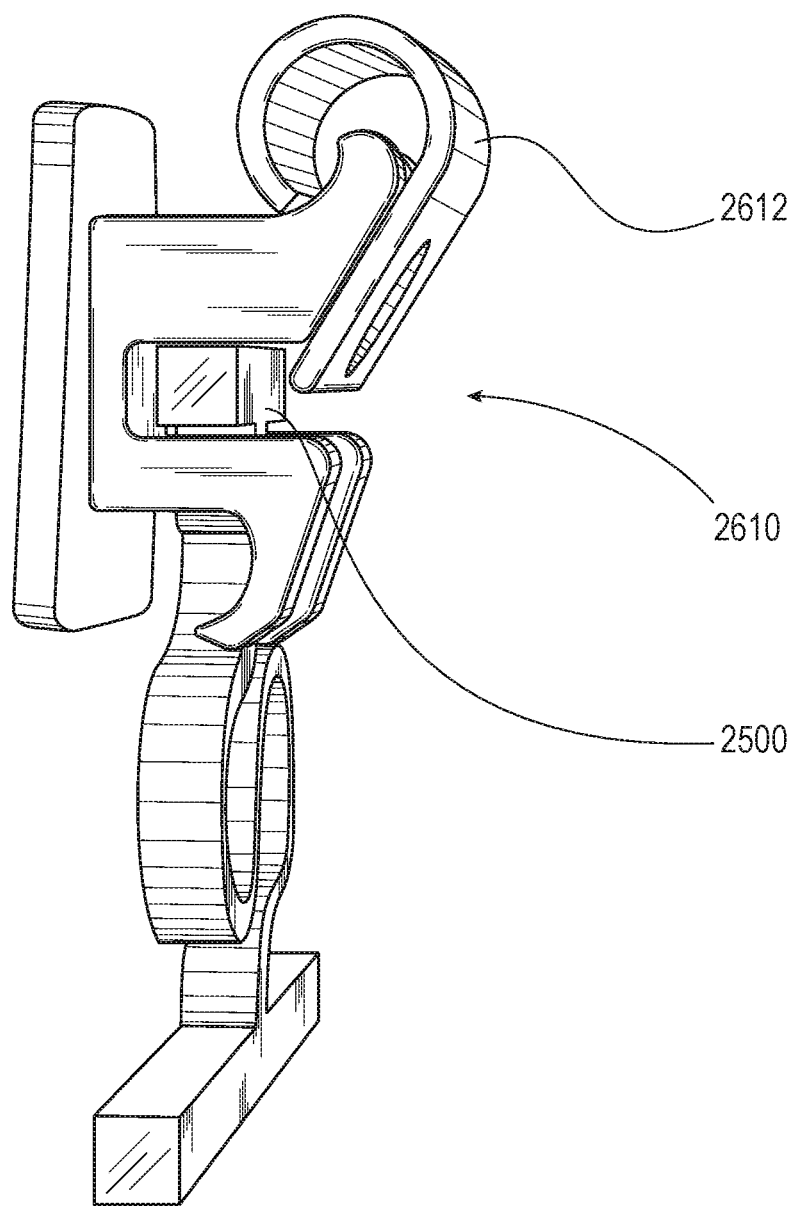

In a further example, a female connector element 2610 may be configured and operate similar to the female connector element 2600 described herein, but further includes one or more clip structures 2612 to operate as a self-ligating bracket, as shown in FIGS. 26e and 26f. The clip structure 2612 may be provided on or clipped over one (or a pair of) the hook shaped extension members 2604. In particular examples, the clip structure 2612 has a plate portion 2614 and a spring portion 2616 and is arranged such that the spring portion 2616 curves around or is otherwise supported on one or more hook shaped extension members 2604. The plate portion 2614 is supported to cover a portion of one or both of the traversing slots by a sufficient amount so as to inhibit removal of the T shaped body of the male connector element 2600, when the T shaped body is received within the traversing slots of the female connector element 2610. The spring portion 2616 provides sufficient flexibility and resilience to allow the plate portion 2614 to be moved outward (away) from the extension members 2604 by a sufficient amount to allow removal (or insertion) of the T shaped body of the male connector element 2600 from (or into) the traversing slots of the female connector element 2610, upon application of sufficient outward directed force on the plate portion 2616. Upon release of the force, the plate portion 2616 resiliently moves back toward its original state (as shown in FIG. 26f).

Figure 27A:
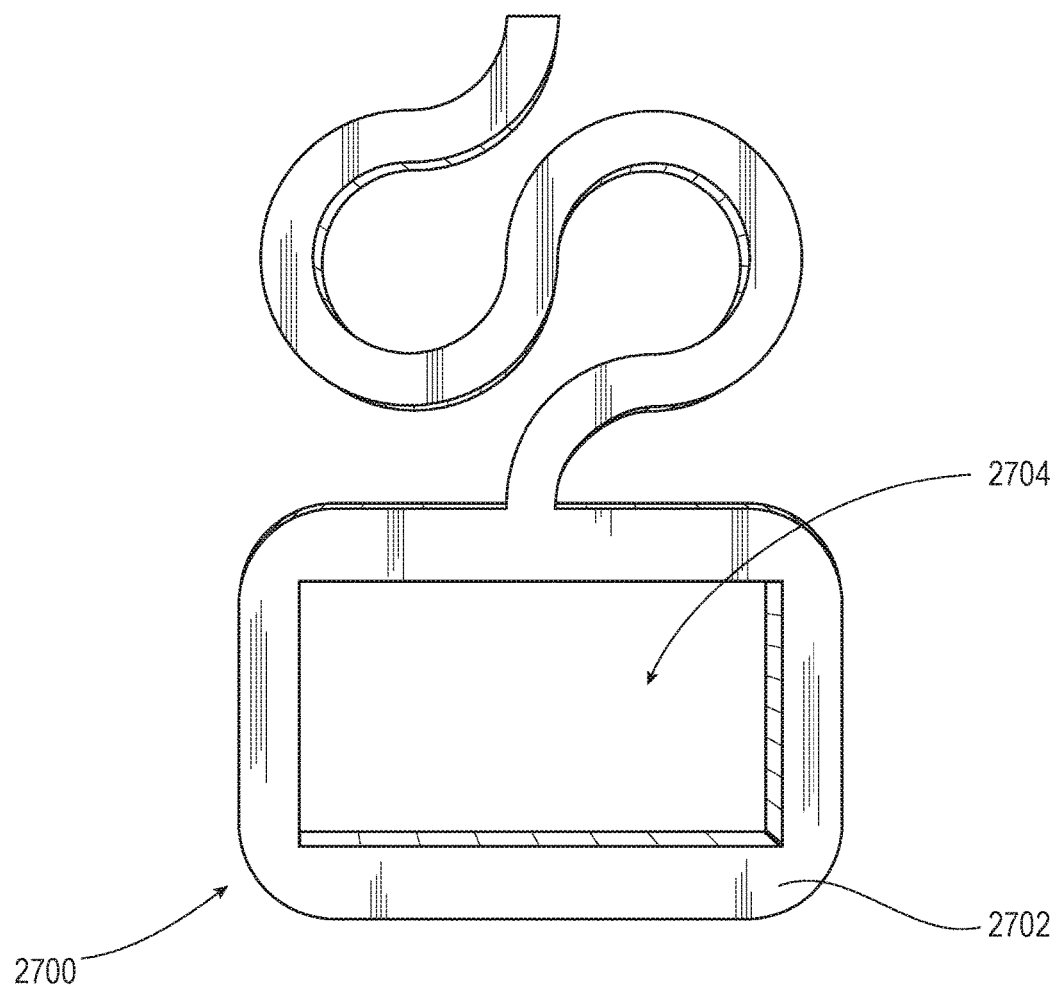
FIGS. 27a and 27b are front view representations of two examples of an annular shaped male connector element.

FIG. 27a shows another example of a male connector element 2700 having an annular (e.g., rectangular-annular with rounded corners) shaped configuration, that may be used with embodiments described herein, as an alternative to other male connector elements described herein. The corners of the annular shape of the male connector element 2700 are rounded for patient comfort. In other examples, the shape of the male connector element may include squared corners. The male connector element 2700 in FIG. 27a has an annular body structure 2702 provided at an end of an arm of an appliance (a spring portion of an arm, is shown in FIGS. 27a and 28). In other examples (consistent with the first embodiment), the male connector element 2700 may be provided on the arch shaped bar of the appliance (instead of at an end of an arm). In the illustrated example of FIG. 27a, the annular body structure 2702 has a generally rectangular shape with a central opening 2704. In other examples, the annular body structure 2702 may have other suitable shapes, including other polygons, ovals, circles or shapes formed as combinations of portions of polygons and ovals or circles. In other examples, such as, but not limited to the male connector element 2701 example shown in FIG. 27b, the body structure 2703 may be open on a corner, the bottom, right or left side in the illustrated orientation (and, thus, is partially, but not fully annular). In the example in FIG. 27b, the body structure 2703 is open at a corner (the upper-left corner, in the illustrated orientation). A male connector element 2701 that is open on a corner, bottom or side can be easier to form by cutting from a 2D sheet of material, as compared to a connector element 2700 that has a closed, annular shape.

Figure 27B:
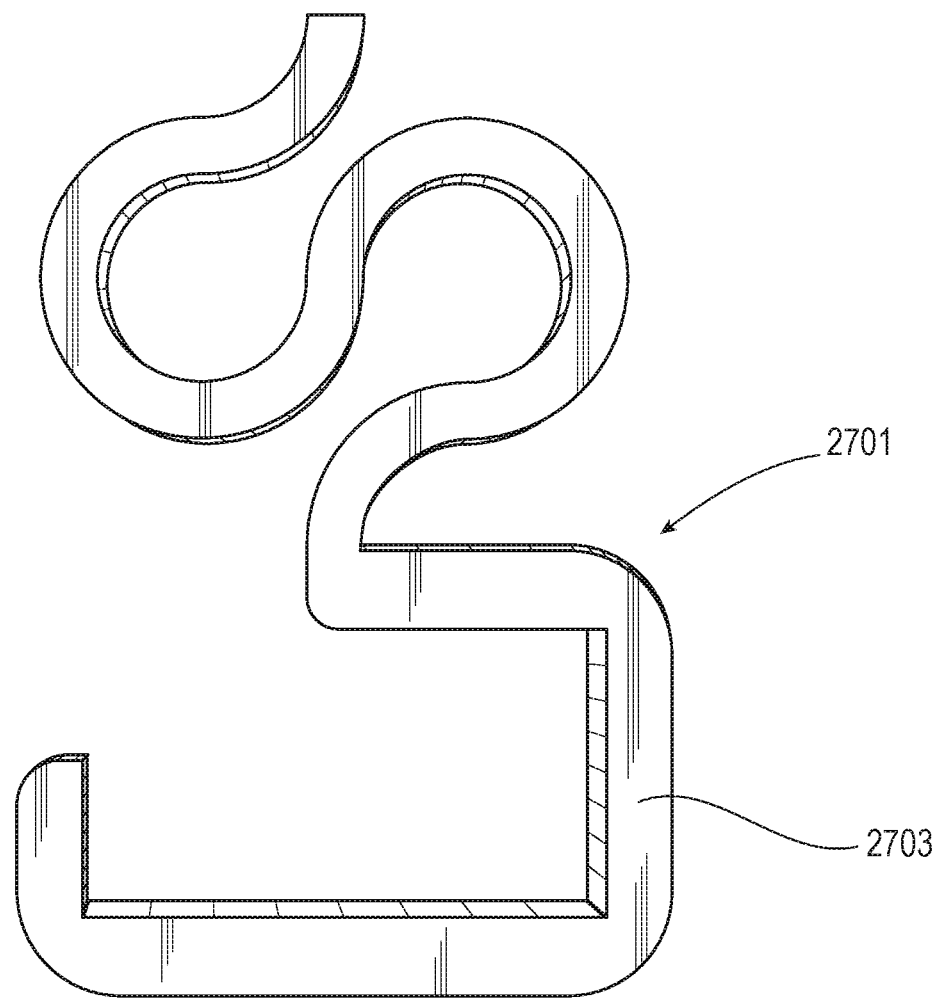
Figure 28:
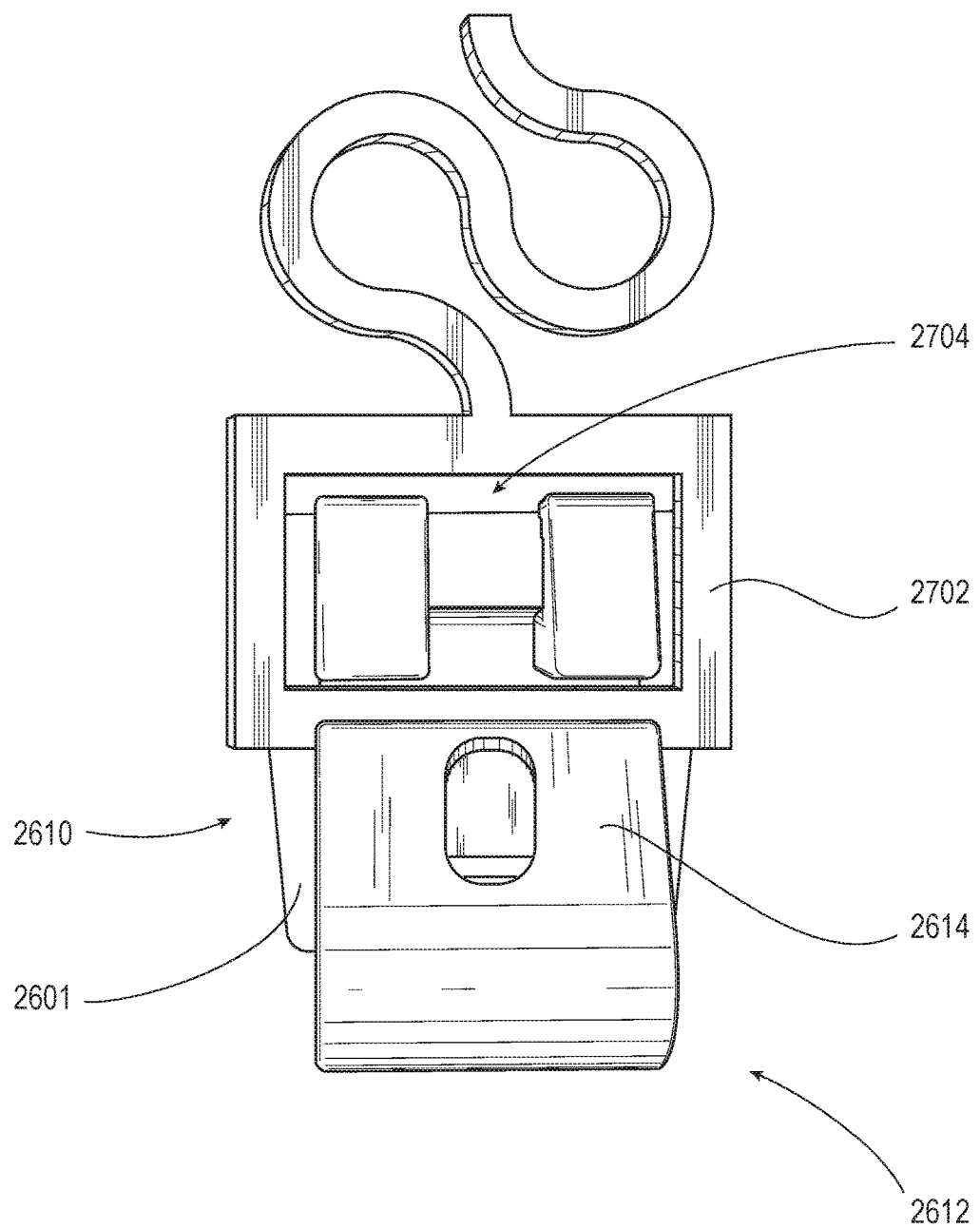
FIG. 28 is a front view representation of a male connector element of FIG. 27a engaged with a female connector element.

A male connector element 2700 or 2701 as shown in FIG. 27a or FIG. 27b may be configured to engage and secure with a female connector element having a configuration similar to that of female connector element 2610 described herein. Alternatively, a male connector element 2700 or 2701 may engage and secure to a female connector element that is configured similar to the female connector element 2610, but where the female connector element need not include a slot (without the vertical slot between extension members 2604 in FIG. 26a) and, thus, may engage and secure to a female connector element that has a conventional structure (or more conventional structure). An example of a male connector element 2700 engaged and secured with a female connector element 2610 is shown in FIG. 28. When engaged, as shown in FIG. 28, a portion of the annular body structure 2702 of the male connector element 2700 is interposed between the plate portion 2614 of the clip structure 2612 and the backing portion 2601 of the female connector element 2610. Another portion of the female connector element 2610 aligns with and partially fits into or through the central opening 2704 in the annular body structure 2702, to help align the male connector element with the female connector, when the male connector element 2700 is secured (or is being secured) to the female connector element 2610, as shown in FIG. 28. In this manner, the male connector element 2700 may be engaged with and secured to a self-ligating female connector element or bracket.

Various examples and configurations of male connector elements, and associated female connector elements may be employed in various examples of the second embodiment (and various examples of the first embodiment) described herein. Certain examples of appliances according to the second embodiment include male connector elements as described and shown with respect to FIGS. 1-3, 5 and 6 (for securing to female connector elements as described with respect to FIG. 7). Other example appliances according to the second embodiment include male connector elements as described and shown with respect to FIGS. 8-12h (for securing to female connector elements as described with respect to FIG. 13). Yet other appliances according to the second embodiment include male connector elements as described and shown with respect to FIG. 15a (for securing to female connector elements as described with respect to FIG. 15b, as shown in FIG. 15c). Yet other appliances according to the second embodiment include male connector elements as described and shown with respect to FIG. 16a (for securing to female connector elements of FIG. 16b, as shown in FIG. 16c). Yet other appliances according to the second embodiment include male connector elements as described and shown with respect to FIG. 17a (for securing to female connector elements as described with respect to FIG. 17b). Other appliances according to the second embodiment include male connector elements as described and shown with respect to FIGS. 18e, 18f and 25 (for securing to female connector elements as described with respect to FIGS. 26a-f). Other example appliances according to the second embodiment include male connector elements as described and shown with respect to FIGS. 27a and 27b (for securing to female connector elements as described with respect to FIG. 28). Yet other appliances according to the second embodiment include male connector elements having other suitable configurations for securing to female connector elements having other suitable configurations.

Systems or methods according to a second embodiment allow a clinician to move each tooth independently, by employing one or more appliances that have a separate arm connected to each tooth to be moved. The arms, including spring members of the arms, provide force generating elements, which impart a sufficient force on the teeth to move the teeth from their OTA to the desired FTA. In particular examples, the arms are able to move the teeth in one or more (or all three) translational directions. Alternatively or in addition, the arms are able to move the teeth in one or more (or all three) rotational directions.

One or more of the shape, thickness, width or length of each arm may be designed and configured to provide a suitable force or torque (or both) to achieve the desired movement of the tooth. In addition, one or more of the shape, thickness, width or length of each arm may be designed and configured to correspond to the size and type of the tooth to which the arm is connected. For example, one or more of the shape, thickness, width or length of the arms is designed and selected to provide a greater amount of flexibility when the teeth are to be displaced by a greater distance, or when the teeth are smaller in size, such as, but not limited to lower incisors.

In particular examples, processing and software systems with finite element analysis capabilities may be used to determine a desired geometry (size, shape, width, thickness, length) of the springs or arms (or both), for applying a desired or ideal force to accelerate the desired tooth movement.

A sectional form of an appliance according to the second embodiment could be configured to connect to some, but not all of the teeth in a jaw, for example, to move just a few teeth while keeping other teeth intact. In this case the number of arms in the appliance may be significantly less than the number of teeth in the given jaw, but the number of arms may match the number of teeth that the clinician desires to move. In other examples, one or more arms may be connected to one or more respective teeth for anchoring the appliance, and not necessarily for moving those teeth to which those arms are connected. In such examples, the one or more arms to be connected teeth for anchoring, but not moving the teeth, may be formed relatively strong or thick, to provide sufficient anchoring support. Some sample usages for a sectional form of an appliance according to the second embodiment include, but are not limited to opening space for an implant, aligning the teeth that are tipped in the extraction space, and non-comprehensive orthodontic treatment for patients for whom only a few teeth are mal-aligned. Another example of a sectional form of an appliance according to the second embodiment includes a molar positioner, as described with reference to FIG. 14.

Figure 14:
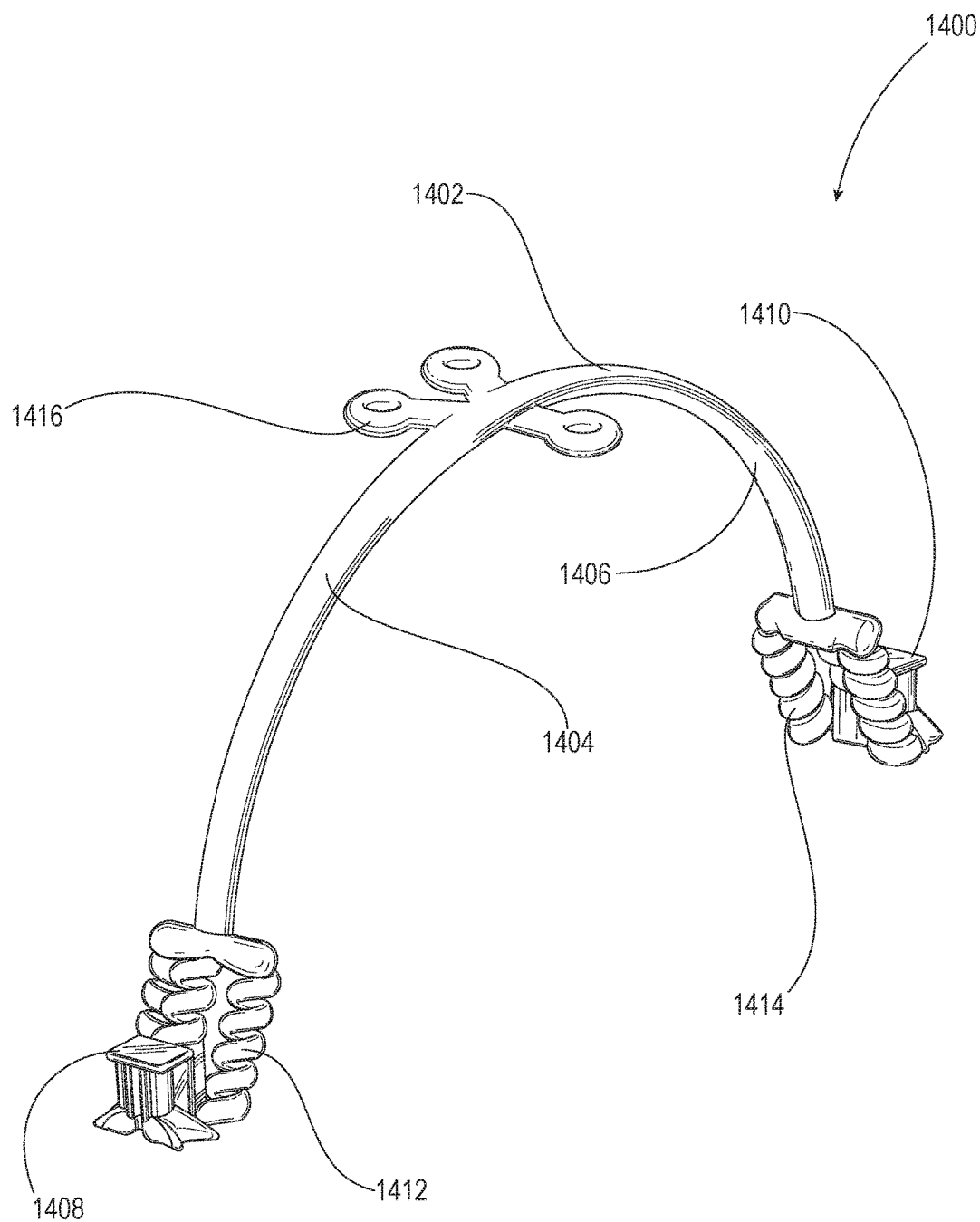
FIG. 14 is a perspective representation of an appliance according to another example of the second embodiment.

The appliance 1400 in FIG. 14 is configured as a molar positioner, for example, for use on upper molars of a patient with an incorrect intra-arch or inter-arch molar relationship. The appliance 1400 in FIG. 14 includes an arch-shaped bar 1402 forming two arms 1404 and 1406 that are joined at a central portion of the bar 1402. The arch-shaped bar 1402 is configured to cross over the palate of a patient, as a trans-palatal arch (TPA), when the appliance 1400 is installed on the patient's teeth.

Each arm 1404 and 1406 extends from the central portion of the bar 1402, to an end segment, at which a male connector element is located. The appliance 1400 includes a first male connector element 1408 formed on or otherwise attached to the end segment of the arm 1404 and a second male connector element 1410 formed on or otherwise attached to the end segment of the arm 1406. In the example shown in FIG. 14, the appliance 1400 also includes first and second spring structures 1412 and 1414, where spring structure 1412 is formed on the arm 1404 or is connected between the end section of the arm 1404 and the male connector element 1408 and where spring structure 1414 is formed on the arm 1406 or is connected between the end section of the arm 1406 and the male connector element 1410.

The spring structures 1412 and 1414 may be configured similar to configurations of spring elements (or combinations of spring elements) described herein. The male connector elements 1408 and 1410 are shown in FIG. 14 as having a configuration similar to the male connector element examples described with respect to any one or more of the examples in FIGS. 8-12g, for engaging female connector elements such as, but not limited to those described herein with reference to FIG. 13. However, in other examples, the male connector elements 1408 and 1410 may have other suitable configurations, such as, but not limited to those described herein with reference to FIGS. 1-3, 5, 6, 8-12h, 15a, 16a, 17a, 18c-18f, 25, 27a and 27b) for engaging and securing to female connector elements such as, but not limited to those described herein with reference to FIGS. 7, 13a, 13b, 15b, 15c, 16b, 16c, 17b, 26a-f, and 28.

The appliance 1400 in FIG. 14 includes one or more (three in FIG. 14) anchorage device holders 1416. Each anchorage device holder 1416 may be configured and operate similar to those described herein with reference to FIGS. 8 and 10, or other suitable configurations. In particular examples, one or more TADs or other suitable anchorage devices are employed to anchor the appliance 1400 (via the anchorage device holders 1416) to a patient's palate. In addition, the male connector elements 1408 and 1410 may be secured to female connector elements that were previously bonded to surfaces of upper molar teeth on opposite sides of the patient's jaw.

The appliance 1400 may be configured to apply suitable forces on the molar teeth to reposition the molar teeth, for example, to obtain a desired or ideal intra-arch and inter-arch molar relationship. The final position of the molar teeth can be determined by choosing the TADs locations, which may be precisely implanted by using a guiding tray.

In further examples, a molar positioner as described with reference to FIG. 14 could be used in mixed dentition, to gain room for un-erupted premolar and canine teeth, without involving other teeth in the jaw.

The appliances according to the second embodiment, and female connector elements associated with the first embodiment, may be manufactured in any suitable manner, including, but not limited to molding, casting, machining, 3D printing, stamping, extruding, or the like. However, in particular examples, appliances according to the second embodiment or female connector elements (or both) are made by cutting a 2D form of the appliance from a 2D sheet of material and bending the 2D form into a desired 3D shape of the appliance. As discussed below, such methods are particularly suitable for making appliances according to examples of the first and second embodiments described herein. By cutting the 2D member from a flat sheet of material, instead of a traditional single-diameter wire, a greater variety of 3D shapes may be made, as compared to shapes made by bending single-diameter wire. The cut 2D member may have designed or varying widths and lengths that, when bent into a desired shape, can result in portions of the 3D appliance having variances in thickness, width and length dimensions. In this manner, the 2D member can be cut into a shape that provides a desired thickness, width and length of spring members, arms, or other components of the appliance. A larger variety of shapes may be provided by bending a custom cut 2D member, as compared to bending a single-diameter wire.

In certain examples in which the appliance is formed from a cut 2D sheet of material that is bent into a desired 3D shape, the male connector element may be configured to be made from a flat sheet material that is cut or bent (or both) into a desired shape of the male connector element. FIG. 18e shows an example of an appliance 1800 according to an example of the second embodiment and formed from a cut 2D sheet of material that is bent into a desired 3D shape. In particular examples, the 3D shaped article may be shape set by any suitable shape setting procedure, including, but not limited to heat treatment. The example in FIG. 18e includes a plurality of male connector elements, where each male connector element has a generally T-shaped configuration as discussed above. Each T-shaped male connector element is configured to engage and secure with a respective female connector element having a configuration such as, but not limited to those shown in FIGS. 26a-f.

However, other examples, an appliance according to the second embodiment may be configured from a wire material that is bent into a desired 3D shape. In particular examples, the wire material is Nitinol. In other examples, the wire material may be any suitable material such as, but not limited to, Stainless steel, Beta-titanium and shape memory alloys.

An appliance according to various examples of the second embodiment may be configured to treat impacted teeth, such as, but not limited to, canines. For example, an appliance according to the second embodiment may be configured to bring impacted teeth to the mouth, by configuring an arm of the appliance to secure to the impacted tooth and apply a force to draw the tooth toward the patient's dental arch. In particular examples, the appliance may include one or more anchorage device holders for connecting to one or more TADs or other anchorage devices implanted in the patient, to help apply the desired force or torque (or both) on the impacted tooth, to move the impacted tooth to its final desired or ideal position. The appliance may be configured to be passive (and apply no further force or torque onto the tooth) when the tooth is at its final position, but active (to apply a force or torque, or both, on the tooth) at any other position.

Accordingly, as compared to traditional braces, an appliance according to the second embodiment may be configured to apply an appropriate force and torque on an impacted tooth, from the beginning of exposure, such that the tooth may be drawn toward the patient's dental arch and rotated in an appropriate direction to reach a final desired or ideal position. In contrast, a traditional orthodontics technique with braces may involve moving teeth to the arch without any torque control, followed by additional treatment to apply torque to the tooth. Accordingly, appliance examples according to the second embodiment may be configured to expedite treatment time by applying force and torque at the same time, over the course of a treatment. Also, by employing TADs or TPAs in appliance examples as described herein, the reaction force (of the force applied to the tooth) is applied to the TADs or TPAs, which can minimize reaction force side effects. Appliances according to various examples can reduce round tripping of the teeth, which can reduce treatment time, root resorption and provide other benefits.

Third Embodiment

As discussed above, systems or methods according to a third embodiment include or employ an appliance that has a configuration similar to the first embodiment, but are further configured to be selectively removable, to allow a patient (or clinician) to selectively install and remove the appliance from a patient's teeth. An appliance according to the third embodiment includes a plurality of caps (such as, but not limited to aligner, acrylic or polymer caps) instead of the male connector elements described above. However, other features of an appliance according to the third embodiment may be configured and operate as described above with respect to examples of the first embodiment (including, but not limited to examples shown in FIGS. 1-3, 5, 6, 16 and 17).

In an appliance according to the third embodiment, each aligner cap is configured to secure to a respective tooth by fitting over and onto the tooth. For example, the caps may be made of a polymer, acrylic or other suitable materials, such as materials that help to retain each cap to a patient's tooth. In particular examples, additional or alternative connector elements may be provided to assist in attaching one or more (or each) of the caps to a respective tooth.

In particular examples of systems and methods according to the third embodiment, the caps may be configured to secure and hold to the teeth, by engaging natural undercuts on surfaces of the teeth, or via artificial undercuts provided by attachments or buttons secured on the teeth. These attachments can be made out of metal, polymers, ceramic, or other suitable materials. In certain examples, the attachments can be made to have the same or similar color as the teeth, to be less visible and more esthetically pleasing. Attachments with the same or similar color as the teeth can be out of materials such as, but not limited to composite resins, polymers or ceramics. In particular examples, an attachment can be secured to a patient's tooth with a tray that helps the clinician to install the attachment in a desired position.

In the third embodiment, each cap may be customized in size and/or shape to correspond to the size and shape of the tooth to which the cap fits. Alternatively, the aligner caps are configured for application to any patient or tooth (or a group of multiple patients or teeth) and are not customized for each tooth or patient. In certain examples of the third embodiment, each aligner cap may be separately connected to a support bar and not directly connected to any other caps for adjacent teeth. In other examples, one of the aligner caps (or each of a plurality of aligner caps) may be connected to two or more adjacent teeth, for example, to move a group of teeth in unison or to provide additional anchorage. This gives an appliance according to the third embodiment significantly greater flexibility, which can allow the clinician to use fewer appliances to complete a treatment.

Figure 19A:
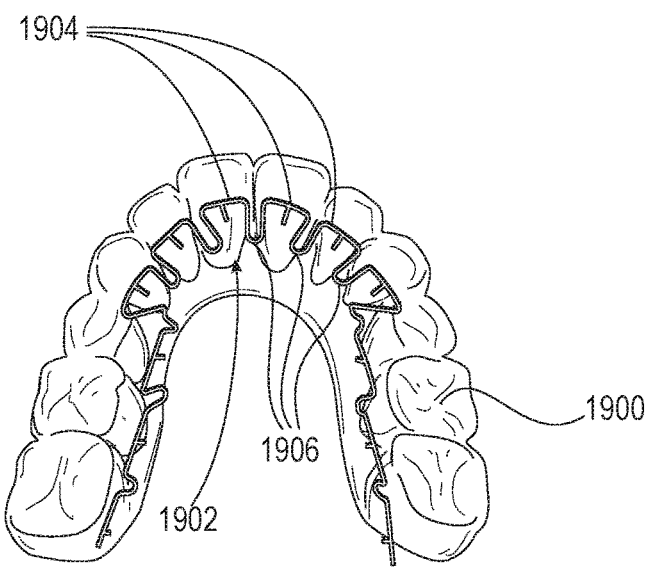
FIGS. 19a-b are perspective representations of tools and components for making an appliance according to the third embodiment.
Figure 19B:
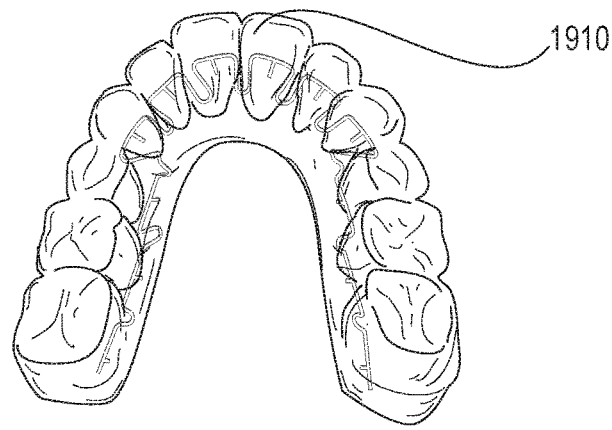
Figure 19C:
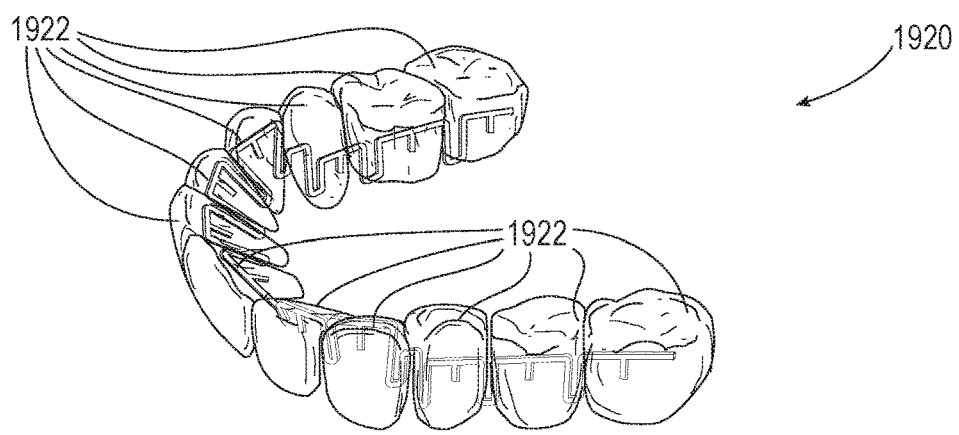
FIG. 19c is a perspective representations of an appliance made in accordance with FIGS. 19a-b, according to the third embodiment.

As shown in FIG. 19c, an example of an appliance 1920 according to the third embodiment may include an arch-shaped structure 1902 (best shown in FIG. 19a) and a plurality of caps 1922. The arch-shaped structure 1902 includes a shaped support member that may be made of any suitable material such as, but not limited to Nitinol (NiTi), stainless steel, beta-titanium, cobalt chrome or other metal alloy, polymers or ceramics. The arch-shaped structure 1902 may be formed in a desired shape, by using any suitable shape forming procedure, including, but not limited to the methods described herein for forming appliances according to the first embodiment. In the example of FIG. 19c, the arch-shaped structure 1902 may have a configuration similar to the appliance shown and described with respect to FIG. 17a, or other suitable configuration.

In particular examples, the arch-shaped structure 1902 of the appliance 1920 is configured to follow the arch of an upper jaw of a patient (for example, as described with respect to the arch-shaped structures of the appliances 100, 200 and 500). In other examples, the arch-shaped structure of the appliance is configured to follow the arch of a lower jaw of a patient (for example, as described with respect to the arch-shaped structures of the appliances 300 and 600). Some or all of the arch-shaped structure of an appliance according to the third embodiment may be made of any suitable material including, but not limited to nitinol, stainless steel, beta-titanium, cobalt chrome or other metal alloy, polymers or ceramics, and may be made as a single, unitarily-formed structure or, alternatively, in multiple separately-formed components connected together in single structure.

A plurality of cap connector elements 1904 are formed on or attached to the arch-shaped structure of an appliance according to the third embodiment, at locations spaced apart along the length of the arch-shaped structure (instead and in place of male connector elements shown in the appliance examples of FIGS. 1-3, 5 and 6). In an appliance according to the third embodiment, one or more springs 1906 are provided between adjacent cap connector elements 1904 (and, thus, between adjacent aligner caps). In certain examples of the third embodiment, one or more springs are provided between each cap connector element and each adjacent cap connector element. In other examples of the third embodiment, one or more springs are provided between some, but not all of the pairs of adjacent cap connector elements. For example, a rigid portion of the appliance may be provided between one or some pairs of adjacent cap connector elements. In further examples, one or more springs may be provided between cap connector elements that are not directly adjacent with each other. Each spring is a force-generating component of the appliance. In particular examples, each spring is made of a flexible material, such as, but not limited to a shape memory alloy, such as, but not limited to nitinol.

Each cap connector element 1904 is configured to connect to and retain a separate respective cap 1922, relative to each other cap connector element. In other examples, multiple caps may connect to and be retained by one or more (or each) respective cap connector element. In further examples, one or more (or each) cap connector element may respectively connect to and retain more than one cap. Accordingly, individual caps 1922 are connected in the arch-shaped member 1902, at separated and spaced apart locations along the arch-shaped member, such that each cap 1922 is separate from (not directly connected to) an adjacent cap. In this manner, caps on the appliance (and teeth to which those caps are secured) may move separately and independent of other caps on the appliance (and teeth to which those caps are secured), and need not restrict movement of other caps on the appliance (and teeth to which those caps are secured). In certain examples, the caps do not cover springs located between adjacent caps on the appliance. In particular examples, the caps of adjacent teeth may be configured and mounted on the arch-shaped structure at locations at which they do not come in contact with each other throughout the entire course of treatment. In further examples, the appliance may be configured with one or more caps that fit over a plurality of teeth (or have multiple adjacent caps that are connected together), while one or more other caps in the appliance are separated from and independent of other caps in the appliance.

In examples of an appliance according to the third embodiment, each cap 1922 may comprise an aligner. In such examples, an Essix® machine or other suitable thermoforming or vacuum forming machine can be used to attach each aligner cap to a respective cap connector element on the arch-shaped member.

In certain examples, the aligner may cover the entire appliance, for example, to be more comfortable for the patient. In such examples, a space or clearance between the springs and the aligner may be formed. In such examples, patient may feel additional comfort, since the patient's tongue will only come into contact with the smooth surface of the aligner instead of coming in contact with the metal arms or bar of the appliance. The aligner may be trimmed either manually or with another suitable machining or cutting method (such as, but not limited to laser cutting, milling, or the like).

In other examples of an appliance according to the third or fourth embodiment, as an alternative or in addition to one or more of the male connector elements, the appliance may include other mechanisms for engaging and securing to one or more teeth of a patient. For example, one or more engaging mechanisms may be configured to pass the lingual surface of the teeth through the incisal or interproximal surfaces and hold the teeth from buccal side (for example, similar to a clasp in partial denture). In other examples, one or more engaging mechanisms may be configured to pass the buccal surface of the teeth, through the incisal or interproximal surfaces, and hold the teeth from the lingual side (for example, similar to a clasp in a partial denture).

In various examples of systems and methods according to the third embodiment, the appliance may be configured to move teeth until the caps of the removable appliance are passive and do not apply force to the teeth.

Similar to other embodiments described herein, appliances according to the third embodiment may be designed and manufactured using computerized design and manufacturing techniques such as, but not limited to, those described herein. Appliances according to the third embodiment may be configured to exhibit elasticity for longer ranges of movement as compared to traditional removable appliances. For example, the inclusion of spring members between caps and the use of separately connected caps (not directly connected to adjacent caps) can allow for greater ranges of movement, than appliances that do not include springs members or that employ inter-connected caps. Consequently, example methods according to the third embodiment may involve fewer appliances to complete a treatment as compared to traditional removable appliances with stainless steel springs or as compared to traditional aligner treatment (such as, but not limited to Invisalign® or ClearCorrect®).

In other examples of an appliance according to the third embodiment, any suitable combination of aligners on some teeth and clasps on other teeth may be used. In such embodiments, the appliance may include one or more aligners at locations for one or more corresponding teeth, and one or more clasps at locations for one or more other teeth in the patient's jaw. Alternatively or in addition, different types of clasps may be employed at different teeth locations on the appliance. For example, the flexibility of clasps made of NiTi, on the posterior teeth, can increase retention capabilities of the appliance. This may be helpful if a malocclusion requires greater retention of the appliance to the teeth.

An appliance according to the third embodiment may include one or more palatal arch feature or lingual arch feature, for example, but not limited to, palatal arch feature 202 or 804 in FIGS. 2 and 8, respectively, or lingual arch feature 302 in FIG. 3.

An appliance according to the third embodiment may include one or more anchorage device holders, for anchoring the appliance to a patient's palate or buccal shelf, as described herein with regard to anchorage device holders 812 or 904 in FIGS. 8 and 10. For example, one or more anchorage devices (such as, but not limited to TADs) may be implanted into the palate or buccal shelf of a patient, or other suitable locations on the patient. A removable appliance according to the third embodiment may include one or more engagement features that are configured to engage and connect to the implanted anchorage device when the appliance is installed on a patient's teeth, and to selectively disconnect from the implanted anchorage device for removal of the appliance. In such embodiments, the engagement feature may include one or more of a snap connector (for snap connection to the implanted anchorage device), slide connector (for slide connection to the implanted anchorage device), or other suitable connector. Alternatively, or in addition, a platform may be secured to the patient's palate or buccal shelf, where the platform includes one or more snap, slide or other suitable engagement features for engaging and connecting with one or more snap, slide or other suitable engagement features on the removable appliance, for selective connection and disconnection of the appliance from the platform. In further examples, any suitable bone anchorage device may be used instead of or in addition to one or more TADs.

Fourth Embodiment

As discussed above, systems or methods according to a fourth embodiment include or employ an appliance that has a configuration similar to the second embodiment, but is further configured to be selectively removable, to allow a patient (or clinician) to selectively install and remove the appliance from a patient's teeth. Similar to the second embodiment, an appliance according to the fourth embodiment has a plurality of separate arms configured to individually connect to a corresponding plurality of teeth, via caps, where each arm of the appliance is configured to connect to a different respective tooth relative to each other arm of the appliance. In other examples, one or more of the aligner caps (or each of a plurality of aligner caps) may be connected, individually, to two or more adjacent teeth, for example, to move a group of teeth in unison or to provide additional anchorage.

Accordingly, various features of an appliance of the fourth embodiment may be configured and operate as described above with respect to examples of the second embodiment (including, but not limited to examples shown in FIGS. 8-12g). However, instead of the male connector elements of the second embodiment, an appliance according to the fourth embodiment includes a plurality of caps (such as, but not limited to aligner caps, acrylic caps or polymer caps). A separate respective cap is formed on or otherwise attached to each respective arm, for example, at an end of each arm opposite to the arm end that attaches to an arch-shaped bar of the appliance. The caps are configured to hold the appliance to the patient's teeth and to maintain the appliance in a desired position during use.

The caps of the fourth embodiment may be configured similar to the caps described herein for the third embodiment, to secure to a patient's teeth by fitting over and onto the teeth. However, the separate caps of the fourth embodiment are attached to ends of the separate respective arms, instead of directly to the arch-shaped structure of the appliance.

Systems or methods according to the fourth embodiments (in which an appliance includes a plurality of separate arms configured to individually connect to a corresponding plurality of teeth) can provide distinct advantages of providing and controlling individual tooth movement. Such advantages can allow a clinician to reduce round tripping of the teeth thereby reducing treatment time, root resorption, and the number of trips the patient is required to take to the orthodontist. Thus, in comparison to traditional orthodontic techniques in which a plurality of the teeth are connected to a single arch wire such that moving one tooth results in the unintentional movement of nearby teeth, particular examples described herein allow a clinician to control the movement of each tooth independent of each of the other teeth.

In various examples of systems and methods according to the fourth embodiment, the appliance may be configured to move teeth until the caps of the removable appliance are passive and do not apply force to the teeth. Similar to other embodiments described herein, appliances according to the fourth embodiment may be designed and manufactured using computerized design and manufacturing techniques such as, but not limited to, those described herein.

Similar to the third embodiment, various examples of an appliance according to the fourth embodiment may include any suitable combination of aligners for some teeth and clasps for other teeth in a patient's jaw. In such embodiments, the appliance may include one or more aligners at locations for one or more corresponding teeth, and one or more clasps at locations for one or more other teeth in the patient's jaw. Alternatively or in addition, different types of clasps may be employed at different teeth locations on the appliance. For example, the flexibility of clasps made of NiTi, on the posterior teeth, can increase retention capabilities of the appliance. This may be helpful if a malocclusion requires greater retention of the appliance to the teeth.

An appliance according to the fourth embodiment may include one or more palatal arch feature or lingual arch feature, for example, but not limited to, palatal arch feature 202 or 804 in FIGS. 2 and 8, respectively, or lingual arch feature 302 in FIG. 3. An appliance according to the fourth embodiment may include one or more anchorage device holders, for anchoring the appliance to a patient's palate or lingual site, as described herein with regard to anchorage device holders 812 or 904 in FIGS. 8 and 10. In such examples, one or more anchorage devices (such as, but not limited to TADs) may be implanted into the palate or lingual area of a patient for engagement and disengagement (and selective connection and disconnection) as described with respect to the third embodiment.

In particular examples of systems and methods according to the fourth embodiment, the caps may be configured to secure and hold to the teeth, by engaging natural undercuts on surfaces of the teeth, or via artificial undercuts provided by attachments or buttons secured on the teeth, as described above with respect to the third embodiment.

The arms of an appliance according to the fourth embodiment (similar to an appliance according to the second embodiment) may include one or more flexible elements, such as springs, that apply a force and have a flexibility that can be selected or customized, based upon the size of the tooth as well as the desired movement of the tooth to which the arm is connected. In an appliance according to examples of the fourth embodiment, a single cap is attached to each arm and, in particular examples, does not cover any portion of the flexible elements of the arm or the bar. In other examples, more than one cap is attached to an arm, or more than one of the arms is attached to plurality of caps, or combinations thereof. A cap connector element (for example, similar to the cap connector element 1804 described above) may be formed or otherwise connected to an end section of each respective arm and may connect to a single respective cap. In other examples, more than one cap connector is connected to one of the caps, or more than one of the caps is secured to plurality of cap connectors, or combinations thereof.

In particular examples, the caps are configured to attach to the patient's teeth in such a way as to avoid contact between caps for adjacent teeth. In this manner, caps on the appliance (and teeth to which those caps are secured) may move separately and independent of other caps on the appliance (and teeth to which those caps are secured), and need not restrict movement of other caps on the appliance (and teeth to which those caps are secured).

In examples of an appliance according to the fourth embodiment, each cap may comprise an aligner. In such examples, an Essix® machine or other suitable thermoforming or vacuum forming machine can be used to attach each aligner cap to a respective cap connector element on an arm of the appliance.

In certain examples, the aligner may cover the entire appliance, for example, for comfortable for the patient. In such examples, a space or clearance between the springs on the arms and the aligner on the arm may be formed. In such examples, patient may feel additional comfort, since the patient's tongue will only come into contact with the smooth surface of the aligner instead of coming in contact with the metal arms or bar of the appliance. The aligner may be trimmed either manually or with other suitable machining or cutting method (such as, but not limited to laser cutting, milling, or the like).

In other examples, the teeth may be held by configuring one or more of the arms to pass the lingual surface of the teeth through the incisal or interproximal surfaces and hold the teeth from the buccal side (similar to different shapes of clasps in a partial denture). In another example, an appliance according to the fourth embodiment includes a bar on the buccal side and arms pass on the teeth to the lingual side such that the tip of the arm in the removable appliance lies on the lingual side.

Systems or methods according to the third and fourth embodiments (in which an appliance includes a plurality of aligner caps configured to secure to a patient's teeth by fitting over and onto the teeth) can provide distinct advantages of an appliance that can be easily removed by the patient or clinician, in a manner similar to what is done with traditional clear aligners.

Methods of Making and Using Embodiments

Systems and methods according to embodiments described herein may be employed to move or reposition teeth using one appliance, or by progressive use of several appliances, for example, depending on the complication of the dental malocclusion.

According to various examples and embodiments described herein, appliances may be configured and used in techniques that can achieve translational orthodontic tooth movement in one or more (or all three directions) of space (i.e. mesiodistal, buccolingual and occlusogingival). Alternatively or in addition, such appliances may be configured and used in techniques that can achieve rotational movements, such as torque, angulation and rotation (i.e. buccolingual root torque, mesiodistal angulation and mesial out-in rotation).

An example of a method 2000 of making and using an appliance according to various examples and embodiments described herein is described with reference to FIG. 20.

Figure 20:
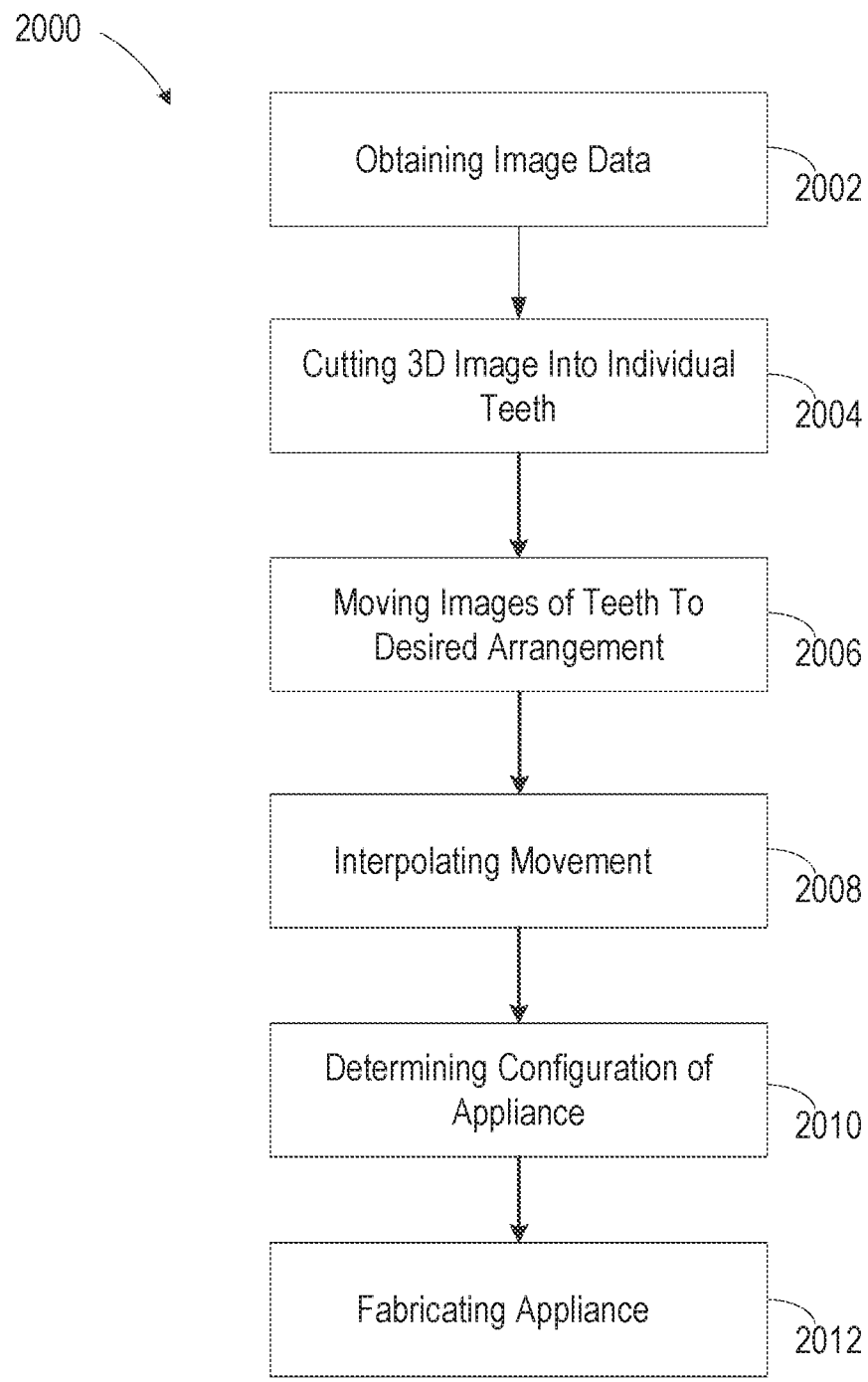
FIG. 20 is a flow chart of a process of fabricating an appliance according to various embodiments.

The method 2000 in FIG. 20 includes obtaining (2002) data representing a 3D OTA of a patient's jaw. The 3D OTA data may include, for example, digital image data obtained by employing an intra-oral scanner on the patient or by using an extra-oral scanner on the plaster casts of the patient's upper and lower dental arches. In other examples, the 3D OTA data may be obtained from other suitable devices and methods, such as, but not limited to imaging an arrangement of the teeth via cone beam computed tomography scans (CBCT), or magnetic resonance imaging (MM). In examples in which plaster casts are used, the relationship between the teeth in the upper and lower arches (inter-arch relationship) can be obtained by taking a wax bite of the patient in the centric position. In examples involving scanning intra-orally, the inter-arch relationship could be recorded by the scanner.

A 3D digital image of the teeth obtained from the 3D OTA data is cut (2004) into individual teeth or blocks of plural teeth (into one or more digital images of individual teeth). The 3D digital image may be cut and manipulated, using suitable processing and software systems, such as, but not limited to a processing device running a computer-aided design (CAD) software. The processing device may include any suitable computer system, mainframe, desktop computer, laptop computer, computer network device or system, mobile electronic pad or communication device, or the like, having capabilities of operating as described herein.

Using the processing device and appropriate software, digital images of the individual teeth are then moved (2006) to a desired or favorable inter-arch and intra-arch arrangements, for example, based on a clinician's prescription. For example, one or more (or all) teeth from the upper or lower jaws (or both) are moved until their cusps have a good interdigitation and fit. A desired or optimal arrangement of the teeth in a jaw may be identified as the FTA for the patient. In particular examples, a qualified clinician may approve the rearrangement after the 3D digital FTA is obtained from the 3D digital OTA.

The processing system interpolates (2008) the movement of the teeth from the 3D digital OTA to the 3D digital FTA. In examples in which multiple appliances are used, progressively, through the treatment, to reach one or more ITAs before reaching an FTA, the processing system interpolates the movement of the teeth from the 3D digital OTA to one or more ITAs, and from an ITA to the FTA. In other examples, a clinician may choose an FTA or ITA, without use of a computerized interpolation, for example, based on the clinician's experience and knowledge, predefined guidelines or combinations thereof.

The processing system determines (2010) a three dimensional appliance configuration, based on the interpolated movement of the teeth between the OTA and FTA (including any ITAs). The processing system calculates (or uses calculations of) the forces and torques required to move each tooth from the OTA to the FTA and any ITAs. The processing system also calculates (or uses calculations of) forces and torques provided by appliance dimensions and configurations and, based on those calculations, designs or otherwise determines an appropriate appliance configuration for providing the forces and torques requested to move each tooth from the OTA to the FTA and any ITAs. By determining appropriate thickness, widths, and configurations of springs, arms bars and other components of an appliance according to one or more of the first, second, third and fourth embodiments described herein, an appliance configuration that applies forces and torques to the appropriate teeth to move the teeth to the FTA or an ITA is determined. An appliance configuration is determined for the FTA and a separate appliance configuration is determined for each ITA. The processing system provides data corresponding to each appliance configuration.

In particular examples, the design of the appliance may be performed by a clinician, manufacturer or technician, with the processor system and appropriate design software such as, but not limited to CAD software such as, but not limited to Solidworks®, Autodesk® Inventor, Creo®, or the like. FEA software such as, but not limited to Abaqus, Ansys, etc. may be employed to design the springs and arms in order to apply the desired or optimal force to the teeth. For example, with respect to the first and third embodiments, such software and processing systems may be employed to design and alter the thickness, cut width, length, as well as the overall configuration of each interdental spring based on the desired movement of the teeth to which the spring is connected.

With respect to the second and fourth embodiments, such software and processing systems may be employed to design and alter the thickness, cut width, length, as well as the overall design of each arm based off of the movement of the tooth to which the arm is connected. For instance, if a tooth needs to be displaced by a longer distance or the tooth is smaller (e.g. lower incisors), the spring or arm may be designed such that it is more flexible. Also, if necessary, the springs/arms can be designed to impart less force on some or all of the teeth because of periodontal problems such as bone resorption, root resorption or attachment loss. The ability, to customize the force or torque (or both) applied to each tooth can provide significant advantages over traditional orthodontics.

One or more appliances are fabricated (2012), based on data provided by the processing system. The processing system may be connected to provide design data corresponding to the appliance configuration to one or more fabrication or manufacturing systems, for controlling the one or more fabrication or manufacturing systems to make one or more appliances (or components of one or more appliances), that are configured to provide the forces and torques to move each tooth from the OTA to the FTA and any ITAs. The connection of the processing system to the one or more fabrication or manufacturing systems may be direct, for example, through an electronic network or other digital connection, or indirect, for example, by storing data from the processing system on a non-transient storage medium and delivering the storage medium to the one or more fabrication or manufacturing systems.

A process according to FIG. 20 may be employed to fabricate one or more appliances according to embodiments described herein. Each appliance may be installed on a patient's teeth, as described herein, to move the teeth from an OTA to an FTA (or to an ITA, or from an ITA to an FTA or another ITA). Appliances can be designed for treating a variety of dental malocclusions that can be treated in traditional orthodontics. In addition, systems and methods, including appliances according to embodiments described herein can be configured to decrease typical treatment time, reduce chair time, decrease the number of visits to the clinician, and decrease the complexity of the work done by the clinician. Another advantage available with embodiments described herein is that appliances according to such embodiments may be configured to be installed behind the teeth, if desired, for example, to minimize visibility.

Embodiments described herein are adaptable to changes in the patient's teeth that may occur as part of the treatment process. For example, a clinician may extract one or more teeth of the patient, due to lack of space for all the teeth to fit in the arch (or other reasons), as part of the treatment. In that event, the extracted teeth can be erased from the 3D digital images employed in calculations described above. If the clinician decides that the teeth need to become smaller due to a lack of space, then interproximal reduction (IPR) may be performed on the patient. In this case stripping and reducing the size of the teeth in the 3D digital images can be performed so as to match the IPR done by the clinician.

In the first and second embodiments described herein, the fabricated appliance is configured to be installed on a patient's teeth, by engaging male connector elements on the appliance with female connector elements bonded to the teeth. In such embodiments, the 3D digital OTA may be used by a clinician when selecting the location and size of the female connector elements (brackets). In certain examples, the female connector elements may be selected or customized to the geometry of the surface of the teeth such that they fit precisely on the surface of the teeth. One option is to bond the female connector elements behind the teeth (to the lingual side of the teeth), for example, to make the appliance aesthetically more appealing. Another option is to bond the female elements to the front of the teeth (the buccal side of the teeth). The buccal version may be preferred in orthognathic surgery cases in which the surgeon would benefit from easy access to the appliance during surgery. However, even in orthognathic surgery cases it is possible for the lingual version to be used. In that case, female connector elements may be installed on the buccal side before surgery and then removed, for example, within a few weeks of the surgery.

A customized tray may be made for indirect bonding of the female connector elements on the surface of the teeth using the 3D digital OTA. The clinician may use the customized tray to attach the female connector elements to the surface of the teeth, using a composite resin or other bonding material. The tray can help the clinician bond the brackets at the optimal position on the tooth. If needed, another customized tray may be made, using the OTA, to assist the clinician in implanting the temporary anchorage devices (TADs) at the optimal position. Before using the tray as a guide to insert the TADs the clinician may anesthetize the desired insertion location for patient comfort. The TAD's are placed, if additional anchorage is needed for tooth movement. The decision on whether or not to use the TADs can be made by the clinician and chosen treatment plan. If desired, stabilization can be increased by including a palatal arch on the appliance for the upper jaw or a lingual arch on the appliance for the lower jaw.

Alternatively, the clinician may attach the female elements on the teeth directly, without the assistance of a tray. Likewise, the clinician could insert the TADs in the jaw without the use of a guiding tray. In that case, an intraoral scan, cone beam computed tomography (CBCT), or other suitable scan or image may be taken of the patient, after the female elements or TAD(s) are manually placed. Then the appliance will be fabricated or manufactured based on the position of the female parts or TADs that the clinician chose.

For appliances according to the third and fourth embodiments, the clinician may use the 3D digital OTA to select the location and size of each cap as well as the attachment elements. The caps and attachment elements may be customized to the geometry of the surface of the teeth such that they fit precisely on the surface of the teeth. In some examples, the attachments are attached behind the teeth (the lingual side of the teeth), which makes the appliance aesthetically more appealing. In other examples, the attachments are attached in front of the teeth (the buccal side of the teeth). The buccal version may be preferred in orthognathic surgery cases in which the surgeon would benefit from easy access to the appliance during surgery. However, even in orthognathic surgery cases it is possible for the lingual version to be used. In that case, attachments may be installed on the buccal side before surgery and then removed, for example, within a few weeks of the surgery.

A customized tray may be made for indirect bonding of the attachments to the surface of the teeth using the 3D digital OTA. The clinician may use the customized tray to attach the attachments to the surface of the teeth using composite resin or other bonding material. The tray can help the clinician bond the attachments at the desired or optimal position. If needed, another customized tray may be made, using the OTA, to allow the clinician to insert the temporary anchorage devices (TADs) at a desired or optimal position. Before using the tray as a guide to insert the TADs the clinician may anesthetize the desired insertion location for patient comfort. These TAD's are placed if additional anchorage is needed for tooth movement. The decision on whether or not to use the TADs will be made by the clinician and chosen treatment plan. If desired, stabilization can be increased by including a palatal arch on the appliance for the upper jaw or a lingual arch on the appliance for the lower jaw.

Alternatively, the clinician may attach the attachments on the teeth directly, without the assistance of a tray. Likewise, the clinician could insert the TADs in the jaw without the use of a guiding tray. In that case, an intraoral scan, CBCT or other suitable scan or image may be taken of the patient, after the female elements or TAD(s) are manually placed. Then the appliance will be fabricated or manufactured based on the position of the attachments or TADs that the clinician chose.

In the first and second embodiments, after each appliance is fabricated and the female connector elements are attached to the teeth, each male element of the appliance will be engaged into its associated female element to install the appliance. Once installed, the appliance imparts forces and torques on the teeth, to move the teeth to the desired FTA or ITA. After each stage of treatment is completed (OTA to FTA, OTA to ITA, ITA to ITA, or ITA to FTA) the male elements will sit passively in the female elements and force will no longer be applied to the teeth. At that stage the male elements may be removed and the next appliance may be installed, using the same female connector elements. However, if the previous appliance has been the one made based on the FTA then the treatment has been completed. Based on the clinician's opinion one or more appliances may be built and installed for finishing, detailing and the ultimate fine positioning of the teeth.

In the third and fourth embodiments, after each appliance is fabricated, each cap of the appliance may be engaged with the appropriate tooth or teeth, in some examples, with the help of an attachment. Once installed, the appliance imparts forces and torques on the teeth, to move the teeth to the desired FTA or ITA. After each stage of treatment is completed (OTA to FTA, OTA to ITA, ITA to ITA, or ITA to FTA) the caps will sit passively on the teeth and force will no longer be applied to the teeth. At that stage the caps will be removed and the next appliance will be inserted in the patient's mouth. However, if the previous appliance has been the one made based on the FTA then the treatment has been completed. Based on the clinician's opinion one or more appliances may be built and installed for finishing, detailing and the ultimate fine positioning of the teeth.

The appliances according to the first and second embodiments, and female connector elements associated with those embodiments, may be manufactured in any suitable manner, including, but not limited to molding, casting, machining, 3D printing, stamping, extruding, or the like. For example, 3D metal printers may be used to directly print the appliances out of nitinol, steel, beta-titanium, or other suitable metals or alloys. In other examples, the appliance is first printed out of castable wax and then the wax pattern is investment cast into Nitinol, steel, beta-titanium, among other metals or alloys. In another example, the appliance is directly printed with a polymer or elastomeric material.

However, in particular embodiments, appliances or female connector elements (or both) of examples of various embodiments described herein are made by cutting a 2D form of the appliance from a 2D sheet of material and bending the 2D form into a desired 3D shape of the appliance. Such methods are particularly suitable for making appliances according to examples of the first and second embodiments described herein, or for the arch-shaped structure or metal part of an appliance according to examples of the third and fourth embodiments described herein.

Thus a method of making an appliance according to any suitable example embodiment described herein and, in particular examples, for making an appliance according to embodiments described herein includes designing an appliance configuration using suitable processing and hardware systems, for example, as described herein with reference to method 2000, where the fabrication (2012) of one or more appliances involves cutting a 2D form of the appliance from a 2D sheet of material and bending the 2D form into a desired 3D shape of the appliance.

Figure 21:
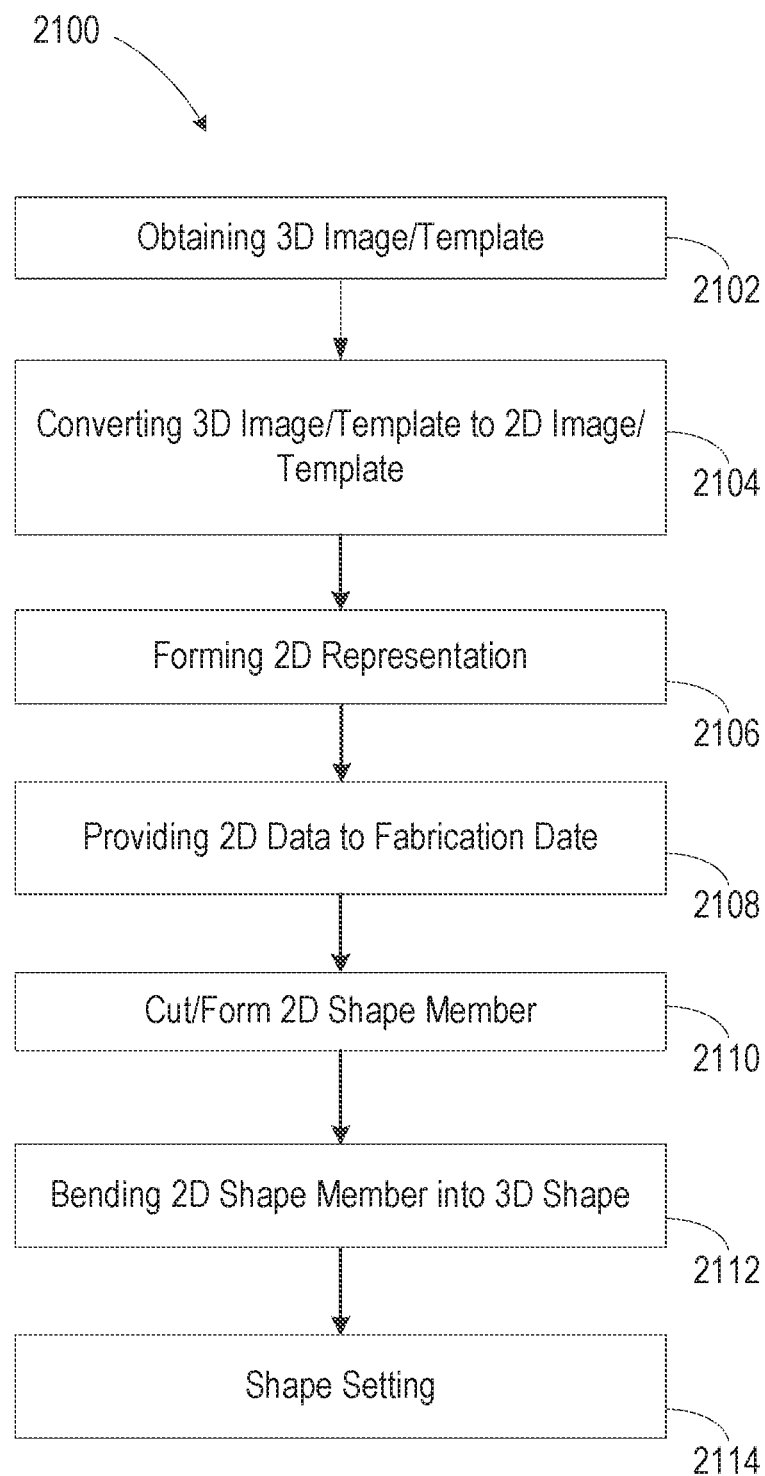
FIG. 21 is a flow chart of a further process of fabricating an appliance according to various embodiments.

More specifically, with reference to FIG. 21, an example of a method 2100 of fabrication (corresponding to feature 2012 in method 2000), includes forming a 3D image or template (2102), based on the 3D configuration determined at 2010 in method 2000. The image or template of the appliance may be designed by a clinician, manufacturer, or technician, using a processor system and appropriate design software such as, but not limited to CAD software such as, but not limited to Solidworks®, Autodesk® Inventor, Creo®, or the like. An example of a 3D template 1800 of an appliance, as designed in Solidworks® and Autodesk® Inventor is shown in FIG. 18*a*.

The method 2100 includes converting (2104) the 3D image or template into a 2D image or template. Such conversion may be carried out using a processor system and appropriate flattening software such as, but not limited ExactFlat® or other suitable software. FIG. 18*b* shows an example of a 2D image or template 1802 of the 3D template of FIG. 18*a*.

Then, a 2D representation of the appliance is formed (2106) from and based on the 2D image or template, using a processor system and appropriate software, such as, but not limited to CAD software such as, but not limited to Solidworks®, Autodesk® Inventor, Creo®, or the like. FIG. 18*c* shows an example of a 2D representation 1804 of an appliance, based on the 2D image or template of FIG. 18*b*. In particular examples, the 2D representation may include one or more temporary arms 1806 that are used to fix the appliance to a mandrel during bending or setting (heat treating) procedures. In further examples, the 2D representation may include one or more anchorage device holders such as, but not limited to those described herein.

Then, data corresponding to the 2D representation of the appliance is provided (2108) to a suitable fabrication device (such as, but not limited to one or more machines that perform cutting, laser cutting, milling, wire EDM, water jetting, punching (stamping), or the like) for cutting a flat sheet of material into a member having a 2D shape of the 2D representation of the appliance. The fabrication device is controlled by the data to fabricate a 2D member that has a shape of the 2D representation of the appliance. The 2D member may be cut (2110) from a flat sheet of any suitable material, such as, but not limited to nitinol, stainless steel, cobalt chrome, or another type of metal. In particular examples, the flat sheet of material is a sheet of Nitinol (NiTi), such that the 2D member cut from the flat sheet has the shape of a 2D representation of the appliance, in Nitinol (NiTi). FIG. 18*d* shows an example of a 2D member 1808 fabricated based on the 2D representation 1804 of FIG. 18*c*. In examples in which temporary arms 1806 were added, the temporary arms may be omitted from the 2D member (or may be included and subsequently cut or removed from the 2D member).

After cutting the 2D member from the flat sheet of Nitinol (NiTi) or other suitable material, the method includes bending (2112) the 2D member into a desired 3D shape, corresponding to the 3D image or template from which the 2D member was made. In certain examples, one or more mandrels are configured for use in bending the 2D member into a desired 3D shape configuration. In such examples, after cutting the 2D member, the 2D member is fixed on or between one or more mandrels. The 2D member is bent on or between the mandrels, to form a desired 3D shape. FIG. 18*e* shows an example of an appliance 1810 having a 3D shape that was formed by bending the 2D member 1808 of FIG. 18*d* into a desired configuration.

One or more shape setting procedures 2114, such as, but not limited to heat treatment, may be applied to the 3D shape, during or after the bending operation, to set the desired 3D shape. A shape setting procedure involving a heat treatment may include rapid cooling, following heating of the member during or after bending.

One example, of a heat treatment procedure can include heating the member (during or after it has been bent into the desired 3D shape) to a selected temperature (such as, but not limited to 550 degrees centigrade) for a selected period of time (such as, but not limited to 10 minutes), followed by rapid cooling. The rapid cooling can be achieved by any suitable cooling procedure such as, but not limited to water quench or air-cooling. In other examples, the time and temperature for heat treatment can be different than those discussed above, for example, based upon the specific treatment plan. For example, heat treatment temperatures can be within a range from 200 degrees centigrade to 700 degrees centigrade and the time of heat treatment can be a time in the range up to about one hundred and twenty minutes. In particular examples, the heat treatment procedure may be carried out in an air or vacuum furnace, salt bath, fluidized sand bed or other suitable system. After completing the heat treatment, the appliance has a desired 3D shape and configuration. In other examples, other suitable heat treating procedures may be employed including, but not limited to resistive heating or heating by running a current though the metal of the appliance structure. One or more additional, for example, post processing operations may be provided on the 3D shaped article, including, but not limited to polishing, electropolishing, electroplating, coating, sterilizing or other cleaning or decontamination procedures).

As described above, FIG. 18e shows an example of an appliance 1810 having a 3D shape that was formed by bending the 2D member 1808 of FIG. 18d into a desired configuration. Another example of an appliance 1820 having a 3D shape that was formed by bending a 2D member into a desired configuration is shown in FIG. 18f. The example appliance 1820 in FIG. 18f includes a plurality of arms having male connector elements 1822, similar to the male connector elements 1802 of the appliance 1810 in the example in FIG. 18e. However, the springs 1824 on the arms of the appliance 1820 have a different shape than the springs on the arms of the appliance 1810. In addition, the appliance 1820 has TAD holders 1826 that have a generally U or Y shape structure, as compared to the annular or O ring shape of the TAD holders of the appliance 1810 in the example shown in FIG. 18e. The appliance 1820 in FIG. 18f may be made in a manner similar to the manner of making the appliance 1810 described herein.

In examples in which the appliance is made of multiple components, some (or each) of the components of the appliance may be made according to methods described above (including, but not limited to the methods 2000 and 2100), and then connected together to form the desired 3D appliance configuration. In these or other examples, the appliance (or some or each component of the appliance) may be made in other suitable methods including, but not limited to: directly printing of metal, first printing of a wax member and then investment casting the wax member into a metal or other material, printing of elastomeric material or other polymer, or cutting the components out of a sheet of metal and shape setting into the desired 3D configuration.

As discussed herein, one or more mandrels may be configured for use in bending a cut 2D member into a desired 3D shape configuration. In particular examples, one or more mandrel is provided (such as, but not limited to, custom made) for each jaw of a patient. For example, the mandrels may be customized in shape and configuration for each patient and can be made in any suitable manner, including molding, machining, direct metal printing of stainless steel or other suitable metals, 3D printing of a suitable material, such as, but not limited to a steel/copper mix via binder jetting, as well as first printing the configuration in wax and then investment casting the wax into various metals. In various examples described herein, the mandrel may be configured of material that is sufficiently resistant to the temperature of the heat treatment. In particular examples, one or more robots may be employed with or without the one or more mandrels, for bending the cut 2D member into a desired 3D shape configuration.

By employing a cut 2D member, instead of a traditional single-diameter wire, a greater variety of 3D shapes may be made, as compared to shapes made by bending single-diameter wire. The cut 2D member may have designed or varying widths and lengths that, when bent into a desired shape, can result in portions of the 3D appliance having variances in thickness, width and length dimensions. In this manner, the 2D member can be cut into a shape that provides a desired thickness, width and length of spring members, arms, or other components of the appliance. A larger variety of shapes may be provided by bending a custom cut 2D member, as compared to bending a single-diameter wire.

As discussed above, a method 2100 in which a 3D appliance configuration is made from a cut 2D member may be particularly suited for making an appliance according to the first and second embodiments or metal part of an appliance according to the third and fourth embodiments. In particular examples, the entire appliance (including male connector elements and springs) is configured by bending the cut 2D member into the desired 3D shaped member. In other examples, additional components may be attached to the 3D shape, for example, after bending 2112, where such additional components may include, but are not limited to male connector elements (such as, but not limited to those shown in FIG. 12), spring members, arms, cap connector elements, TAD holders, or the like. Such additional components may be attached to the 3D shaped member by any suitable attachment mechanism including, but not limited to, adhesive material, welding, friction fitting, or the like.

Similarly, the metal portion of an appliance according to the third and fourth embodiments can also be made from a cut 2D member, using methods 2000 and 2100 as described herein. Once the metal part of the appliance is configured (cut from a 2D sheet of material and bent into a desired 3D shaped member), one or more caps may be attached to attachment elements formed on (or attached to) the metal part. In particular examples, the caps may be configured and attached to the 3D shaped member such that caps of adjacent teeth may not come in contact with each other during the course of treatment. In certain examples, an Essix® machine or other suitable thermoforming or vacuum forming machine can be used to attach each cap to a respective cap connector element on the 3D shaped member.

Additional components may be attached to the 3D shaped member, for example, after bending (2112), where such additional components may include, but are not limited to male connector elements (such as, but not limited to those shown in FIG. 12), spring members, arms, cap connector elements, TAD holders, or the like. Such additional components may be attached to the 3D shaped member by any suitable attachment mechanism including, but not limited to, adhesive material, welding, friction fitting, or the like.

The caps may be configured and connected to the 3D shaped member with enough clearance between adjacent caps so as to provide room for the springs and arms to move. In further examples, the aligner cap is configured to only cover the teeth, and the aligner may be trimmed either manually or with another cutting method described herein.

A further method of fabricating an appliance according to the third embodiment is described and shown in FIGS. 19a-19c. With reference to FIG. 19a, a 3D printed model or mold 1900 of a patient's ITA or FTA is produced, according to procedures as described herein. The model or mold 1900 may be made of any suitable polymer, ceramic, metal, or the like. In further examples, the mold may include a larger portion of the patient's palate than shown in FIGS. 19a-19c. In addition, an arch-shaped structure 1902 is made of metal or other suitable material, according to procedures as described herein for producing an appliance of the first embodiment. In one example, an arch-shaped structure 1902 has a shape and configuration similar to the appliance in FIG. 17a is produced as described herein. In other examples, arch-shaped members having other suitable shapes may be employed. The arch-shaped structure 1902 is placed in the model or mold, or is attached to the model or mold, as shown in FIG. 19a by any suitable attaching mechanism, including, but not limited to an adhesive, ligature wire, or the like.

Then, then thermally settable material is pressed into the model or mold 1900 for example, using an Essix® machine or other suitable thermoforming or vacuum forming machine, while the arch-shaped structure 1902 is present in the model or mold. As a result, the arch-shaped structure becomes embedded in the thermally settable material. In particular examples, the thermally settable material is a thermally settable plastic such as, but not limited to a sheet of Essix® plastic having a thickness of up to about 2 mm.

In other examples, one or more layers of a thermally settable material may be pressed on the model or mold 1900, before the arch-shaped structure 1902 is placed in the model or mold. Then, the arch-shaped structure 1902 may be placed on top of the thermally settable material (before or after setting the thermally settable material to the shape of the model or mold). Then one or more further layer of thermally settable material may be placed on the arch-shaped structure 1902 and the previously placed thermally settable material, and set to the shape of the model or mold. Accordingly, the arch-shaped structure 1902 may be secured between two or more layers of thermally set material, formed in the shape of the model or mold. In particular examples, the thermally settable material may be cut and removed in the areas covering spring members or other flexible portions of the arch-shaped member or arms extending from the arch-shaped member (before or after thermal setting), to minimize or eliminate any obstruction to the motion and flexibility of the spring members or flexible portions.

When sufficiently cured, the thermally settable material (with the arch-shaped member) is removed from the model or mold 1900. When removed from the model or mold, the molded plastic (and arch-shaped structure embedded in the molded plastic) forms a three-dimensional structure 1910 of a cap for the entire jaw of teeth, as shown in FIG. 19*b*. The molded plastic structure 1910 is then cut, by forming cuts between each pair of adjacent teeth, to form an appliance 1920 as shown in FIG. 19*c*. Such cutting may be carried out by any suitable cutting procedure such as, but not limited to milling, laser cutting, or the like. While various materials may be employed for the appliance examples according to the embodiments described herein, particular examples are made from a shape memory alloy, such as Nitinol (NiTi), which contains Nickel and Titanium. Nitinol can be sufficiently elastic and has shape memory properties. Accordingly, by using Nitinol, the force applied to the teeth may decay slower than the force generators in traditional braces. Therefore, systems and methods according to embodiments described herein may be configured so as to require fewer appliances (thus, simplifying treatment) as compared to traditional orthodontics and techniques.

In the course of some treatments, a clinician may perform an extraction for various reasons, including: crowded teeth due to relatively large teeth in comparison to the patient's jaw, damaged teeth that need to be extracted, or other reasons. When an extraction is performed, the neighboring non-extracted teeth tend to move towards each other, to close the extraction space. Certain systems and methods (including appliances) according to embodiments described herein may be employed to close an extraction space, either asymmetrically, which is called minimum/maximum anchorage, or symmetrically, which is called moderate anchorage. In particular examples, TADs could also be used to provide anchorage for closing the extraction space. In such examples, one or more TADs may be arranged to hold a passive appliance towards one side of the extraction space to close the space asymmetrically. On the other hand, one or more TADs may be arranged in the middle of a passive appliance, to close a space symmetrically. The closure of space can be accomplished by employing an appliance according to embodiments described herein, to change the angulation of the teeth or by using more rigid springs for the teeth that are meant to relatively move less. Similarly, more flexible springs could be used for the teeth that need to be moved further.

Figure 22A:
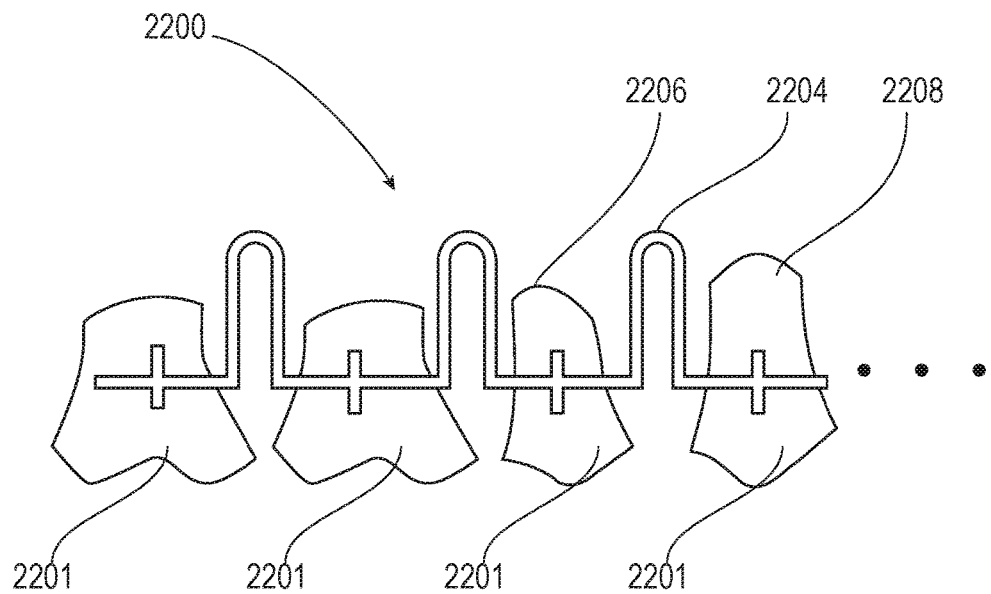
FIG. 22a is a schematic representation of an appliance according to the third embodiment, in a passive state.
Figure 22B:
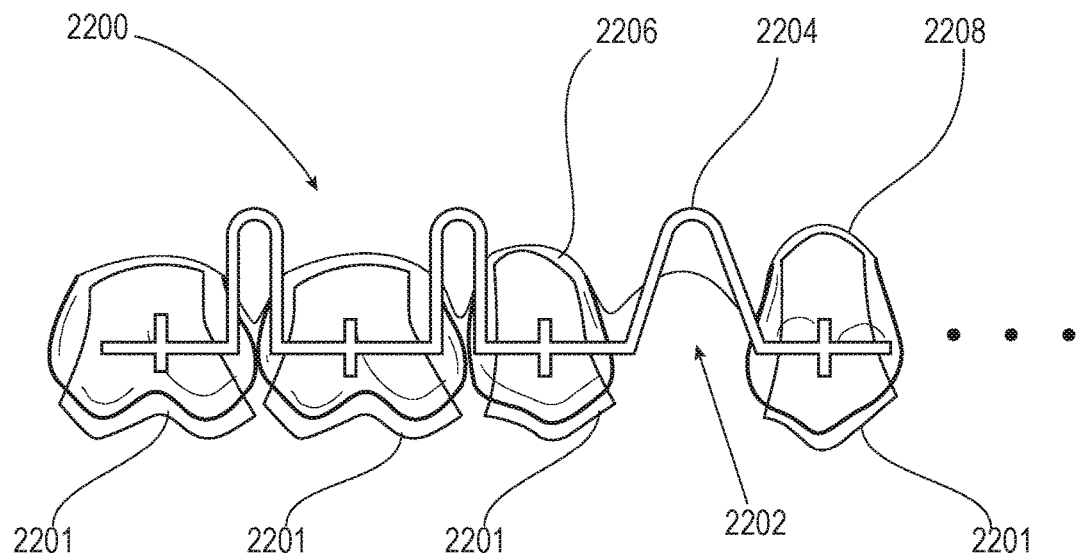
FIG. 22b is a schematic representation of an appliance according to the third embodiment, connected to teeth and in an active state.

Example processes of closing an extraction space, using an appliance according to embodiments described herein, is shown and described with reference to FIGS. 22*a* and 22*b*. Referring to FIGS. 22*a* and 22*b*, an appliance 2200 (shown in partial view) includes a plurality of caps 2201, in accordance with the third embodiment. The appliance 2200 is shown as disengaged from teeth in FIG. 22*a* and in an un-tensioned or passive state. The appliance 2200 is shown as engaged and secured to the teeth in FIG. 22*b*. In FIG. 22*b*, an extraction space 2202 is shown, for example, at a location where a tooth (such as, but not limited to a premolar) has been extracted. When the appliance 2200 is installed, a spring member (formed by an interdental loop 2204) is in a tensioned state and imparts a force on one or both adjacent teeth (e.g., on the upper second premolar 2206 and the upper canine 2208), to move those teeth and close the extraction space 2202.

Figure 23A:
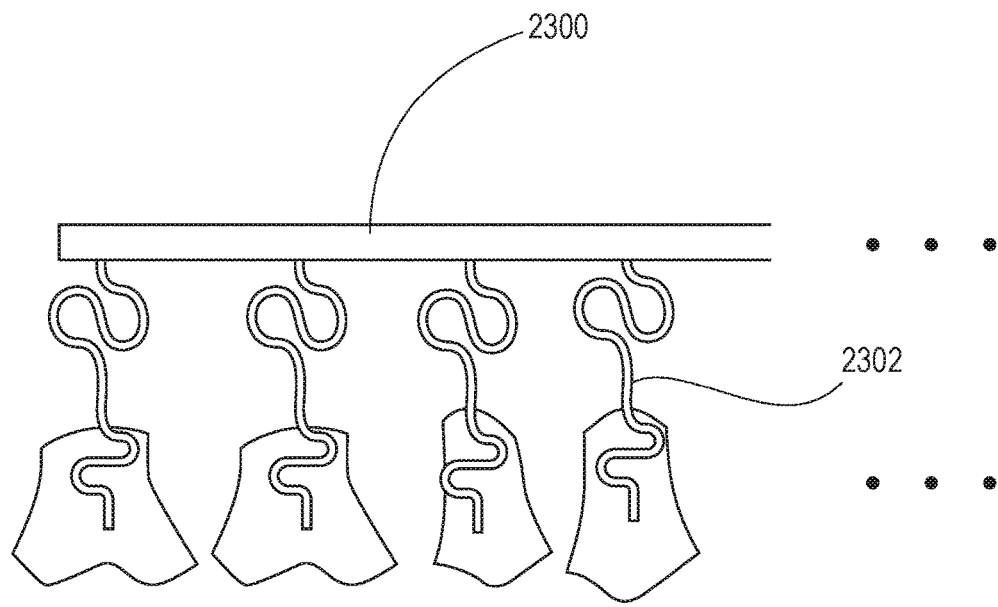
FIG. 23a is a schematic representation of an appliance according to the fourth embodiment, in a passive state.
Figure 23B:
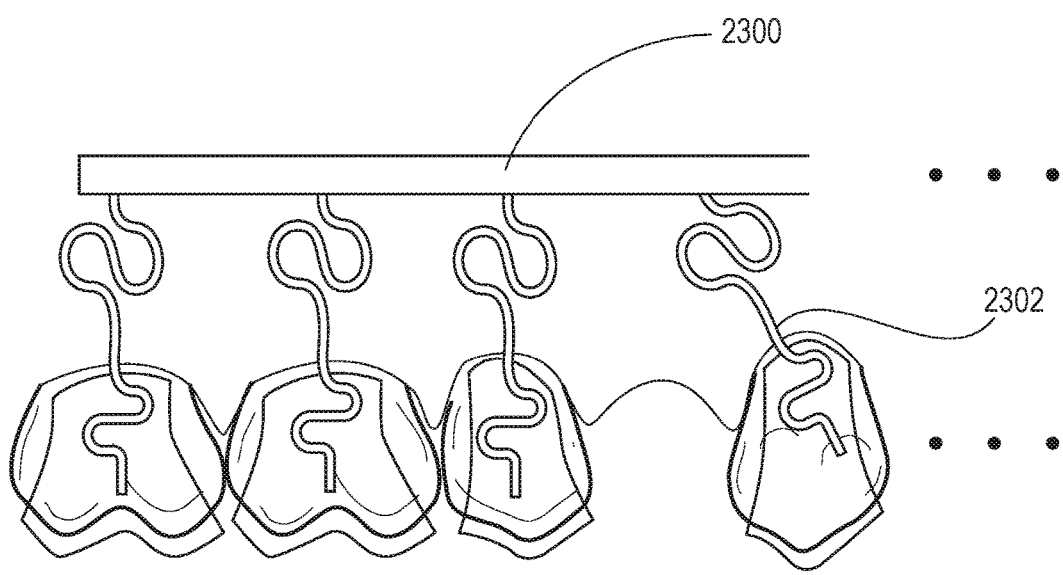
FIG. 23b is a schematic representation of an appliance according to the fourth embodiment, connected to teeth and in an active state.
Figure 24:
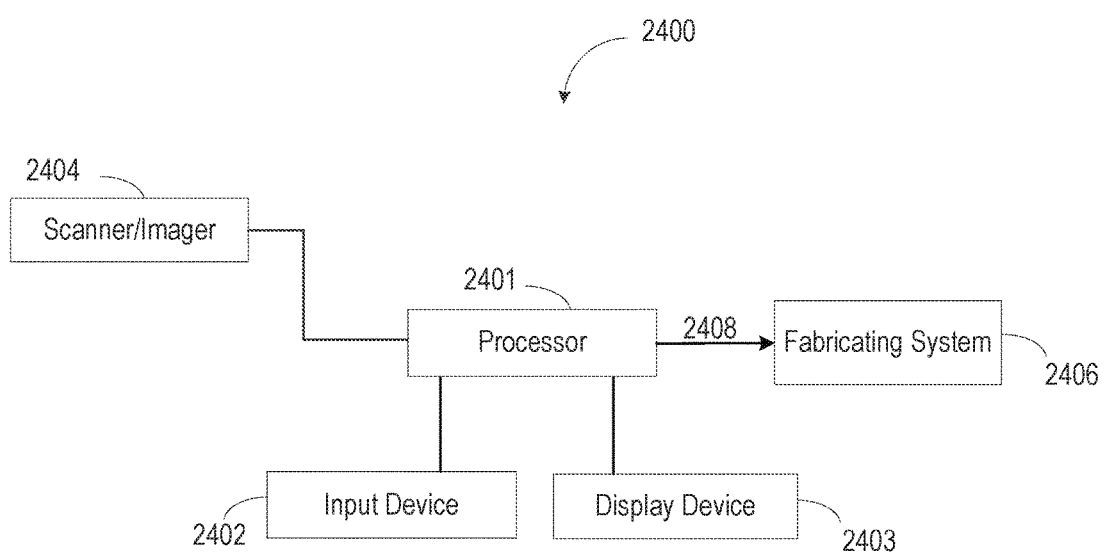
FIG. 24 is a generalized schematic representation of a processing system that may be used to implement certain examples of embodiments.

Another example appliance according to the fourth embodiment is described and shown with respect to FIGS. 23*a* and 23*b*. In FIG. 23*a*, an appliance 2300 (shown in partial view) according to an example of certain embodiments described herein is in a passive state, such as, before it is placed in the patient's mouth. In FIG. 23*b*, the appliance 2300 is connected to teeth, for example, using caps as described herein. In FIG. 23*b*, the arm 2302 of the appliance 2300 is connected to a canine tooth, and is stretched as compared to the arm 2302 shown in FIG. 23*a*, due to the extraction space and the force of the spring on the arm 2302.

Methods as described with reference to FIGS. 20 and 21 may be carried out with a clinician (or other suitable personnel), using a processing system as described. A generalized representation of a processing system 2400 that may be employed for such methods is shown in 24 and includes a processor 2401, an input device 2402, a display device 2403 and an imaging or scanning device 2404 (or other suitable device for imaging a patient's OTA). The processor 2401 may be connected to one or more fabricating systems 2406 (including fabricating machines) for fabricating appliances (and components thereof and tools therefor), as described herein. The processor 2401 may be connected to the fabricating system(s) 2406 by any suitable communication connection 2408 including, but not limited to a direct electronic connection, network connection, or the like. Alternatively, or in addition, the connection 2408 may be provided by delivery to the fabricating system 2406 of a physical, non-transient storage medium on which data from the processor has been stored. The non-transient storage medium may include, but is not limited to one or more of an RSB connectable memory, a memory chip, a floppy disk, a hard disk, a compact disk, or any other suitable, non-transient data storage medium.

While various embodiments and examples described herein include or employ male connection elements on an appliance that engage and secure to female connection elements on teeth, other embodiments and examples may be configured similarly, but with the female connection elements on the appliance and male connection elements on the teeth.

The embodiments disclosed herein are to be considered in all respects as illustrative, and not restrictive. The present disclosure is in no way limited to the embodiments described above. Various modifications and changes may be made to the embodiments without departing from the spirit and scope of the disclosure. Various modifications and changes that come within the meaning and range of equivalency of the claims are intended to be within the scope of the disclosure.

What is claimed is:

1. An appliance for installing on a patient's teeth, the appliance comprising:
an arch shaped member;
a plurality of arms extending from the arch shaped member, each arm being associated with one or more different respective ones of the patient's teeth relative to each other arm of the plurality of arms;
a plurality of securing members for securing to a plurality of the patient's teeth, each of the securing members being coupled to or provided on a respective one of the arms;
wherein the arch shaped member and the plurality of arms, together, comprise a unitary structure having a uniform thickness dimension of a sheet of material, the unitary structure having a length dimension and a width dimension with varying widths along the length dimension, the unitary structure being configured to be bent into a three dimensional structure in which the arch shaped member is shaped to extend along one side of a plurality of adjacent ones of the patient's teeth.

2. The appliance of claim 1, wherein each securing member comprises: (a) a separate respective male connector element configured to engage with one or more separate respective female connector elements bonded to one or more of the patient's teeth; or (b) a separate respective cap configured to fit over and onto one or more of the patient's teeth.

3. The appliance of claim 1, wherein:
the arch shaped member is configured to correspond to and extend along an arch of the patient's jaw when the appliance is installed on the patient's teeth; and
the appliance includes at least one spring member, wherein each spring member is arranged along the arch shaped member at a location between two teeth in the jaw of the patient, when the arch shaped member extends along the arch of the patient's jaw.

4. The appliance of claim 1, wherein each respective securing member of the plurality of securing members is attached to at least one different respective one of the arms relative to each other securing member.

5. The appliance of claim 4, wherein each securing member comprises: (a) a separate respective male connector element configured to engage with one or more separate respective female connector element bonded to one or more of the patient's teeth; or (b) a separate respective cap configured to fit over and onto one or more of the patient's teeth.

6. The appliance of claim 1, further comprising a plurality of spring members, wherein each respective spring member of the plurality of spring members is provided along a different respective one of the arms relative to at least one other spring member.

7. The appliance of claim 6, wherein each respective spring member is part of the unitary structure of the arch shaped member and the plurality of arms.

8. The appliance of claim 7, wherein the unitary structure of the arch shaped member, the plurality of arms and the spring members is made of a single, uniform material.

9. The appliance of claim 1, further comprising a plurality of spring members, wherein each spring member is provided on a respective one of the arms, at a location between the arch shaped member and the securing member attached to the arm.

10. The appliance of claim 9, wherein each securing member is separated from and does not cover any portion of the spring member of the arm to which the securing member is attached.

11. The appliance of claim 1, wherein each securing member comprises a separate respective cap configured to fit over and onto one or more of the patient's teeth when the appliance is installed, such that the plurality of securing members comprises a plurality of caps that are arranged along the arch shaped member, and wherein each separate respective cap is disconnected from one or more other caps of the plurality of caps.

12. The appliance of claim 1, wherein each securing member comprises a T shaped member that is configured to engage with a slot in a female connector element bonded to one of the patient's teeth.

13. The appliance of claim 1, wherein the arch shaped member of the three dimensional structure is a lingual arch shaped member configured to extend along a lingual side of the plurality of adjacent ones of the patient's teeth.

14. The appliance of claim 13, wherein the arch shaped member and the plurality of arms are formed of the same material.

15. The appliance of claim 1, wherein the arch shaped member and the plurality of arms are formed of the same material.

16. The appliance of claim 1, wherein the unitary structure of the arch shaped member and the plurality of arms is formed of nitinol, shape memory metal or shape memory metal alloy.

17. The appliance of claim 1, wherein the unitary structure of the arch shaped member and the plurality of arms comprises a sheet of material of uniform thickness, where one surface of the sheet of material has a 2-dimensional shape defining the shape of the arch shaped member and the plurality of springs.

18. An appliance for installing on a patient's teeth, the appliance comprising:
an arch shaped member configured to extend along one side of a plurality of adjacent teeth in a patient's jaw;
a plurality of arms extending from the arch shaped member, each arm being associated with one or more different respective ones of the patient's teeth relative to each other arm of the plurality of arms; and
a plurality of securing members for securing to a corresponding plurality of connector members that are attached to at least some of the teeth of the plurality of adjacent teeth in the patient's jaw before installing the appliance on the patient's teeth, wherein each respective securing member of the plurality of securing members is attached to one or more of the arms;
wherein the arch shaped member and the plurality of arms, together, comprise a single unitary body that forms a three dimensional structure.

19. The appliance of claim 18, wherein each respective securing member of the plurality of securing members is attached to a different respective one of the arms relative to each other securing member of the plurality of securing members.

20. The appliance of claim 18, wherein each securing member comprises: (a) a separate respective male connector element configured to engage with one or more respective female connector elements bonded to one or more of the patient's teeth; or (b) a separate respective cap configured to fit over and onto one or more of the patient's teeth.

21. The appliance of claim 18, further comprising a plurality of spring members coupled to or provided on one or more of the plurality of arms such that one or more of the arms includes at least one spring member.

22. The appliance of claim 21, wherein each spring member is provided on a respective one of the arms, at a location between the arch shaped member and the securing member attached to the arm.

23. The appliance of claim 21, wherein each securing member is separated from and does not cover any portion of the spring member of the arm to which the securing member is attached.

24. The appliance of claim 18, wherein each securing member comprises a separate respective cap configured to fit over and onto one or more of the patient's teeth when the appliance is installed, such that the plurality of securing members comprises a plurality of caps that are arranged along an arch formed by the arch shaped member, and wherein each separate respective cap is disconnected from one or more other caps of the plurality of caps.

25. The appliance of claim 18, wherein the arch shaped member is a lingual arch shaped member configured to extend along a lingual side of the plurality of adjacent teeth in the patient's jaw.

26. The appliance of claim 25, wherein the arch shaped member and the plurality of arms are formed of the same material.

27. The appliance of claim 18, wherein the arch shaped member and the plurality of arms are formed of the same material.

28. The appliance of claim 18, wherein the single unitary structure of the arch shaped member and the plurality of arms is formed of nitinol, shape memory metal or shape memory metal alloy.

\* \* \* \* \*